(12) United States Patent
He et al.

(10) Patent No.: US 11,845,777 B2
(45) Date of Patent: *Dec. 19, 2023

(54) STABILIZED CORONAVIRUS SPIKE (S) PROTEIN IMMUNOGENS AND RELATED VACCINES

(71) Applicant: The Scripps Research Institute, La Jolla, CA (US)

(72) Inventors: Linling He, San Diego, CA (US); Jiang Zhu, San Diego, CA (US); Ian A. Wilson, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 409 days.

This patent is subject to a terminal disclaimer.

(21) Appl. No.: 17/087,704

(22) Filed: Nov. 3, 2020

(65) Prior Publication Data

US 2021/0139543 A1 May 13, 2021

Related U.S. Application Data

(63) Continuation of application No. 17/019,825, filed on Sep. 14, 2020, now Pat. No. 10,906,944.

(60) Provisional application No. 63/045,557, filed on Jun. 29, 2020.

(51) Int. Cl.
| | |
|---|---|
| *C07K 14/005* | (2006.01) |
| *A61P 31/14* | (2006.01) |
| *C12N 7/00* | (2006.01) |
| *A61K 39/215* | (2006.01) |
| *A61K 39/00* | (2006.01) |

(52) U.S. Cl.
CPC .......... *C07K 14/005* (2013.01); *A61K 39/215* (2013.01); *A61P 31/14* (2018.01); *C12N 7/00* (2013.01); *A61K 2039/57* (2013.01); *A61K 2039/575* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| 10,906,944 B2 * | 2/2021 | He ............................ A61P 31/14 |
| 2017/0233441 A1 | 8/2017 | Kwong et al. |
| 2020/0009244 A1 | 1/2020 | He et al. |

FOREIGN PATENT DOCUMENTS

| WO | 2005063801 A2 | 7/2005 |
| WO | 2017192434 A1 | 11/2017 |
| WO | 2018081318 A1 | 5/2018 |
| WO | WO 2018/081318 A1 * | 5/2018 |
| WO | 2019089817 A1 | 5/2019 |
| WO | 2019241483 A1 | 12/2019 |

OTHER PUBLICATIONS

Montesinos-Guevara et al., Cochrane Database of Systematic Reviews, 2022, Issue 12, Art No. CD002190, 61 pages. (Year: 2022).*
Yong et al., 2019, Front. Microbiol., 10:1781, 18 pages. (Year: 2019).*
Li et al., J. Biomed. Sci., 2020, 27:104, 23 pages. (Year: 2020).*
Hoffmann et al., Molecular Cell, 2020, 78:779-784. (Year: 2020).*
Wu et al., Nature, Mar. 12, 2020, 579:267-269, and extended data pages. (Year: 2020).*
Aldon, et al., Rational Design of DNA-Expressed Stabilized Native-Like HIV-1 Envelope Trimers, Cell Reports 24, pp. 3324-3338, Sep. 18, 2018.
Barnes, et al., Structures of Human Antibodies Bound to SARSCoV-2 Spike Reveal Common Epitopes and Recurrent Features of Antibodies, Cell 182, pp. 828-842, Aug. 2020.
Cai, et al., Distinct Conformational States of SARS-CoV-2 Spike Protein, Science 369, pp. 1586-1592, Sep. 2020.
Graham, et al., Rapid COVID-19 Vaccine Development, Science, vol. 368, pp. 945-946, May 2020.
He, et al, Presenting Native-like Trimeric HIV-1 Antigens with Self-assembling Nanoparticles, Nature Communications, Jun. 2016, 7:12041, DOI: 10.1038/ncomms12041.
He, et al., HIV-1 Vaccine Design Through Minimizing Envelope Metastability, Science Advances, Nov. 2018, 4: eaau6769.
He, et al., Single-component Multilayered Self-assembling Nanoparticles Presenting Rationally Designed Glycoprotein Trimers as Ebola Virus Vaccines, bioRxiv doi: https://doi.org/10.1101/2020.08.22.262634, Aug. 2020.
He, et al., Proof of Concept for Rational Design of Hepatitis C Virus E2 Core Nanoparticle Vaccines, Science Advances, Apr. 2020, 6:eaaz6225.
Henderson, et al., Controlling the SARS-CoV-2 Spike Glycoprotein Conformation, bioRxiv https://doi.org/10.1038/s41594-020-0479-4, May 2020.
Hsia, et al., Design of a Hyperstable 60-Subunit Protein Icosahedron, Nature, Jul. 2016, vol. 535, pp. 136-147.
Hsieh, et al., Structure-Based Design of Prefusion-Stabilized SARS-CoV-2 Spikes, Science, Sep. 2020, vol. 369, pp. 1501-1505.
Ke, et al., Structures, Conformations and Distributions of SARS-CoV-2 Spike Protein Trimers on Intact Virions, bioRxiv preprint DOI,10.1101/2020.06.27.174979, Jun. 2020.

(Continued)

*Primary Examiner* — Stacy B Chen
(74) *Attorney, Agent, or Firm* — Hugh Wang; Thomas Fitting

(57) ABSTRACT

The present invention provides redesigned soluble coronavirus S protein derived immunogens that are stabilized via specific modifications in the wildtype soluble S sequences. Also provided in the invention are nanoparticle vaccines that contain the redesigned soluble S immunogens displayed on self-assembling nanoparticles. Polynucleotide sequences encoding the redesigned immunogens and the nanoparticle vaccines are also provided in the invention. The invention further provides methods of using the vaccine compositions in various therapeutic applications, e.g., for preventing or treating coronaviral infections.

24 Claims, 5 Drawing Sheets

Specification includes a Sequence Listing.

(56) References Cited

OTHER PUBLICATIONS

Keech, et al., First-in-Human Trial of a SARS-CoV-2 Recombinant Spike Protein Nanoparticle Vaccine, medRxiv https://doi.org/10.1101/2020.08.05.20168435, Aug. 2020.

Kirchdoerfer, et al., Stabilized Coronavirus Spikes are Resistant to Conformational Changes Induced by Receptor Recognition or Proteolysis, Scientific Reports, DOI:10.1038/s41598-018-34171-7, 8:15701, 2018.

Lan, et al., Structure of the SARS-CoV-2 Spike Receptor-binding Domain Bound to the ACE2 Receptor, Nature, May 2020, vol. 581, pp. 215-220.

Lurie, et al., Developing Covid-19 Vaccines at Pandemic Speed, New England Journal of Medicine, May 2020, 382: 1969-1973.

Pallesen, et al., Immunogenicity and Structures of a Rationally Designed Prefusion MERS-CoV Spike Antigen, PNAS, Aug. 2017, pp. E7348-E7357.

Park, et al., Structures of MERS-CoV Spike Glycoprotein in Complex with Sialoside Attachment Receptors, Nature Structural & Molecular Biology, Dec. 2019, vol. 26, pp. 1151-1157.

Patel, et al., Intradermal-delivered DNA Vaccine Provides Anamnestic Protection in a Rhesus Macaque SARS-CoV-2 Challenge Model, bioRxiv https://doi.org/10.1101/2020.07.28.225649, Jul. 2020.

Shang, et al., Structural Basis of Receptor Recognition by SARS-CoV-2, Nature, 581(7807): 221-224, 2020.

Smith, et al., Immunogenicity of a DNA Vaccine Candidate for COVID-19, Nature Communications, 11:2601 https://doi.org/10.1038/s41467-020-16505-0. 2020.

Tian, et al., SARS-CoV-2 Spike Glycoprotein Vaccine Candidate NVX-CoV2373 Elicits Immunogenicity in Baboons and Protection in Mice, bioRxiv https://doi.org/10.1101/2020.06.29.178509, Jun. 2020.

Turonova, et al., In situ Structural Analysis of SARS-CoV-2 Spike Reveals Flexibility Mediated by Three Hinges, Science, 10.1126/science.abd5223 (2020).

Walls, et al., Elicitation of Potent Neutralizing Antibody Responses by Designed Protein Nanoparticle Vaccines for SARS-CoV-2, bioRxiv https://doi.org/10.1101/2020.08.11.247395, Aug. 2020.

Walls, et al., Structure, Function, and Antigenicity of the SARSCoV-2 Spike Glycoprotein, Cell 180, pp. 281-292, Apr. 2020.

Wrapp, et al., Cryo-EM Structure of the 2019-nCoV Spike in the Prefusion Conformation, Science 367, pp. 1260-1263, Mar. 2020.

Wrapp, et al., Structural Basis for Potent Neutralization of Betacoronaviruses by Single-Domain Camelid Antibodies, Cell 181, pp. 1004-1015, May 2020.

Yan, et al., Structural Basis for the Recognition of SARS-CoV-2 by Full-length Human ACE2, Science 367, pp. 1444-1446, Mar. 2020.

Yao, et al., Molecular Architecture of the SARS-CoV-2 Virus, Cell 183, https://doi.org/10.1016/j.cell.2020.09.018, 2020.

Yu, et al., DNA Vaccine Protection Against SARS-CoV-2 in Rhesus Macaques, Science, 10.1126/science.abc6284 (2020).

Yuan, et al., Cryo-EM Structures of MERS-CoV and SARS-CoV Spike Glycoproteins Reveal the Dynamic Receptor Binding Domains, Nature Communications, 8:15092, Apr. 2017.

Yuan, et al., A Highly Conserved Cryptic Epitope in the Receptor-binding Domains of SARS-CoV-2 and SARS-CoV, Science, 10.1126/science.abb7269 (2020).

Yuan, et al., Structural Basis of a Shared Antibody Response to SARS-CoV-2, Science 369, pp. 1119-1123, Aug. 2020.

Yurkovetskiy, et al., Structural and Functional Analysis of the D614G SARS-CoV-2 Spike Protein Variant, Cell 183, https://doi.org/10.1016/j.cell.2020.09.032, 2020.

Zhang, et al., Versatile Platform to Incorporate Viral Trimeric Antigens into Self-Assembling Nanoparticle Immunogens, bioRxiv https://doi.org/10.1101/2020.06.11.147496, Jun. 2020.

Lv et al., Cross-reactive Antibody Response between SARS-CoV-2 and SARS-Cov Infections. Cell Reports 31, 107725, 2020.

\* cited by examiner

FIG. 3

Mouse serum ELISA ED$_{50}$ values

| Coating antigen | SARS-CoV-2 vaccine antigen | w2 M1 | M2 | M3 | M4 | M5 | w5 M1 | M2 | M3 | M4 | M5 | w8 M1 | M2 | M3 | M4 | M5 | w11 M1 | M2 | M3 | M4 | M5 |
|---|---|---|---|---|---|---|---|---|---|---|---|---|---|---|---|---|---|---|---|---|---|
| SARS-CoV-1 S2P-5GS-foldon | S2P-5GS-1TD0 | 337 | 378 | 438 | 92 | 166 | 8229 | 14598 | 15271 | 11029 | 15730 | 31346 | 19923 | 49495 | 20899 | 27362 | 87963 | 74675 | 105473 | 61814 | 98729 |
| | S2GΔHR2-5GS-1TD0 | 160 | 300 | 42 | 264 | <20 | 29889 | 9934 | 11211 | 21972 | 2225 | 54736 | 33977 | 31597 | 69701

FIG. 4

Mouse serum neutralization ID$_{50}$ values

Pseudovirus SARS-CoV-1-pp:

| SARS-CoV-2 vaccine antigen | W2 M1 | W2 M2 | W2 M3 | W2 M4 | W2 M5 | W5 M1 | W5 M2 | W5 M3 | W5 M4 | W5 M5 | W8 M1 | W8 M2 | W8 M3 | W8 M4 | W8 M5 | W11 M1 | W11 M2 | W11 M3 | W11 M4 | W11 M5 |
|---|---|---|---|---|---|---|---|---|---|---|---|---|---|---|---|---|---|---|---|---|
| S2P-5GS-1TD0 | <100 | <100 | <100 | <100 | <100 | 405 | 444 | 1032 | 270 | 501 | 776.6 | 1062 | 3410 | 1121 | 6783 | 2588 | 2431 | 9374 | 1074 | 1806 |
| S2GΔHR2-5GS-1TD0 | <100 | <100 | <100 | <100 | <100 | 17433 | 3960 | 2747 | 5170 | <100 | 13124 | 7579 | 3443 | 7902 | 221 | 11228 | 4377 | 3271 | 6009 | 4176 |
| S2GΔHR2-5GS-FR | <100 | <100 | <100 | <100 | <100 | 4152 | 6773 | 5414 | 10007 | 3527 | 3735 | 5968 | 6443 | 7605 | 3872 | 3384 | 4103 | 5704 | 8194 | 2897 |
| S2GΔHR2-5GS-E2p-L4P | <100 | <100 | <100 | <100 | <100 | 7954 | 10197 | 23509 | 17140 | 2915 | 7676 | 18213 | 17917 | 19538 | 4017 | 9170 | 5651 | 13334 | 12484 | 4799 |
| S2GΔHR2-10GS-I3-01v9-L7P | 278 | 330 | 247 | 486 | 417 | 8250 | 11666 | 6695 | 15034 | 8694 | 14174 | 14888 | 22024 | 21474 | 9393 | | | | | |

Pseudovirus SARS-CoV-2-pp:

| SARS-CoV-2 vaccine antigen | w2 M1 | w2 M2 | w2 M3 | w2 M4 | w2 M5 | w5 M1 | w5 M2 | w5 M3 | w5 M4 | w5 M5 | w8 M1 | w8 M2 | w8 M3 | w8 M4 | w8 M5 | w11 M1 | w11 M2 | w11 M3 | w11 M4 | w11 M5 |
|---|---|---|---|---|---|---|---|---|---|---|---|---|---|---|---|---|---|---|---|---|
| S2P-5GS-1TD0 | <100 | <100 | <100 | <100 | <100 | 1050 | 787 | 1524 | 369 | 667 | 3515 | 3169 | 2897 | 1141 | 1683 | 11358 | 7358 | 10878 | 10723 | 7868 |
| S2GΔHR2-5GS-1TD0 | <100 | <100 | <100 | <100 | <100 | 18419 | 3271 | 3238 | 4382 | 263 | 12641 | 4656 | 6148 | 9660 | 1707 | 27622 | 13489 | 18860 | 31117 | 4173 |
| S2GΔHR2-5GS-FR | <100 | <100 | <100 | <100 | <100 | 3065 | 6659 | 8044 | 5164 | 1072 | 4156 | 12681 | 14238 | 6453 | 1827 | 11054 | 31423 | 26556 | 19137 | 6777 |
| S2GΔHR2-5GS-E2p-L4P | <100 | <100 | <100 | <100 | <100 | 5778 | 11650 | 7370 | 16399 | 977 | 8613 | 14120 | 5999 | 19054 | 4733 | 13126 | 28298 | 18219 | 77734 | 12356 |
| S2GΔHR2-10GS-I3-01v9-L7P | <100 | <100 | <100 | <100 | <100 | 5465 | 5151 | 1440 | 6831 | 4722 | 14684 | 22060 | 12830 | 23608 | 13575 | | | | | |

SEQUENCE LISTING

```
<160> NUMBER OF SEQ ID NOS: 40

<210> SEQ ID NO 1
<211> LENGTH: 1190
<212> TYPE: PRT
<213> ORGANISM: Artificial sequence
```

<220> FEATURE:
<223> OTHER INFORMATION: Synthetic sequence

<400> SEQUENCE: 1

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400
```

-continued

```
Gln Thr Gly Val Ile Ala Asp Tyr Asn Tyr Lys Leu Pro Asp Asp Phe
                    405                 410                 415
Met Gly Cys Val Leu Ala Trp Asn Thr Arg Asn Ile Asp Ala Thr Ser
            420                 425                 430
Thr Gly Asn Tyr Asn Tyr Lys Tyr Arg Tyr Leu Arg His Gly Lys Leu
        435                 440                 445
Arg Pro Phe Glu Arg Asp Ile Ser Asn Val Pro Phe Ser Pro Asp Gly
450                 455                 460
Lys Pro Cys Thr Pro Pro Ala Leu Asn Cys Tyr Trp Pro Leu Asn Asp
465                 470                 475                 480
Tyr Gly Phe Tyr Thr Thr Thr Gly Ile Gly Tyr Gln Pro Tyr Arg Val
                485                 490                 495
Val Val Leu Ser Phe Glu Leu Leu Asn Ala Pro Ala Thr Val Cys Gly
            500                 505                 510
Pro Lys Leu Ser Thr Asp Leu Ile Lys Asn Gln Cys Val Asn Phe Asn
        515                 520                 525
Phe Asn Gly Leu Thr Gly Thr Gly Val Leu Thr Pro Ser Ser Lys Arg
530                 535                 540
Phe Gln Pro Phe Gln Gln Phe Gly Arg Asp Val Ser Asp Phe Thr Asp
545                 550                 555                 560
Ser Val Arg Asp Pro Lys Thr Ser Glu Ile Leu Asp Ile Ser Pro Cys
                565                 570                 575
Ala Phe Gly Gly Val Ser Val Ile Thr Pro Gly Thr Asn Ala Ser Ser
            580                 585                 590
Glu Val Ala Val Leu Tyr Gln Asp Val Asn Cys Thr Asp Val Ser Thr
        595                 600                 605
Ala Ile His Ala Asp Gln Leu Thr Pro Ala Trp Arg Ile Tyr Ser Thr
610                 615                 620
Gly Asn Asn Val Phe Gln Thr Gln Ala Gly Cys Leu Ile Gly Ala Glu
625                 630                 635                 640
His Val Asp Thr Ser Tyr Glu Cys Asp Ile Pro Ile Gly Ala Gly Ile
                645                 650                 655
Cys Ala Ser Tyr His Thr Val Ser Leu Leu Arg Ser Thr Ser Gln Lys
            660                 665                 670
Ser Ile Val Ala Tyr Thr Met Ser Leu Gly Ala Asp Ser Ser Ile Ala
        675                 680                 685
Tyr Ser Asn Asn Thr Ile Ala Ile Pro Thr Asn Phe Ser Ile Ser Ile
690                 695                 700
Thr Thr Glu Val Met Pro Val Ser Met Ala Lys Thr Ser Val Asp Cys
705                 710                 715                 720
Asn Met Tyr Ile Cys Gly Asp Ser Thr Glu Cys Ala Asn Leu Leu Leu
                725                 730                 735
Gln Tyr Gly Ser Phe Cys Thr Gln Leu Asn Arg Ala Leu Ser Gly Ile
            740                 745                 750
Ala Ala Glu Gln Asp Arg Asn Thr Arg Glu Val Phe Ala Gln Val Lys
        755                 760                 765
Gln Met Tyr Lys Thr Pro Thr Leu Lys Tyr Phe Gly Gly Phe Asn Phe
770                 775                 780
Ser Gln Ile Leu Pro Asp Pro Leu Lys Pro Thr Lys Arg Ser Phe Ile
785                 790                 795                 800
Glu Asp Leu Leu Phe Asn Lys Val Thr Leu Ala Asp Ala Gly Phe Met
                805                 810                 815
```

-continued

```
Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
        850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys Met Ser Glu Cys Val  Leu Gly Gln Ser Lys  Arg Val Asp
       1010                1015                1020

Phe Cys Gly Lys Gly Tyr His  Leu Met Ser Phe Pro  Gln Ala Ala
       1025                1030                1035

Pro His Gly Val Val Phe Leu  His Val Thr Tyr Val  Pro Ser Gln
       1040                1045                1050

Glu Arg Asn Phe Thr Thr Ala  Pro Ala Ile Cys His  Glu Gly Lys
       1055                1060                1065

Ala Tyr Phe Pro Arg Glu Gly  Val Phe Val Phe Asn  Gly Thr Ser
       1070                1075                1080

Trp Phe Ile Thr Gln Arg Asn  Phe Phe Ser Pro Gln  Ile Ile Thr
       1085                1090                1095

Thr Asp Asn Thr Phe Val Ser  Gly Asn Cys Asp Val  Val Ile Gly
       1100                1105                1110

Ile Ile Asn Asn Thr Val Tyr  Asp Pro Leu Gln Pro  Glu Leu Asp
       1115                1120                1125

Ser Phe Lys Glu Glu Leu Asp  Lys Tyr Phe Lys Asn  His Thr Ser
       1130                1135                1140

Pro Asp Val Asp Leu Gly Asp  Ile Ser Gly Ile Asn  Ala Ser Val
       1145                1150                1155

Val Asn Ile Gln Lys Glu Ile  Asp Arg Leu Asn Glu  Val Ala Lys
       1160                1165                1170

Asn Leu Asn Glu Ser Leu Ile  Asp Leu Gln Glu Leu  Gly Lys Tyr
       1175                1180                1185

Glu Gln
   1190

<210> SEQ ID NO 2
<211> LENGTH: 1291
<212> TYPE: PRT
```

<213> ORGANISM: Artificial sequence
<220> FEATURE:
<223> OTHER INFORMATION: Synthetic sequence

<400> SEQUENCE: 2

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys

```
                385                 390                 395                 400
        Arg Leu Val Phe Thr Asn Cys Asn Tyr Asn Leu Thr Lys Leu Leu Ser
                        405                 410                 415

Leu Phe Ser Val Asn Asp Phe Thr Cys Ser Gln Ile Ser Pro Ala Ala
                        420                 425                 430

Ile Ala Ser Asn Cys Tyr Ser Leu Ile Leu Asp Tyr Phe Ser Tyr
                        435                 440                 445

Pro Leu Ser Met Lys Ser Asp Leu Ser Val Ser Ser Ala Gly Pro Ile
                    450                 455                 460

Ser Gln Phe Asn Tyr Lys Gln Ser Phe Ser Asn Pro Thr Cys Leu Ile
        465                 470                 475                 480

Leu Ala Thr Val Pro His Asn Leu Thr Thr Ile Thr Lys Pro Leu Lys
                        485                 490                 495

Tyr Ser Tyr Ile Asn Lys Cys Ser Arg Leu Leu Ser Asp Asp Arg Thr
                        500                 505                 510

Glu Val Pro Gln Leu Val Asn Ala Asn Gln Tyr Ser Pro Cys Val Ser
                        515                 520                 525

Ile Val Pro Ser Thr Val Trp Glu Asp Gly Asp Tyr Tyr Arg Lys Gln
                    530                 535                 540

Leu Ser Pro Leu Glu Gly Gly Gly Trp Leu Val Ala Ser Gly Ser Thr
        545                 550                 555                 560

Val Ala Met Thr Glu Gln Leu Gln Met Gly Phe Gly Ile Thr Val Gln
                        565                 570                 575

Tyr Gly Thr Asp Thr Asn Ser Val Cys Pro Lys Leu Glu Phe Ala Asn
                        580                 585                 590

Asp Thr Lys Ile Ala Ser Gln Leu Gly Asn Cys Val Glu Tyr Ser Leu
                        595                 600                 605

Tyr Gly Val Ser Gly Arg Gly Val Phe Gln Asn Cys Thr Ala Val Gly
                    610                 615                 620

Val Arg Gln Gln Arg Phe Val Tyr Asp Ala Tyr Gln Asn Leu Val Gly
        625                 630                 635                 640

Tyr Tyr Ser Asp Asp Gly Asn Tyr Tyr Cys Leu Arg Ala Cys Val Ser
                        645                 650                 655

Val Pro Val Ser Val Ile Tyr Asp Lys Glu Thr Lys Thr His Ala Thr
                        660                 665                 670

Leu Phe Gly Ser Val Ala Cys Glu His Ile Ser Ser Thr Met Ser Gln
                        675                 680                 685

Tyr Ser Arg Ser Thr Arg Ser Met Leu Lys Arg Arg Asp Ser Thr Tyr
                    690                 695                 700

Gly Pro Leu Gln Thr Pro Val Gly Cys Val Leu Gly Leu Val Asn Ser
        705                 710                 715                 720

Ser Leu Phe Val Glu Asp Cys Lys Leu Pro Leu Gly Gln Ser Leu Cys
                        725                 730                 735

Ala Leu Pro Asp Thr Pro Ser Thr Leu Thr Pro Arg Ser Val Arg Ser
                        740                 745                 750

Val Pro Gly Glu Met Arg Leu Ala Ser Ile Ala Phe Asn His Pro Ile
                        755                 760                 765

Gln Val Asp Gln Leu Asn Ser Ser Tyr Phe Lys Leu Ser Ile Pro Thr
                    770                 775                 780

Asn Phe Ser Phe Gly Val Thr Gln Glu Tyr Ile Gln Thr Thr Ile Gln
        785                 790                 795                 800

Lys Val Thr Val Asp Cys Lys Gln Tyr Val Cys Asn Gly Phe Gln Lys
                        805                 810                 815
```

-continued

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
            930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe Gln Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

-continued

```
Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr
    1280                1285                1290

<210> SEQ ID NO 3
<211> LENGTH: 1208
<212> TYPE: PRT
<213> ORGANISM: Artificial sequence
<220> FEATURE:
<223> OTHER INFORMATION: Synthetic sequence

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285
```

-continued

```
Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
```

```
            705                 710                 715                 720
        Ser Val Thr Thr Glu Ile Leu Pro Val Ser Met Thr Lys Thr Ser Val
                        725                 730                 735
        Asp Cys Thr Met Tyr Ile Cys Gly Asp Ser Thr Glu Cys Ser Asn Leu
                        740                 745                 750
        Leu Leu Gln Tyr Gly Ser Phe Cys Thr Gln Leu Asn Arg Ala Leu Thr
                        755                 760                 765
        Gly Ile Ala Val Glu Gln Asp Lys Asn Thr Gln Glu Val Phe Ala Gln
                        770                 775                 780
        Val Lys Gln Ile Tyr Lys Thr Pro Pro Ile Lys Asp Phe Gly Gly Phe
        785                 790                 795                 800
        Asn Phe Ser Gln Ile Leu Pro Asp Pro Ser Lys Pro Ser Lys Arg Ser
                        805                 810                 815
        Phe Ile Glu Asp Leu Leu Phe Asn Lys Val Thr Leu Ala Asp Ala Gly
                        820                 825                 830
        Phe Ile Lys Gln Tyr Gly Asp Cys Leu Gly Asp Ile Ala Ala Arg Asp
                        835                 840                 845
        Leu Ile Cys Ala Gln Lys Phe Asn Gly Leu Thr Val Leu Pro Pro Leu
                        850                 855                 860
        Leu Thr Asp Glu Met Ile Ala Gln Tyr Thr Ser Ala Leu Leu Ala Gly
        865                 870                 875                 880
        Thr Ile Thr Ser Gly Trp Thr Phe Gly Ala Gly Ala Ala Leu Gln Ile
                        885                 890                 895
        Pro Phe Ala Met Gln Met Ala Tyr Arg Phe Asn Gly Ile Gly Val Thr
                        900                 905                 910
        Gln Asn Val Leu Tyr Glu Asn Gln Lys Leu Ile Ala Asn Gln Phe Asn
                        915                 920                 925
        Ser Ala Ile Gly Lys Ile Gln Asp Ser Leu Ser Ser Thr Ala Ser Ala
                        930                 935                 940
        Leu Gly Lys Leu Gln Asp Val Val Asn Gln Asn Ala Gln Ala Leu Asn
        945                 950                 955                 960
        Thr Leu Val Lys Gln Leu Ser Ser Asn Phe Gly Ala Ile Ser Ser Val
                        965                 970                 975
        Leu Asn Asp Ile Leu Ser Arg Leu Asp Lys Val Glu Ala Glu Val Gln
                        980                 985                 990
        Ile Asp Arg Leu Ile Thr Gly Arg  Leu Gln Ser Leu Gln  Thr Tyr Val
                        995                1000                1005
        Thr Gln Gln Leu Ile Arg Ala  Ala Glu Ile Arg Ala  Ser Ala Asn
                1010                1015                1020
        Leu Ala Ala Thr Lys Met Ser  Glu Cys Val Leu Gly  Gln Ser Lys
                1025                1030                1035
        Arg Val Asp Phe Cys Gly Lys  Gly Tyr His Leu Met  Ser Phe Pro
                1040                1045                1050
        Gln Ser Ala Pro His Gly Val  Val Phe Leu His Val  Thr Tyr Val
                1055                1060                1065
        Pro Ala Gln Glu Lys Asn Phe  Thr Thr Ala Pro Ala  Ile Cys His
                1070                1075                1080
        Asp Gly Lys Ala His Phe Pro  Arg Glu Gly Val Phe  Val Ser Asn
                1085                1090                1095
        Gly Thr His Trp Phe Val Thr  Gln Arg Asn Phe Tyr  Glu Pro Gln
                1100                1105                1110
        Ile Ile Thr Thr Asp Asn Thr  Phe Val Ser Gly Asn  Cys Asp Val
                1115                1120                1125
```

```
Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln
    1205

<210> SEQ ID NO 4
<211> LENGTH: 202
<212> TYPE: PRT
<213> ORGANISM: Artificial sequence
<220> FEATURE:
<223> OTHER INFORMATION: Synthetic sequence

<400> SEQUENCE: 4

Pro Asn Ile Thr Asn Leu Cys Pro Phe Gly Glu Val Phe Asn Ala Thr
1               5                   10                  15

Lys Phe Pro Ser Val Tyr Ala Trp Glu Arg Lys Lys Ile Ser Asn Cys
            20                  25                  30

Val Ala Asp Tyr Ser Val Leu Tyr Asn Ser Thr Phe Phe Ser Thr Phe
        35                  40                  45

Lys Cys Tyr Gly Val Ser Ala Thr Lys Leu Asn Asp Leu Cys Phe Ser
    50                  55                  60

Asn Val Tyr Ala Asp Ser Phe Val Lys Gly Asp Asp Val Arg Gln
65                  70                  75              80

Ile Ala Pro Gly Gln Thr Gly Val Ile Ala Asp Tyr Asn Tyr Lys Leu
                85                  90                  95

Pro Asp Asp Phe Met Gly Cys Val Leu Ala Trp Asn Thr Arg Asn Ile
            100                 105                 110

Asp Ala Thr Ser Thr Gly Asn Tyr Asn Tyr Lys Tyr Arg Tyr Leu Arg
        115                 120                 125

His Gly Lys Leu Arg Pro Phe Glu Arg Asp Ile Ser Asn Val Pro Phe
    130                 135                 140

Ser Pro Asp Gly Lys Pro Cys Thr Pro Pro Ala Leu Asn Cys Tyr Trp
145                 150                 155                 160

Pro Leu Asn Asp Tyr Gly Phe Tyr Thr Thr Thr Gly Ile Gly Tyr Gln
                165                 170                 175

Pro Tyr Arg Val Val Val Leu Ser Phe Glu Leu Leu Asn Ala Pro Ala
            180                 185                 190

Thr Val Cys Gly Pro Lys Leu Ser Thr Asp
        195                 200

<210> SEQ ID NO 5
<211> LENGTH: 206
<212> TYPE: PRT
<213> ORGANISM: Artificial sequence
<220> FEATURE:
<223> OTHER INFORMATION: Synthetic sequence

<400> SEQUENCE: 5

Glu Cys Asp Phe Ser Pro Leu Leu Ser Gly Thr Pro Pro Gln Val Tyr
```

```
              1               5                  10                 15
Asn Phe Lys Arg Leu Val Phe Thr Asn Cys Asn Tyr Asn Leu Thr Lys
             20                  25                 30

Leu Leu Ser Leu Phe Ser Val Asn Asp Phe Thr Cys Ser Gln Ile Ser
             35                  40                 45

Pro Ala Ile Ala Ser Asn Cys Tyr Ser Ser Leu Ile Leu Asp Tyr
         50                  55                 60

Phe Ser Tyr Pro Leu Ser Met Lys Ser Asp Leu Ser Val Ser Ser Ala
65                   70                  75                 80

Gly Pro Ile Ser Gln Phe Asn Tyr Lys Gln Ser Phe Ser Asn Pro Thr
                 85                  90                 95

Cys Leu Ile Leu Ala Thr Val Pro His Asn Leu Thr Thr Ile Thr Lys
                100                 105                110

Pro Leu Lys Tyr Ser Tyr Ile Asn Lys Cys Ser Arg Leu Leu Ser Asp
                115                 120                125

Asp Arg Thr Glu Val Pro Gln Leu Val Asn Ala Asn Gln Tyr Ser Pro
       130                 135                 140

Cys Val Ser Ile Val Pro Ser Thr Val Trp Glu Asp Gly Asp Tyr Tyr
145                 150                 155                160

Arg Lys Gln Leu Ser Pro Leu Glu Gly Gly Trp Leu Val Ala Ser
                    165                 170                 175

Gly Ser Thr Val Ala Met Thr Glu Gln Leu Gln Met Gly Phe Gly Ile
            180                 185                 190

Thr Val Gln Tyr Gly Thr Asp Thr Asn Ser Val Cys Pro Lys
        195                 200                 205

<210> SEQ ID NO 6
<211> LENGTH: 203
<212> TYPE: PRT
<213> ORGANISM: Artificial sequence
<220> FEATURE:
<223> OTHER INFORMATION: Synthetic sequence

<400> SEQUENCE: 6

Pro Asn Ile Thr Asn Leu Cys Pro Phe Gly Glu Val Phe Asn Ala Thr
1               5                  10                 15

Arg Phe Ala Ser Val Tyr Ala Trp Asn Arg Lys Arg Ile Ser Asn Cys
             20                  25                 30

Val Ala Asp Tyr Ser Val Leu Tyr Asn Ser Ala Ser Phe Ser Thr Phe
             35                  40                 45

Lys Cys Tyr Gly Val Ser Pro Thr Lys Leu Asn Asp Leu Cys Phe Thr
         50                  55                 60

Asn Val Tyr Ala Asp Ser Phe Val Ile Arg Gly Asp Glu Val Arg Gln
65                   70                  75                 80

Ile Ala Pro Gly Gln Thr Gly Lys Ile Ala Asp Tyr Asn Tyr Lys Leu
                 85                  90                 95

Pro Asp Asp Phe Thr Gly Cys Val Ile Ala Trp Asn Ser Asn Asn Leu
                100                 105                110

Asp Ser Lys Val Gly Gly Asn Tyr Asn Tyr Leu Tyr Arg Leu Phe Arg
                115                 120                125

Lys Ser Asn Leu Lys Pro Phe Glu Arg Asp Ile Ser Thr Glu Ile Tyr
       130                 135                 140

Gln Ala Gly Ser Thr Pro Cys Asn Gly Val Glu Gly Phe Asn Cys Tyr
145                 150                 155                160

Phe Pro Leu Gln Ser Tyr Gly Phe Gln Pro Thr Asn Gly Val Gly Tyr
```

-continued

```
                165                 170                 175
Gln Pro Tyr Arg Val Val Leu Ser Phe Glu Leu His Ala Pro
            180                 185                 190

Ala Thr Val Cys Gly Pro Lys Lys Ser Thr Asn
            195                 200

<210> SEQ ID NO 7
<211> LENGTH: 1177
<212> TYPE: PRT
<213> ORGANISM: Artificial sequence
<220> FEATURE:
<223> OTHER INFORMATION: Synthetic sequence

<400> SEQUENCE: 7

Ser Asp Leu Asp Arg Cys Thr Thr Phe Asp Asp Val Gln Ala Pro Asn
1               5                   10                  15

Tyr Thr Gln His Thr Ser Ser Met Arg Gly Val Tyr Tyr Pro Asp Glu
                20                  25                  30

Ile Phe Arg Ser Asp Thr Leu Tyr Leu Thr Gln Asp Leu Phe Leu Pro
            35                  40                  45

Phe Tyr Ser Asn Val Thr Gly Phe His Thr Ile Asn His Thr Phe Gly
50                  55                  60

Asn Pro Val Ile Pro Phe Lys Asp Gly Ile Tyr Phe Ala Ala Thr Glu
65                  70                  75                  80

Lys Ser Asn Val Val Arg Gly Trp Val Phe Gly Ser Thr Met Asn Asn
                85                  90                  95

Lys Ser Gln Ser Val Ile Ile Asn Asn Ser Thr Asn Val Val Ile
            100                 105                 110

Arg Ala Cys Asn Phe Glu Leu Cys Asp Asn Pro Phe Phe Ala Val Ser
            115                 120                 125

Lys Pro Met Gly Thr Gln Thr His Thr Met Ile Phe Asp Asn Ala Phe
        130                 135                 140

Asn Cys Thr Phe Glu Tyr Ile Ser Asp Ala Phe Ser Leu Asp Val Ser
145                 150                 155                 160

Glu Lys Ser Gly Asn Phe Lys His Leu Arg Glu Phe Val Phe Lys Asn
                165                 170                 175

Lys Asp Gly Phe Leu Tyr Val Tyr Lys Gly Tyr Gln Pro Ile Asp Val
            180                 185                 190

Val Arg Asp Leu Pro Ser Gly Phe Asn Thr Leu Lys Pro Ile Phe Lys
        195                 200                 205

Leu Pro Leu Gly Ile Asn Ile Thr Asn Phe Arg Ala Ile Leu Thr Ala
    210                 215                 220

Phe Ser Pro Ala Gln Asp Ile Trp Gly Thr Ser Ala Ala Ala Tyr Phe
225                 230                 235                 240

Val Gly Tyr Leu Lys Pro Thr Thr Phe Met Leu Lys Tyr Asp Glu Asn
                245                 250                 255

Gly Thr Ile Thr Asp Ala Val Asp Cys Ser Gln Asn Pro Leu Ala Glu
            260                 265                 270

Leu Lys Cys Ser Val Lys Ser Phe Glu Ile Asp Lys Gly Ile Tyr Gln
        275                 280                 285

Thr Ser Asn Phe Arg Val Val Pro Ser Gly Asp Val Val Arg Phe Pro
    290                 295                 300

Asn Ile Thr Asn Leu Cys Pro Phe Gly Glu Val Phe Asn Ala Thr Lys
305                 310                 315                 320

Phe Pro Ser Val Tyr Ala Trp Glu Arg Lys Lys Ile Ser Asn Cys Val
```

```
                    325                 330                 335
Ala Asp Tyr Ser Val Leu Tyr Asn Ser Thr Phe Phe Ser Thr Phe Lys
                340                 345                 350
Cys Tyr Gly Val Ser Ala Thr Lys Leu Asn Asp Leu Cys Phe Ser Asn
                355                 360                 365
Val Tyr Ala Asp Ser Phe Val Lys Gly Asp Asp Val Arg Gln Ile
            370                 375                 380
Ala Pro Gly Gln Thr Gly Val Ile Ala Asp Tyr Asn Tyr Lys Leu Pro
385                 390                 395                 400
Asp Asp Phe Met Gly Cys Val Leu Ala Trp Asn Thr Arg Asn Ile Asp
                405                 410                 415
Ala Thr Ser Thr Gly Asn Tyr Asn Tyr Lys Tyr Arg Tyr Leu Arg His
                420                 425                 430
Gly Lys Leu Arg Pro Phe Glu Arg Asp Ile Ser Asn Val Pro Phe Ser
                435                 440                 445
Pro Asp Gly Lys Pro Cys Thr Pro Pro Ala Leu Asn Cys Tyr Trp Pro
450                 455                 460
Leu Asn Asp Tyr Gly Phe Tyr Thr Thr Thr Gly Ile Gly Tyr Gln Pro
465                 470                 475                 480
Tyr Arg Val Val Val Leu Ser Phe Glu Leu Leu Asn Ala Pro Ala Thr
                485                 490                 495
Val Cys Gly Pro Lys Leu Ser Thr Asp Leu Ile Lys Asn Gln Cys Val
                500                 505                 510
Asn Phe Asn Phe Asn Gly Leu Thr Gly Thr Gly Val Leu Thr Pro Ser
                515                 520                 525
Ser Lys Arg Phe Gln Pro Phe Gln Gln Phe Gly Arg Asp Val Ser Asp
                530                 535                 540
Phe Thr Asp Ser Val Arg Asp Pro Lys Thr Ser Glu Ile Leu Asp Ile
545                 550                 555                 560
Ser Pro Cys Ala Phe Gly Gly Val Ser Val Ile Thr Pro Gly Thr Asn
                565                 570                 575
Ala Ser Ser Glu Val Ala Val Leu Tyr Gln Asp Val Asn Cys Thr Asp
                580                 585                 590
Val Ser Thr Ala Ile His Ala Asp Gln Leu Thr Pro Ala Trp Arg Ile
                595                 600                 605
Tyr Ser Thr Gly Asn Asn Val Phe Gln Thr Gln Ala Gly Cys Leu Ile
                610                 615                 620
Gly Ala Glu His Val Asp Thr Ser Tyr Glu Cys Asp Ile Pro Ile Gly
625                 630                 635                 640
Ala Gly Ile Cys Ala Ser Tyr His Thr Val Ser Leu Leu Arg Ser Thr
                645                 650                 655
Ser Gln Lys Ser Ile Val Ala Tyr Thr Met Ser Leu Gly Ala Asp Ser
                660                 665                 670
Ser Ile Ala Tyr Ser Asn Asn Thr Ile Ala Ile Pro Thr Asn Phe Ser
                675                 680                 685
Ile Ser Ile Thr Thr Glu Val Met Pro Val Ser Met Ala Lys Thr Ser
                690                 695                 700
Val Asp Cys Asn Met Tyr Ile Cys Gly Asp Ser Thr Glu Cys Ala Asn
705                 710                 715                 720
Leu Leu Leu Gln Tyr Gly Ser Phe Cys Thr Gln Leu Asn Arg Ala Leu
                725                 730                 735
Ser Gly Ile Ala Ala Glu Gln Asp Arg Asn Thr Arg Glu Val Phe Ala
                740                 745                 750
```

```
Gln Val Lys Gln Met Tyr Lys Thr Pro Thr Leu Lys Tyr Phe Gly Gly
            755                 760                 765

Phe Asn Phe Ser Gln Ile Leu Pro Asp Pro Leu Lys Pro Thr Lys Arg
    770                 775                 780

Ser Phe Ile Glu Asp Leu Leu Phe Asn Lys Val Thr Leu Ala Asp Ala
785                 790                 795                 800

Gly Phe Met Lys Gln Tyr Gly Glu Cys Leu Gly Asp Ile Asn Ala Arg
                805                 810                 815

Asp Leu Ile Cys Ala Gln Lys Phe Asn Gly Leu Thr Val Leu Pro Pro
                820                 825                 830

Leu Leu Thr Asp Asp Met Ile Ala Ala Tyr Thr Ala Ala Leu Val Ser
            835                 840                 845

Gly Thr Ala Thr Ala Gly Trp Thr Phe Gly Ala Gly Ala Ala Leu Gln
850                 855                 860

Ile Pro Phe Ala Met Gln Met Ala Tyr Arg Phe Asn Gly Ile Gly Val
865                 870                 875                 880

Thr Gln Asn Val Leu Tyr Glu Asn Gln Lys Gln Ile Ala Asn Gln Phe
                885                 890                 895

Asn Lys Ala Ile Ser Gln Ile Gln Glu Ser Leu Thr Thr Thr Ser Thr
                900                 905                 910

Ala Leu Gly Lys Leu Gln Asp Val Val Asn Gln Asn Ala Gln Ala Leu
            915                 920                 925

Asn Thr Leu Val Lys Gln Leu Ser Ser Asn Phe Gly Ala Ile Ser Ser
930                 935                 940

Val Leu Asn Asp Ile Leu Ser Arg Leu Asp Lys Val Glu Ala Glu Val
945                 950                 955                 960

Gln Ile Asp Arg Leu Ile Thr Gly Arg Leu Gln Ser Leu Gln Thr Tyr
                965                 970                 975

Val Thr Gln Gln Leu Ile Arg Ala Ala Glu Ile Arg Ala Ser Ala Asn
            980                 985                 990

Leu Ala Ala Thr Lys Met Ser Glu  Cys Val Leu Gly Gln  Ser Lys Arg
            995                 1000                1005

Val Asp  Phe Cys Gly Lys Gly  Tyr His Leu Met Ser  Phe Pro Gln
    1010                1015                1020

Ala Ala  Pro His Gly Val Val  Phe Leu His Val Thr  Tyr Val Pro
    1025                1030                1035

Ser Gln  Glu Arg Asn Phe Thr  Thr Ala Pro Ala Ile  Cys His Glu
    1040                1045                1050

Gly Lys  Ala Tyr Phe Pro Arg  Glu Gly Val Phe Val  Phe Asn Gly
    1055                1060                1065

Thr Ser  Trp Phe Ile Thr Gln  Arg Asn Phe Phe Ser  Pro Gln Ile
    1070                1075                1080

Ile Thr  Thr Asp Asn Thr Phe  Val Ser Gly Asn Cys  Asp Val Val
    1085                1090                1095

Ile Gly  Ile Ile Asn Asn Thr  Val Tyr Asp Pro Leu  Gln Pro Glu
    1100                1105                1110

Leu Asp  Ser Phe Lys Glu Glu  Leu Asp Lys Tyr Phe  Lys Asn His
    1115                1120                1125

Thr Ser  Pro Asp Val Asp Leu  Gly Asp Ile Ser Gly  Ile Asn Ala
    1130                1135                1140

Ser Val  Val Asn Ile Gln Lys  Glu Ile Asp Arg Leu  Asn Glu Val
    1145                1150                1155
```

```
Ala Lys Asn Leu Asn Glu Ser  Leu Ile Asp Leu Gln  Glu Leu Gly
    1160                1165              1170

Lys Tyr  Glu Gln
    1175
```

<210> SEQ ID NO 8
<211> LENGTH: 13
<212> TYPE: PRT
<213> ORGANISM: Artificial sequence
<220> FEATURE:
<223> OTHER INFORMATION: Synthetic sequence

<400> SEQUENCE: 8

```
Met Phe Ile Phe Leu Leu Phe Leu Thr Leu Thr Ser Gly
1               5                   10
```

<210> SEQ ID NO 9
<211> LENGTH: 59
<212> TYPE: PRT
<213> ORGANISM: Artificial sequence
<220> FEATURE:
<223> OTHER INFORMATION: Synthetic sequence

<400> SEQUENCE: 9

```
Glu Glu Leu Asp Lys Tyr Phe Lys Asn His Thr Ser Pro Asp Val Asp
1               5                   10                  15

Leu Gly Asp Ile Ser Gly Ile Asn Ala Ser Val Val Asn Ile Gln Lys
            20                  25                  30

Glu Ile Asp Arg Leu Asn Glu Val Ala Lys Asn Leu Asn Glu Ser Leu
        35                  40                  45

Ile Asp Leu Gln Glu Leu Gly Lys Tyr Glu Gln
        50                  55
```

<210> SEQ ID NO 10
<211> LENGTH: 11
<212> TYPE: PRT
<213> ORGANISM: Artificial sequence
<220> FEATURE:
<223> OTHER INFORMATION: Synthetic sequence

<400> SEQUENCE: 10

```
Asp Pro Leu Gln Pro Glu Leu Asp Ser Phe Lys
1               5                   10
```

<210> SEQ ID NO 11
<211> LENGTH: 1274
<212> TYPE: PRT
<213> ORGANISM: Artificial sequence
<220> FEATURE:
<223> OTHER INFORMATION: Synthetic sequence

<400> SEQUENCE: 11

```
Tyr Val Asp Val Gly Pro Asp Ser Val Lys Ser Ala Cys Ile Glu Val
1               5                   10                  15

Asp Ile Gln Gln Thr Phe Phe Asp Lys Thr Trp Pro Arg Pro Ile Asp
            20                  25                  30

Val Ser Lys Ala Asp Gly Ile Ile Tyr Pro Gln Gly Arg Thr Tyr Ser
        35                  40                  45

Asn Ile Thr Ile Thr Tyr Gln Gly Leu Phe Pro Tyr Gln Gly Asp His
        50                  55                  60

Gly Asp Met Tyr Val Tyr Ser Ala Gly His Ala Thr Gly Thr Thr Pro
65                  70                  75                  80
```

Gln Lys Leu Phe Val Ala Asn Tyr Ser Gln Asp Val Lys Gln Phe Ala
                85                  90                  95

Asn Gly Phe Val Val Arg Ile Gly Ala Ala Asn Ser Thr Gly Thr
            100                 105                 110

Val Ile Ile Ser Pro Ser Thr Ser Ala Thr Ile Arg Lys Ile Tyr Pro
            115                 120                 125

Ala Phe Met Leu Gly Ser Ser Val Gly Asn Phe Ser Asp Gly Lys Met
130                 135                 140

Gly Arg Phe Phe Asn His Thr Leu Val Leu Leu Pro Asp Gly Cys Gly
145                 150                 155                 160

Thr Leu Leu Arg Ala Phe Tyr Cys Ile Leu Glu Pro Arg Ser Gly Asn
                165                 170                 175

His Cys Pro Ala Gly Asn Ser Tyr Thr Ser Phe Ala Thr Tyr His Thr
            180                 185                 190

Pro Ala Thr Asp Cys Ser Asp Gly Asn Tyr Asn Arg Asn Ala Ser Leu
            195                 200                 205

Asn Ser Phe Lys Glu Tyr Phe Asn Leu Arg Asn Cys Thr Phe Met Tyr
    210                 215                 220

Thr Tyr Asn Ile Thr Glu Asp Glu Ile Leu Glu Trp Phe Gly Ile Thr
225                 230                 235                 240

Gln Thr Ala Gln Gly Val His Leu Phe Ser Ser Arg Tyr Val Asp Leu
                245                 250                 255

Tyr Gly Gly Asn Met Phe Gln Phe Ala Thr Leu Pro Val Tyr Asp Thr
            260                 265                 270

Ile Lys Tyr Tyr Ser Ile Ile Pro His Ser Ile Arg Ser Ile Gln Ser
            275                 280                 285

Asp Arg Lys Ala Trp Ala Ala Phe Tyr Val Tyr Lys Leu Gln Pro Leu
    290                 295                 300

Thr Phe Leu Leu Asp Phe Ser Val Asp Gly Tyr Ile Arg Arg Ala Ile
305                 310                 315                 320

Asp Cys Gly Phe Asn Asp Leu Ser Gln Leu His Cys Ser Tyr Glu Ser
                325                 330                 335

Phe Asp Val Glu Ser Gly Val Tyr Ser Val Ser Ser Phe Glu Ala Lys
            340                 345                 350

Pro Ser Gly Ser Val Val Glu Gln Ala Glu Gly Val Glu Cys Asp Phe
            355                 360                 365

Ser Pro Leu Leu Ser Gly Thr Pro Pro Gln Val Tyr Asn Phe Lys Arg
    370                 375                 380

Leu Val Phe Thr Asn Cys Asn Tyr Asn Leu Thr Lys Leu Leu Ser Leu
385                 390                 395                 400

Phe Ser Val Asn Asp Phe Thr Cys Ser Gln Ile Ser Pro Ala Ala Ile
                405                 410                 415

Ala Ser Asn Cys Tyr Ser Ser Leu Ile Leu Asp Tyr Phe Ser Tyr Pro
            420                 425                 430

Leu Ser Met Lys Ser Asp Leu Ser Val Ser Ser Ala Gly Pro Ile Ser
            435                 440                 445

Gln Phe Asn Tyr Lys Gln Ser Phe Ser Asn Pro Thr Cys Leu Ile Leu
    450                 455                 460

Ala Thr Val Pro His Asn Leu Thr Thr Ile Thr Lys Pro Leu Lys Tyr
465                 470                 475                 480

Ser Tyr Ile Asn Lys Cys Ser Arg Leu Leu Ser Asp Asp Arg Thr Glu
                485                 490                 495

Val Pro Gln Leu Val Asn Ala Asn Gln Tyr Ser Pro Cys Val Ser Ile

```
                500             505             510
Val Pro Ser Thr Val Trp Glu Asp Gly Asp Tyr Tyr Arg Lys Gln Leu
            515             520             525

Ser Pro Leu Glu Gly Gly Trp Leu Val Ala Ser Gly Ser Thr Val
530             535             540

Ala Met Thr Glu Gln Leu Gln Met Gly Phe Gly Ile Thr Val Gln Tyr
545             550             555             560

Gly Thr Asp Thr Asn Ser Val Cys Pro Lys Leu Glu Phe Ala Asn Asp
            565             570             575

Thr Lys Ile Ala Ser Gln Leu Gly Asn Cys Val Glu Tyr Ser Leu Tyr
            580             585             590

Gly Val Ser Gly Arg Gly Val Phe Gln Asn Cys Thr Ala Val Gly Val
            595             600             605

Arg Gln Gln Arg Phe Val Tyr Asp Ala Tyr Gln Asn Leu Val Gly Tyr
            610             615             620

Tyr Ser Asp Asp Gly Asn Tyr Tyr Cys Leu Arg Ala Cys Val Ser Val
625             630             635             640

Pro Val Ser Val Ile Tyr Asp Lys Glu Thr Lys Thr His Ala Thr Leu
            645             650             655

Phe Gly Ser Val Ala Cys Glu His Ile Ser Ser Thr Met Ser Gln Tyr
            660             665             670

Ser Arg Ser Thr Arg Ser Met Leu Lys Arg Arg Asp Ser Thr Tyr Gly
            675             680             685

Pro Leu Gln Thr Pro Val Gly Cys Val Leu Gly Leu Val Asn Ser Ser
            690             695             700

Leu Phe Val Glu Asp Cys Lys Leu Pro Leu Gly Gln Ser Leu Cys Ala
705             710             715             720

Leu Pro Asp Thr Pro Ser Thr Leu Thr Pro Arg Ser Val Arg Ser Val
            725             730             735

Pro Gly Glu Met Arg Leu Ala Ser Ile Ala Phe Asn His Pro Ile Gln
            740             745             750

Val Asp Gln Leu Asn Ser Ser Tyr Phe Lys Leu Ser Ile Pro Thr Asn
            755             760             765

Phe Ser Phe Gly Val Thr Gln Glu Tyr Ile Gln Thr Thr Ile Gln Lys
770             775             780

Val Thr Val Asp Cys Lys Gln Tyr Val Cys Asn Gly Phe Gln Lys Cys
785             790             795             800

Glu Gln Leu Leu Arg Glu Tyr Gly Gln Phe Cys Ser Lys Ile Asn Gln
            805             810             815

Ala Leu His Gly Ala Asn Leu Arg Gln Asp Asp Ser Val Arg Asn Leu
            820             825             830

Phe Ala Ser Val Lys Ser Ser Gln Ser Ser Pro Ile Ile Pro Gly Phe
            835             840             845

Gly Gly Asp Phe Asn Leu Thr Leu Leu Glu Pro Val Ser Ile Ser Thr
            850             855             860

Gly Ser Arg Ser Ala Arg Ser Ala Ile Glu Asp Leu Leu Phe Asp Lys
865             870             875             880

Val Thr Ile Ala Asp Pro Gly Tyr Met Gln Gly Tyr Asp Asp Cys Met
            885             890             895

Gln Gln Gly Pro Ala Ser Ala Arg Asp Leu Ile Cys Ala Gln Tyr Val
            900             905             910

Ala Gly Tyr Lys Val Leu Pro Pro Leu Met Asp Val Asn Met Glu Ala
            915             920             925
```

Ala Tyr Thr Ser Ser Leu Leu Gly Ser Ile Ala Gly Val Gly Trp Thr
            930                 935                 940

Ala Gly Leu Ser Ser Phe Ala Ala Ile Pro Phe Ala Gln Ser Ile Phe
945                 950                 955                 960

Tyr Arg Leu Asn Gly Val Gly Ile Thr Gln Gln Val Leu Ser Glu Asn
                965                 970                 975

Gln Lys Leu Ile Ala Asn Lys Phe Asn Gln Ala Leu Gly Ala Met Gln
            980                 985                 990

Thr Gly Phe Thr Thr Thr Asn Glu Ala Phe Gln Lys Val Gln Asp Ala
        995                 1000                1005

Val Asn Asn Asn Ala Gln Ala Leu Ser Lys Leu Ala Ser Glu Leu
    1010                1015                1020

Ser Asn Thr Phe Gly Ala Ile Ser Ala Ser Ile Gly Asp Ile Ile
    1025                1030                1035

Gln Arg Leu Asp Val Leu Glu Gln Asp Ala Gln Ile Asp Arg Leu
    1040                1045                1050

Ile Asn Gly Arg Leu Thr Thr Leu Asn Ala Phe Val Ala Gln Gln
    1055                1060                1065

Leu Val Arg Ser Glu Ser Ala Ala Leu Ser Ala Gln Leu Ala Lys
    1070                1075                1080

Asp Lys Val Asn Glu Cys Val Lys Ala Gln Ser Lys Arg Ser Gly
    1085                1090                1095

Phe Cys Gly Gln Gly Thr His Ile Val Ser Phe Val Val Asn Ala
    1100                1105                1110

Pro Asn Gly Leu Tyr Phe Met His Val Gly Tyr Tyr Pro Ser Asn
    1115                1120                1125

His Ile Glu Val Val Ser Ala Tyr Gly Leu Cys Asp Ala Ala Asn
    1130                1135                1140

Pro Thr Asn Cys Ile Ala Pro Val Asn Gly Tyr Phe Ile Lys Thr
    1145                1150                1155

Asn Asn Thr Arg Ile Val Asp Glu Trp Ser Tyr Thr Gly Ser Ser
    1160                1165                1170

Phe Tyr Ala Pro Glu Pro Ile Thr Ser Leu Asn Thr Lys Tyr Val
    1175                1180                1185

Ala Pro Gln Val Thr Tyr Gln Asn Ile Ser Thr Asn Leu Pro Pro
    1190                1195                1200

Pro Leu Leu Gly Asn Ser Thr Gly Ile Asp Phe Gln Asp Glu Leu
    1205                1210                1215

Asp Glu Phe Phe Lys Asn Val Ser Thr Ser Ile Pro Asn Phe Gly
    1220                1225                1230

Ser Leu Thr Gln Ile Asn Thr Thr Leu Leu Asp Leu Thr Tyr Glu
    1235                1240                1245

Met Leu Ser Leu Gln Gln Val Val Lys Ala Leu Asn Glu Ser Tyr
    1250                1255                1260

Ile Asp Leu Lys Glu Leu Gly Asn Tyr Thr Tyr
    1265                1270

<210> SEQ ID NO 12
<211> LENGTH: 17
<212> TYPE: PRT
<213> ORGANISM: Artificial sequence
<220> FEATURE:
<223> OTHER INFORMATION: Synthetic sequence

<400> SEQUENCE: 12

```
Met Ile His Ser Val Phe Leu Leu Met Phe Leu Leu Thr Pro Thr Glu
1               5                   10                  15

Ser

<210> SEQ ID NO 13
<211> LENGTH: 65
<212> TYPE: PRT
<213> ORGANISM: Artificial sequence
<220> FEATURE:
<223> OTHER INFORMATION: Synthetic sequence

<400> SEQUENCE: 13

Thr Gly Ile Asp Phe Gln Asp Glu Leu Asp Glu Phe Phe Lys Asn Val
1               5                   10                  15

Ser Thr Ser Ile Pro Asn Phe Gly Ser Leu Thr Gln Ile Asn Thr Thr
            20                  25                  30

Leu Leu Asp Leu Thr Tyr Glu Met Leu Ser Leu Gln Gln Val Val Lys
        35                  40                  45

Ala Leu Asn Glu Ser Tyr Ile Asp Leu Lys Glu Leu Gly Asn Tyr Thr
    50                  55                  60

Tyr
65

<210> SEQ ID NO 14
<211> LENGTH: 1195
<212> TYPE: PRT
<213> ORGANISM: Artificial sequence
<220> FEATURE:
<223> OTHER INFORMATION: Synthetic sequence

<400> SEQUENCE: 14

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205
```

```
Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
    355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
    435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
    595                 600                 605

Val Ala Ile His Ala Asp Gln Leu Thr Pro Thr Trp Arg Val Tyr Ser
    610                 615                 620
```

```
Thr Gly Ser Asn Val Phe Gln Thr Arg Ala Gly Cys Leu Ile Gly Ala
625                 630                 635                 640

Glu His Val Asn Ser Tyr Glu Cys Asp Ile Pro Ile Gly Ala Gly
    645                 650                 655

Ile Cys Ala Ser Tyr Gln Thr Gln Thr Asn Ser Pro Arg Arg Ala Arg
        660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln
        1010                1015                1020

Ser Lys Arg Val Asp Phe Cys Gly Lys Gly Tyr His Leu Met Ser
        1025                1030                1035

Phe Pro Gln Ser Ala Pro His Gly Val Val Phe Leu His Val Thr
```

```
                1040                1045                1050

Tyr Val Pro Ala Gln Glu Lys Asn Phe Thr Thr Ala Pro Ala Ile
        1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Glu Glu Leu Asp Lys Tyr Phe
    1130                1135                1140

Lys Asn His Thr Ser Pro Asp Val Asp Leu Gly Asp Ile Ser Gly
    1145                1150                1155

Ile Asn Ala Ser Val Val Asn Ile Gln Lys Glu Ile Asp Arg Leu
    1160                1165                1170

Asn Glu Val Ala Lys Asn Leu Asn Glu Ser Leu Ile Asp Leu Gln
    1175                1180                1185

Glu Leu Gly Lys Tyr Glu Gln
    1190                1195

<210> SEQ ID NO 15
<211> LENGTH: 13
<212> TYPE: PRT
<213> ORGANISM: Artificial sequence
<220> FEATURE:
<223> OTHER INFORMATION: Synthetic sequence

<400> SEQUENCE: 15

Met Phe Val Phe Leu Val Leu Leu Pro Leu Val Ser Ser
1               5                   10

<210> SEQ ID NO 16
<211> LENGTH: 14
<212> TYPE: PRT
<213> ORGANISM: Artificial sequence
<220> FEATURE:
<223> OTHER INFORMATION: Synthetic sequence

<400> SEQUENCE: 16

Val Pro Thr Ile Val Met Val Asp Ala Tyr Lys Arg Tyr Lys
1               5                   10

<210> SEQ ID NO 17
<211> LENGTH: 117
<212> TYPE: PRT
<213> ORGANISM: Artificial sequence
<220> FEATURE:
<223> OTHER INFORMATION: Synthetic sequence

<400> SEQUENCE: 17

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Ser Ser Gly Lys Thr Ile Ser Thr Trp Ile Ser Asp Gly His
    50                  55                  60
```

```
Val Lys Asp Phe Tyr Leu Tyr Pro Gly Lys Tyr Thr Phe Val Glu Thr
 65                  70                  75                  80

Ala Ala Pro Asp Gly Tyr Glu Val Ala Thr Ala Ile Thr Phe Thr Val
                 85                  90                  95

Asn Glu Gln Gly Gln Val Thr Val Asn Gly Glu Ala Thr Lys Gly Asp
            100                 105                 110

Ala His Thr Ala Ser
            115

<210> SEQ ID NO 18
<211> LENGTH: 6
<212> TYPE: PRT
<213> ORGANISM: Artificial sequence
<220> FEATURE:
<223> OTHER INFORMATION: Synthetic sequence

<400> SEQUENCE: 18

Gly Ser Ala Gly Ser Val
1               5

<210> SEQ ID NO 19
<211> LENGTH: 4
<212> TYPE: PRT
<213> ORGANISM: Artificial sequence
<220> FEATURE:
<223> OTHER INFORMATION: Synthetic sequence

<400> SEQUENCE: 19

Arg Arg Ala Arg
1

<210> SEQ ID NO 20
<211> LENGTH: 4
<212> TYPE: PRT
<213> ORGANISM: Artificial sequence
<220> FEATURE:
<223> OTHER INFORMATION: Synthetic sequence

<400> SEQUENCE: 20

Gly Ser Ala Gly
1

<210> SEQ ID NO 21
<211> LENGTH: 5
<212> TYPE: PRT
<213> ORGANISM: Artificial sequence
<220> FEATURE:
<223> OTHER INFORMATION: Synthetic sequence

<400> SEQUENCE: 21

Gly Gly Gly Gly Ser
1               5

<210> SEQ ID NO 22
<211> LENGTH: 10
<212> TYPE: PRT
<213> ORGANISM: Artificial sequence
<220> FEATURE:
<223> OTHER INFORMATION: Synthetic sequence

<400> SEQUENCE: 22

Gly Gly Gly Gly Ser Gly Gly Gly Gly Ser
1               5                   10
```

```
<210> SEQ ID NO 23
<211> LENGTH: 205
<212> TYPE: PRT
<213> ORGANISM: Artificial sequence
<220> FEATURE:
<223> OTHER INFORMATION: Synthetic sequence

<400> SEQUENCE: 23

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu Ala Val Phe
                20                  25                  30

Val Gly Gly Val His Leu Ile Glu Ile Thr Phe Thr Val Pro Asp Ala
            35                  40                  45

Asp Thr Val Ile Lys Glu Leu Ser Phe Leu Lys Glu Leu Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Ile Ala Glu Val Ala Ala Lys
            180                 185                 190

Ala Ala Ala Phe Val Glu Lys Ile Arg Gly Cys Thr Glu
        195                 200                 205

<210> SEQ ID NO 24
<211> LENGTH: 242
<212> TYPE: PRT
<213> ORGANISM: Artificial sequence
<220> FEATURE:
<223> OTHER INFORMATION: Synthetic sequence

<400> SEQUENCE: 24

Ala Ala Ala Lys Pro Ala Thr Thr Glu Gly Glu Phe Pro Glu Thr Arg
1               5                   10                  15

Glu Lys Met Ser Gly Ile Arg Arg Ala Ile Ala Lys Ala Met Val His
                20                  25                  30

Ser Lys His Thr Ala Pro His Val Thr Leu Met Asp Glu Ala Asp Val
            35                  40                  45

Thr Lys Leu Val Ala His Arg Lys Lys Phe Lys Ala Ile Ala Ala Glu
        50                  55                  60

Lys Gly Ile Lys Leu Thr Phe Leu Pro Tyr Val Val Lys Ala Leu Val
65                  70                  75                  80

Ser Ala Leu Arg Glu Tyr Pro Val Leu Asn Thr Ala Ile Asp Asp Glu
                85                  90                  95

Thr Glu Glu Ile Ile Gln Lys His Tyr Tyr Asn Ile Gly Ile Ala Ala
            100                 105                 110
```

```
Asp Thr Asp Arg Gly Leu Leu Val Pro Val Ile Lys His Ala Asp Arg
        115                 120                 125

Lys Pro Ile Phe Ala Leu Ala Gln Glu Ile Asn Glu Leu Ala Glu Lys
    130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
            180                 185                 190

Lys Pro Ile Val Arg Asp Gly Glu Ile Val Ala Ala Pro Met Leu Ala
        195                 200                 205

Leu Ser Leu Ser Phe Asp His Arg Met Ile Asp Gly Ala Thr Ala Gln
    210                 215                 220

Lys Ala Leu Asn His Ile Lys Arg Leu Leu Ser Asp Pro Glu Leu Leu
225                 230                 235                 240

Leu Met
```

<210> SEQ ID NO 25
<211> LENGTH: 162
<212> TYPE: PRT
<213> ORGANISM: Artificial sequence
<220> FEATURE:
<223> OTHER INFORMATION: Synthetic sequence

<400> SEQUENCE: 25

```
Asp Ile Ile Lys Leu Leu Asn Glu Gln Val Asn Lys Glu Met Asn Ser
1               5                   10                  15

Ser Asn Leu Tyr Met Ser Met Ser Ser Trp Cys Tyr Thr His Ser Leu
                20                  25                  30

Asp Gly Ala Gly Leu Phe Leu Phe Asp His Ala Ala Glu Glu Tyr Glu
            35                  40                  45

His Ala Lys Lys Leu Ile Ile Phe Leu Asn Glu Asn Asn Val Pro Val
        50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu Gln His Ile Ser Glu Ser
                85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Glu Val
        115                 120                 125

Leu Phe Lys Asp Ile Leu Asp Lys Ile Glu Leu Ile Gly Asn Glu Asn
    130                 135                 140

His Gly Leu Tyr Leu Ala Asp Gln Tyr Val Lys Gly Ile Ala Lys Ser
145                 150                 155                 160

Arg Lys
```

<210> SEQ ID NO 26
<211> LENGTH: 27
<212> TYPE: PRT
<213> ORGANISM: Artificial sequence
<220> FEATURE:
<223> OTHER INFORMATION: Synthetic sequence

<400> SEQUENCE: 26

```
Gly Tyr Ile Pro Glu Ala Pro Arg Asp Gly Gln Ala Tyr Val Arg Lys
```

```
1               5                   10                  15
Asp Gly Glu Trp Val Leu Leu Ser Thr Phe Leu
                20                  25
```

<210> SEQ ID NO 27
<211> LENGTH: 102
<212> TYPE: PRT
<213> ORGANISM: Artificial sequence
<220> FEATURE:
<223> OTHER INFORMATION: Synthetic sequence

<400> SEQUENCE: 27

```
Glu Val Arg Ile Phe Ala Gly Asn Asp Pro Ala His Thr Ala Thr Gly
1               5                   10                  15

Ser Ser Gly Ile Ser Ser Pro Thr Pro Ala Leu Thr Pro Leu Met Leu
                20                  25                  30

Asp Glu Ala Thr Gly Lys Leu Val Trp Asp Gly Gln Lys Ala Gly
            35                  40                  45

Ser Ala Val Gly Ile Leu Val Leu Pro Leu Gly Thr Glu Thr Ala
        50                  55                  60

Leu Thr Tyr Tyr Lys Ser Gly Thr Phe Ala Thr Glu Ala Ile His Trp
65                  70                  75                  80

Pro Glu Ser Val Asp Glu His Lys Lys Ala Asn Ala Phe Ala Gly Ser
                85                  90                  95

Ala Leu Ser His Ala Ala
            100
```

<210> SEQ ID NO 28
<211> LENGTH: 58
<212> TYPE: PRT
<213> ORGANISM: Artificial sequence
<220> FEATURE:
<223> OTHER INFORMATION: Synthetic sequence

<400> SEQUENCE: 28

```
Phe Ser Glu Glu Gln Lys Lys Ala Leu Asp Leu Ala Phe Tyr Phe Asp
1               5                   10                  15

Arg Arg Leu Thr Pro Glu Trp Arg Arg Tyr Leu Ser Gln Arg Leu Gly
                20                  25                  30

Leu Asn Glu Glu Gln Ile Glu Arg Trp Phe Arg Arg Lys Glu Gln Gln
            35                  40                  45

Ile Gly Trp Ser His Pro Gln Phe Glu Lys
        50                  55
```

<210> SEQ ID NO 29
<211> LENGTH: 46
<212> TYPE: PRT
<213> ORGANISM: Artificial sequence
<220> FEATURE:
<223> OTHER INFORMATION: Synthetic sequence

<400> SEQUENCE: 29

```
Ser Pro Ala Val Asp Ile Gly Asp Arg Leu Asp Glu Leu Glu Lys Ala
1               5                   10                  15

Leu Glu Ala Leu Ser Ala Glu Asp Gly His Asp Val Gly Gln Arg
                20                  25                  30

Leu Glu Ser Leu Leu Arg Arg Trp Asn Ser Arg Arg Ala Asp
            35                  40                  45
```

<210> SEQ ID NO 30

```
<211> LENGTH: 13
<212> TYPE: PRT
<213> ORGANISM: Artificial sequence
<220> FEATURE:
<223> OTHER INFORMATION: Synthetic sequence

<400> SEQUENCE: 30

Ala Lys Phe Val Ala Ala Trp Thr Leu Lys Ala Ala Ala
1               5                   10

<210> SEQ ID NO 31
<211> LENGTH: 6
<212> TYPE: PRT
<213> ORGANISM: Artificial sequence
<220> FEATURE:
<223> OTHER INFORMATION: Synthetic sequence

<400> SEQUENCE: 31

Arg Arg Ala Arg Ser Val
1               5

<210> SEQ ID NO 32
<211> LENGTH: 1149
<212> TYPE: PRT
<213> ORGANISM: Artificial sequence
<220> FEATURE:
<223> OTHER INFORMATION: Synthetic sequence

<400> SEQUENCE: 32

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

```
Leu Leu Ala Leu His Arg Ser Tyr Leu Thr Pro Gly Asp Ser Ser Ser
            245                 250                 255

Gly Trp Thr Ala Gly Ala Ala Tyr Val Gly Tyr Leu Gln Pro
        260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

-continued

```
                660                 665                 670
Ser Tyr Gln Thr Gln Thr Asn Ser Pro Gly Ser Ala Gly Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Gly Gly Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080
```

Asp Gly Lys Ala His Phe Pro Arg Glu Gly Val Phe Val Ser Asn
1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys
    1145

<210> SEQ ID NO 33
<211> LENGTH: 1136
<212> TYPE: PRT
<213> ORGANISM: Artificial sequence
<220> FEATURE:
<223> OTHER INFORMATION: Synthetic sequence

<400> SEQUENCE: 33

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
            275                 280                 285

```
Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Gly
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700
```

```
Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
            725                 730                 735

Ser Asn Leu Leu Leu Gln Tyr Gly Ser Phe Cys Thr Gln Leu Asn Arg
        740                 745                 750

Ala Leu Thr Gly Ile Ala Val Glu Gln Asp Lys Asn Thr Gln Glu Val
    755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
        820                 825                 830

Ala Arg Asp Leu Ile Cys Ala Gln Lys Phe Asn Gly Leu Thr Val Leu
    835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
        900                 905                 910

Gln Phe Asn Ser Ala Ile Gly Lys Ile Gln Asp Ser Leu Ser Ser Thr
    915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Gly Gly Glu Ala
            965                 970                 975

Glu Val Gln Ile Asp Arg Leu Ile Thr Gly Arg Leu Gln Ser Leu Gln
        980                 985                 990

Thr Tyr Val Thr Gln Gln Leu Ile Arg Ala Ala Glu Ile Arg Ala Ser
    995                 1000                1005

Ala Asn Leu Ala Ala Thr Lys Met Ser Glu Cys Val Leu Gly Gln
1010                1015                1020

Ser Lys Arg Val Asp Phe Cys Gly Lys Gly Tyr His Leu Met Ser
1025                1030                1035

Phe Pro Gln Ser Ala Pro His Gly Val Val Phe Leu His Val Thr
1040                1045                1050

Tyr Val Pro Ala Gln Glu Lys Asn Phe Thr Ala Pro Ala Ile
1055                1060                1065

Cys His Asp Gly Lys Ala His Phe Pro Arg Glu Gly Val Phe Val
1070                1075                1080

Ser Asn Gly Thr His Trp Phe Val Thr Gln Arg Asn Phe Tyr Glu
1085                1090                1095

Pro Gln Ile Ile Thr Thr Asp Asn Thr Phe Val Ser Gly Asn Cys
1100                1105                1110

Asp Val Val Ile Gly Ile Val Asn Asn Thr Val Tyr Asp Pro Leu
```

```
                1115                1120                1125

Gln Pro Glu Leu Asp Ser Phe Lys
    1130                1135

<210> SEQ ID NO 34
<211> LENGTH: 1136
<212> TYPE: PRT
<213> ORGANISM: Artificial sequence
<220> FEATURE:
<223> OTHER INFORMATION: Synthetic sequence

<400> SEQUENCE: 34

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
```

-continued

```
                340                 345                 350
Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Gly
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765
```

```
Phe Ala Gln Val Lys Gln Ile Tyr Lys Thr Pro Pro Ile Lys Asp Phe
        770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
        835                 840                 845
Pro Pro Leu Leu Thr Asp Glu Met Ile Ala Gln Tyr Thr Ser Ala Leu
850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Gln Ile Ala Asn
                900                 905                 910
Gln Phe Asn Lys Ala Ile Ser Gln Ile Gln Glu Ser Leu Thr Thr Thr
        915                 920                 925
Ser Thr Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Gly Gly Glu Ala
                965                 970                 975
Glu Val Gln Ile Asp Arg Leu Ile Thr Gly Arg Leu Gln Ser Leu Gln
                980                 985                 990
Thr Tyr Val Thr Gln Gln Leu Ile Arg Ala Ala Glu Ile Arg Ala Ser
        995                 1000                1005
Ala Asn Leu Ala Ala Thr Lys Met Ser Glu Cys Val Leu Gly Gln
        1010                1015                1020
Ser Lys Arg Val Asp Phe Cys Gly Lys Gly Tyr His Leu Met Ser
        1025                1030                1035
Phe Pro Gln Ser Ala Pro His Gly Val Val Phe Leu His Val Thr
        1040                1045                1050
Tyr Val Pro Ala Gln Glu Lys Asn Phe Thr Thr Ala Pro Ala Ile
        1055                1060                1065
Cys His Asp Gly Lys Ala His Phe Pro Arg Glu Gly Val Phe Val
        1070                1075                1080
Ser Asn Gly Thr His Trp Phe Val Thr Gln Arg Asn Phe Tyr Glu
        1085                1090                1095
Pro Gln Ile Ile Thr Thr Asp Asn Thr Phe Val Ser Gly Asn Cys
        1100                1105                1110
Asp Val Val Ile Gly Ile Val Asn Asn Thr Val Tyr Asp Pro Leu
        1115                1120                1125
Gln Pro Glu Leu Asp Ser Phe Lys
        1130                1135

<210> SEQ ID NO 35
<211> LENGTH: 1170
<212> TYPE: PRT
<213> ORGANISM: Artificial sequence
<220> FEATURE:
```

<223> OTHER INFORMATION: Synthetic sequence

<400> SEQUENCE: 35

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400
```

-continued

```
Gln Thr Gly Lys Ile Ala Asp Tyr Asn Tyr Lys Leu Pro Asp Asp Phe
                405                 410                 415
Thr Gly Cys Val Ile Ala Trp Asn Ser Asn Asn Leu Asp Ser Lys Val
            420                 425                 430
Gly Gly Asn Tyr Asn Tyr Leu Tyr Arg Leu Phe Arg Lys Ser Asn Leu
        435                 440                 445
Lys Pro Phe Glu Arg Asp Ile Ser Thr Glu Ile Tyr Gln Ala Gly Ser
450                 455                 460
Thr Pro Cys Asn Gly Val Glu Gly Phe Asn Cys Tyr Phe Pro Leu Gln
465                 470                 475                 480
Ser Tyr Gly Phe Gln Pro Thr Asn Gly Val Gly Tyr Gln Pro Tyr Arg
            485                 490                 495
Val Val Val Leu Ser Phe Glu Leu Leu His Ala Pro Ala Thr Val Cys
        500                 505                 510
Gly Pro Lys Lys Ser Thr Asn Leu Val Lys Asn Lys Cys Val Asn Phe
            515                 520                 525
Asn Phe Asn Gly Leu Thr Gly Thr Gly Val Leu Thr Glu Ser Asn Lys
        530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
            580                 585                 590
Asn Gln Val Ala Val Leu Tyr Gln Asp Val Asn Cys Thr Glu Val Pro
        595                 600                 605
Val Ala Ile His Ala Asp Gln Leu Thr Pro Thr Trp Arg Val Tyr Ser
    610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Gly Ser Ala Gly
            660                 665                 670
Ser Val Ala Ser Gln Ser Ile Ile Ala Tyr Thr Met Ser Leu Gly Ala
        675                 680                 685
Glu Asn Ser Val Ala Tyr Ser Asn Asn Ser Ile Ala Ile Pro Thr Asn
    690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
        755                 760                 765
Phe Ala Gln Val Lys Gln Ile Tyr Lys Thr Pro Pro Ile Lys Asp Phe
    770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
```

820                 825                 830
Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Gly Gly Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser
    1025                1030                1035

Phe Pro Gln Ser Ala Pro His Gly Val Val Phe Leu His Val Thr
    1040                1045                1050

Tyr Val Pro Ala Gln Glu Lys Asn Phe Thr Thr Ala Pro Ala Ile
    1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Ala Ser Gly Gly Gly Gly Ser
    1130                1135                1140

Gly Tyr Ile Pro Glu Ala Pro Arg Asp Gly Gln Ala Tyr Val Arg
    1145                1150                1155

Lys Asp Gly Glu Trp Val Leu Leu Ser Thr Phe Leu
    1160                1165                1170

<210> SEQ ID NO 36
<211> LENGTH: 1245
<212> TYPE: PRT
<213> ORGANISM: Artificial sequence
<220> FEATURE:
<223> OTHER INFORMATION: Synthetic sequence

<400> SEQUENCE: 36

Gln Cys Val Asn Leu Thr Thr Arg Thr Gln Leu Pro Pro Ala Tyr Thr

-continued

```
1               5                   10                  15
Asn Ser Phe Thr Arg Gly Val Tyr Tyr Pro Asp Lys Val Phe Arg Ser
                20                  25                  30
Ser Val Leu His Ser Thr Gln Asp Leu Phe Leu Pro Phe Phe Ser Asn
                35                  40                  45
Val Thr Trp Phe His Ala Ile His Val Ser Gly Thr Asn Gly Thr Lys
                50                  55                  60
Arg Phe Asp Asn Pro Val Leu Pro Phe Asn Asp Gly Val Tyr Phe Ala
65                  70                  75                  80
Ser Thr Glu Lys Ser Asn Ile Ile Arg Gly Trp Ile Phe Gly Thr Thr
                85                  90                  95
Leu Asp Ser Lys Thr Gln Ser Leu Leu Ile Val Asn Asn Ala Thr Asn
                100                 105                 110
Val Val Ile Lys Val Cys Glu Phe Gln Phe Cys Asn Asp Pro Phe Leu
                115                 120                 125
Gly Val Tyr Tyr His Lys Asn Asn Lys Ser Trp Met Glu Ser Glu Phe
                130                 135                 140
Arg Val Tyr Ser Ser Ala Asn Asn Cys Thr Phe Glu Tyr Val Ser Gln
145                 150                 155                 160
Pro Phe Leu Met Asp Leu Glu Gly Lys Gln Gly Asn Phe Lys Asn Leu
                165                 170                 175
Arg Glu Phe Val Phe Lys Asn Ile Asp Gly Tyr Phe Lys Ile Tyr Ser
                180                 185                 190
Lys His Thr Pro Ile Asn Leu Val Arg Asp Leu Pro Gln Gly Phe Ser
                195                 200                 205
Ala Leu Glu Pro Leu Val Asp Leu Pro Ile Gly Ile Asn Ile Thr Arg
                210                 215                 220
Phe Gln Thr Leu Leu Ala Leu His Arg Ser Tyr Leu Thr Pro Gly Asp
225                 230                 235                 240
Ser Ser Ser Gly Trp Thr Ala Gly Ala Ala Ala Tyr Tyr Val Gly Tyr
                245                 250                 255
Leu Gln Pro Arg Thr Phe Leu Leu Lys Tyr Asn Glu Asn Gly Thr Ile
                260                 265                 270
Thr Asp Ala Val Asp Cys Ala Leu Asp Pro Leu Ser Glu Thr Lys Cys
                275                 280                 285
Thr Leu Lys Ser Phe Thr Val Glu Lys Gly Ile Tyr Gln Thr Ser Asn
                290                 295                 300
Phe Arg Val Gln Pro Thr Glu Ser Ile Val Arg Phe Pro Asn Ile Thr
305                 310                 315                 320
Asn Leu Cys Pro Phe Gly Glu Val Phe Asn Ala Thr Arg Phe Ala Ser
                325                 330                 335
Val Tyr Ala Trp Asn Arg Lys Arg Ile Ser Asn Cys Val Ala Asp Tyr
                340                 345                 350
Ser Val Leu Tyr Asn Ser Ala Ser Phe Ser Thr Phe Lys Cys Tyr Gly
                355                 360                 365
Val Ser Pro Thr Lys Leu Asn Asp Leu Cys Phe Thr Asn Val Tyr Ala
                370                 375                 380
Asp Ser Phe Val Ile Arg Gly Asp Glu Val Arg Gln Ile Ala Pro Gly
385                 390                 395                 400
Gln Thr Gly Lys Ile Ala Asp Tyr Asn Tyr Lys Leu Pro Asp Asp Phe
                405                 410                 415
Thr Gly Cys Val Ile Ala Trp Asn Ser Asn Asn Leu Asp Ser Lys Val
                420                 425                 430
```

```
Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
            530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Gly
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845
```

```
Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Gly Gly Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser
    1025                1030                1035

Phe Pro Gln Ser Ala Pro His Gly Val Val Phe Leu His Val Thr
    1040                1045                1050

Tyr Val Pro Ala Gln Glu Lys Asn Phe Thr Thr Ala Pro Ala Ile
    1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Ala Ser Gly Gly Gly Gly Ser
    1130                1135                1140

Glu Val Arg Ile Phe Ala Gly Asn Asp Pro Ala His Thr Ala Thr
    1145                1150                1155

Gly Ser Ser Gly Ile Ser Ser Pro Thr Pro Ala Leu Thr Pro Leu
    1160                1165                1170

Met Leu Asp Glu Ala Thr Gly Lys Leu Val Val Trp Asp Gly Gln
    1175                1180                1185

Lys Ala Gly Ser Ala Val Gly Ile Leu Val Leu Pro Leu Glu Gly
    1190                1195                1200

Thr Glu Thr Ala Leu Thr Tyr Tyr Lys Ser Gly Thr Phe Ala Thr
    1205                1210                1215

Glu Ala Ile His Trp Pro Glu Ser Val Asp Glu His Lys Lys Ala
    1220                1225                1230

Asn Ala Phe Ala Gly Ser Ala Leu Ser His Ala Ala
    1235                1240                1245
```

```
<210> SEQ ID NO 37
<211> LENGTH: 1245
<212> TYPE: PRT
<213> ORGANISM: Artificial sequence
<220> FEATURE:
<223> OTHER INFORMATION: Synthetic sequence

<400> SEQUENCE: 37
```

| | | | | | | | | | | | | | | |
|---|---|---|---|---|---|---|---|---|---|---|---|---|---|---|
| Gln | Cys | Val | Asn | Leu | Thr | Thr | Arg | Thr | Gln | Leu | Pro | Pro | Ala | Tyr | Thr |
| 1 | | | | 5 | | | | | 10 | | | | | 15 | |
| Asn | Ser | Phe | Thr | Arg | Gly | Val | Tyr | Tyr | Pro | Asp | Lys | Val | Phe | Arg | Ser |
| | | | 20 | | | | | 25 | | | | | 30 | | |
| Ser | Val | Leu | His | Ser | Thr | Gln | Asp | Leu | Phe | Leu | Pro | Phe | Phe | Ser | Asn |
| | | 35 | | | | | 40 | | | | | 45 | | | |
| Val | Thr | Trp | Phe | His | Ala | Ile | His | Val | Ser | Gly | Thr | Asn | Gly | Thr | Lys |
| | 50 | | | | | 55 | | | | | 60 | | | | |
| Arg | Phe | Asp | Asn | Pro | Val | Leu | Pro | Phe | Asn | Asp | Gly | Val | Tyr | Phe | Ala |
| 65 | | | | | 70 | | | | | 75 | | | | | 80 |
| Ser | Thr | Glu | Lys | Ser | Asn | Ile | Ile | Arg | Gly | Trp | Ile | Phe | Gly | Thr | Thr |
| | | | | 85 | | | | | 90 | | | | | 95 | |
| Leu | Asp | Ser | Lys | Thr | Gln | Ser | Leu | Leu | Ile | Val | Asn | Asn | Ala | Thr | Asn |
| | | | 100 | | | | | 105 | | | | | 110 | | |
| Val | Val | Ile | Lys | Val | Cys | Glu | Phe | Gln | Phe | Cys | Asn | Asp | Pro | Phe | Leu |
| | | 115 | | | | | 120 | | | | | 125 | | | |
| Gly | Val | Tyr | Tyr | His | Lys | Asn | Asn | Lys | Ser | Trp | Met | Glu | Ser | Glu | Phe |
| | 130 | | | | | 135 | | | | | 140 | | | | |
| Arg | Val | Tyr | Ser | Ser | Ala | Asn | Asn | Cys | Thr | Phe | Glu | Tyr | Val | Ser | Gln |
| 145 | | | | | 150 | | | | | 155 | | | | | 160 |
| Pro | Phe | Leu | Met | Asp | Leu | Glu | Gly | Lys | Gln | Gly | Asn | Phe | Lys | Asn | Leu |
| | | | | 165 | | | | | 170 | | | | | 175 | |
| Arg | Glu | Phe | Val | Phe | Lys | Asn | Ile | Asp | Gly | Tyr | Phe | Lys | Ile | Tyr | Ser |
| | | | 180 | | | | | 185 | | | | | 190 | | |
| Lys | His | Thr | Pro | Ile | Asn | Leu | Val | Arg | Asp | Leu | Pro | Gln | Gly | Phe | Ser |
| | | 195 | | | | | 200 | | | | | 205 | | | |
| Ala | Leu | Glu | Pro | Leu | Val | Asp | Leu | Pro | Ile | Gly | Ile | Asn | Ile | Thr | Arg |
| | 210 | | | | | 215 | | | | | 220 | | | | |
| Phe | Gln | Thr | Leu | Leu | Ala | Leu | His | Arg | Ser | Tyr | Leu | Thr | Pro | Gly | Asp |
| 225 | | | | | 230 | | | | | 235 | | | | | 240 |
| Ser | Ser | Ser | Gly | Trp | Thr | Ala | Gly | Ala | Ala | Tyr | Tyr | Val | Gly | Tyr |
| | | | | 245 | | | | | 250 | | | | | 255 |
| Leu | Gln | Pro | Arg | Thr | Phe | Leu | Leu | Lys | Tyr | Asn | Glu | Asn | Gly | Thr | Ile |
| | | | 260 | | | | | 265 | | | | | 270 | | |
| Thr | Asp | Ala | Val | Asp | Cys | Ala | Leu | Asp | Pro | Leu | Ser | Glu | Thr | Lys | Cys |
| | | 275 | | | | | 280 | | | | | 285 | | | |
| Thr | Leu | Lys | Ser | Phe | Thr | Val | Glu | Lys | Gly | Ile | Tyr | Gln | Thr | Ser | Asn |
| | 290 | | | | | 295 | | | | | 300 | | | | |
| Phe | Arg | Val | Gln | Pro | Thr | Glu | Ser | Ile | Val | Arg | Phe | Pro | Asn | Ile | Thr |
| 305 | | | | | 310 | | | | | 315 | | | | | 320 |
| Asn | Leu | Cys | Pro | Phe | Gly | Glu | Val | Phe | Asn | Ala | Thr | Arg | Phe | Ala | Ser |
| | | | | 325 | | | | | 330 | | | | | 335 | |
| Val | Tyr | Ala | Trp | Asn | Arg | Lys | Arg | Ile | Ser | Asn | Cys | Val | Ala | Asp | Tyr |
| | | | 340 | | | | | 345 | | | | | 350 | | |
| Ser | Val | Leu | Tyr | Asn | Ser | Ala | Ser | Phe | Ser | Thr | Phe | Lys | Cys | Tyr | Gly |
| | | 355 | | | | | 360 | | | | | 365 | | | |
| Val | Ser | Pro | Thr | Lys | Leu | Asn | Asp | Leu | Cys | Phe | Thr | Asn | Val | Tyr | Ala |

-continued

```
                370                 375                 380
Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
                595                 600                 605

Val Ala Ile His Ala Asp Gln Leu Thr Pro Thr Trp Arg Val Tyr Ser
610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Gly
                660                 665                 670

Ser Val Ala Ser Gln Ser Ile Ile Ala Tyr Thr Met Ser Leu Gly Ala
                675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
                770                 775                 780

Gly Gly Phe Asn Phe Ser Gln Ile Leu Pro Asp Pro Ser Lys Pro Ser
785                 790                 795                 800
```

-continued

```
Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
            850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Gln Ile Ala Asn
            900                 905                 910

Gln Phe Asn Lys Ala Ile Ser Gln Ile Gln Glu Ser Leu Thr Thr Thr
            915                 920                 925

Ser Thr Ala Leu Gly Lys Leu Gln Asp Val Val Asn Gln Asn Ala Gln
930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Gly Gly Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
        1010                1015                1020

Ser Lys Arg Val Asp Phe Cys Gly Lys Gly Tyr His Leu Met Ser
        1025                1030                1035

Phe Pro Gln Ser Ala Pro His Gly Val Val Phe Leu His Val Thr
        1040                1045                1050

Tyr Val Pro Ala Gln Glu Lys Asn Phe Thr Thr Ala Pro Ala Ile
        1055                1060                1065

Cys His Asp Gly Lys Ala His Phe Pro Arg Glu Gly Val Phe Val
        1070                1075                1080

Ser Asn Gly Thr His Trp Phe Val Thr Gln Arg Asn Phe Tyr Glu
        1085                1090                1095

Pro Gln Ile Ile Thr Thr Asp Asn Thr Phe Val Ser Gly Asn Cys
        1100                1105                1110

Asp Val Val Ile Gly Ile Val Asn Asn Thr Val Tyr Asp Pro Leu
        1115                1120                1125

Gln Pro Glu Leu Asp Ser Phe Lys Ala Ser Gly Gly Gly Ser
        1130                1135                1140

Glu Val Arg Ile Phe Ala Gly Asn Asp Pro Ala His Thr Ala Thr
        1145                1150                1155

Gly Ser Ser Gly Ile Ser Ser Pro Thr Pro Ala Leu Thr Pro Leu
        1160                1165                1170

Met Leu Asp Glu Ala Thr Gly Lys Leu Val Val Trp Asp Gly Gln
        1175                1180                1185

Lys Ala Gly Ser Ala Val Gly Ile Leu Val Leu Pro Leu Glu Gly
        1190                1195                1200
```

Thr Glu Thr Ala Leu Thr Tyr Tyr Lys Ser Gly Thr Phe Ala Thr
1205                1210                1215

Glu Ala Ile His Trp Pro Glu Ser Val Asp Glu His Lys Lys Ala
1220                1225                1230

Asn Ala Phe Ala Gly Ser Ala Leu Ser His Ala Ala
1235                1240                1245

<210> SEQ ID NO 38
<211> LENGTH: 1419
<212> TYPE: PRT
<213> ORGANISM: Artificial sequence
<220> FEATURE:
<223> OTHER INFORMATION: Synthetic sequence

<400> SEQUENCE: 38

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

```
Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
            610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Gly
            660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
```

```
            740             745             750
Ala Leu Thr Gly Ile Ala Val Glu Gln Asp Lys Asn Thr Gln Glu Val
            755             760             765
Phe Ala Gln Val Lys Gln Ile Tyr Lys Thr Pro Pro Ile Lys Asp Phe
            770             775             780
Gly Gly Phe Asn Phe Ser Gln Ile Leu Pro Asp Pro Ser Lys Pro Ser
785             790             795             800
Lys Arg Ser Phe Ile Glu Asp Leu Leu Phe Asn Lys Val Thr Leu Ala
                805             810             815
Asp Ala Gly Phe Ile Lys Gln Tyr Gly Asp Cys Leu Gly Asp Ile Ala
            820             825             830
Ala Arg Asp Leu Ile Cys Ala Gln Lys Phe Asn Gly Leu Thr Val Leu
            835             840             845
Pro Pro Leu Leu Thr Asp Glu Met Ile Ala Gln Tyr Thr Ser Ala Leu
            850             855             860
Leu Ala Gly Thr Ile Thr Ser Gly Trp Thr Phe Gly Ala Gly Ala Ala
865             870             875             880
Leu Gln Ile Pro Phe Ala Met Gln Met Ala Tyr Arg Phe Asn Gly Ile
                885             890             895
Gly Val Thr Gln Asn Val Leu Tyr Glu Asn Gln Lys Leu Ile Ala Asn
            900             905             910
Gln Phe Asn Ser Ala Ile Gly Lys Ile Gln Asp Ser Leu Ser Ser Thr
            915             920             925
Ala Ser Ala Leu Gly Lys Leu Gln Asp Val Val Asn Gln Asn Ala Gln
            930             935             940
Ala Leu Asn Thr Leu Val Lys Gln Leu Ser Ser Asn Phe Gly Ala Ile
945             950             955             960
Ser Ser Val Leu Asn Asp Ile Leu Ser Arg Leu Asp Gly Gly Glu Ala
                965             970             975
Glu Val Gln Ile Asp Arg Leu Ile Thr Gly Arg Leu Gln Ser Leu Gln
            980             985             990
Thr Tyr Val Thr Gln Gln Leu Ile Arg Ala Ala Glu Ile Arg Ala Ser
            995             1000            1005
Ala Asn Leu Ala Ala Thr Lys Met Ser Glu Cys Val Leu Gly Gln
    1010            1015            1020
Ser Lys Arg Val Asp Phe Cys Gly Lys Gly Tyr His Leu Met Ser
    1025            1030            1035
Phe Pro Gln Ser Ala Pro His Gly Val Val Phe Leu His Val Thr
    1040            1045            1050
Tyr Val Pro Ala Gln Glu Lys Asn Phe Thr Thr Ala Pro Ala Ile
    1055            1060            1065
Cys His Asp Gly Lys Ala His Phe Pro Arg Glu Gly Val Phe Val
    1070            1075            1080
Ser Asn Gly Thr His Trp Phe Val Thr Gln Arg Asn Phe Tyr Glu
    1085            1090            1095
Pro Gln Ile Ile Thr Thr Asp Asn Thr Phe Val Ser Gly Asn Cys
    1100            1105            1110
Asp Val Val Ile Gly Ile Val Asn Asn Thr Val Tyr Asp Pro Leu
    1115            1120            1125
Gln Pro Glu Leu Asp Ser Phe Lys Ala Ser Gly Gly Gly Gly Ser
    1130            1135            1140
Gly Gly Gly Gly Ser Met Lys Met Glu Glu Leu Phe Lys Lys His
    1145            1150            1155
```

Lys Ile Val Ala Val Leu Arg Ala Asn Ser Val Glu Glu Ala Lys
1160                1165                1170

Met Lys Ala Leu Ala Val Phe Val Gly Gly Val His Leu Ile Glu
    1175                1180                1185

Ile Thr Phe Thr Val Pro Asp Ala Asp Thr Val Ile Lys Glu Leu
    1190                1195                1200

Ser Phe Leu Lys Glu Leu Gly Ala Ile Ile Gly Ala Gly Thr Val
    1205                1210                1215

Thr Ser Val Glu Gln Cys Arg Lys Ala Val Glu Ser Gly Ala Glu
    1220                1225                1230

Phe Ile Val Ser Pro His Leu Asp Glu Glu Ile Ser Gln Phe Cys
    1235                1240                1245

Lys Glu Lys Gly Val Phe Tyr Met Pro Gly Val Met Thr Pro Thr
    1250                1255                1260

Glu Leu Val Lys Ala Met Lys Leu Gly His Thr Ile Leu Lys Leu
    1265                1270                1275

Phe Pro Gly Glu Val Val Gly Pro Gln Phe Val Lys Ala Met Lys
    1280                1285                1290

Gly Pro Phe Pro Asn Val Lys Phe Val Pro Thr Gly Gly Val Asn
    1295                1300                1305

Leu Asp Asn Val Cys Glu Trp Phe Lys Ala Gly Val Leu Ala Val
    1310                1315                1320

Gly Val Gly Ser Ala Leu Val Lys Gly Thr Ile Ala Glu Val Ala
    1325                1330                1335

Ala Lys Ala Ala Ala Phe Val Glu Lys Ile Arg Gly Cys Thr Glu
    1340                1345                1350

Gly Gly Gly Gly Ser Ser Pro Ala Val Asp Ile Gly Asp Arg Leu
    1355                1360                1365

Asp Glu Leu Glu Lys Ala Leu Glu Ala Leu Ser Ala Glu Asp Gly
    1370                1375                1380

His Asp Asp Val Gly Gln Arg Leu Glu Ser Leu Leu Arg Arg Trp
    1385                1390                1395

Asn Ser Arg Arg Ala Asp Gly Ser Ala Lys Phe Val Ala Ala Trp
    1400                1405                1410

Thr Leu Lys Ala Ala Ala
    1415

<210> SEQ ID NO 39
<211> LENGTH: 1463
<212> TYPE: PRT
<213> ORGANISM: Artificial sequence
<220> FEATURE:
<223> OTHER INFORMATION: Synthetic sequence

<400> SEQUENCE: 39

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

```
Ser Thr Glu Lys Ser Asn Ile Ile Arg Gly Trp Ile Phe Gly Thr Thr
             85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495
```

```
Val Val Val Leu Ser Phe Glu Leu Leu His Ala Pro Ala Thr Val Cys
            500                 505                 510
Gly Pro Lys Lys Ser Thr Asn Leu Val Lys Asn Lys Cys Val Asn Phe
        515                 520                 525
Asn Phe Asn Gly Leu Thr Gly Thr Gly Val Leu Thr Glu Ser Asn Lys
    530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
            565                 570                 575
Cys Ser Phe Gly Gly Val Ser Val Ile Thr Pro Gly Thr Asn Thr Ser
            580                 585                 590
Asn Gln Val Ala Val Leu Tyr Gln Asp Val Asn Cys Thr Glu Val Pro
        595                 600                 605
Val Ala Ile His Ala Asp Gln Leu Thr Pro Thr Trp Arg Val Tyr Ser
    610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
            645                 650                 655
Ile Cys Ala Ser Tyr Gln Thr Gln Thr Asn Ser Pro Gly Ser Ala Gly
            660                 665                 670
Ser Val Ala Ser Gln Ser Ile Ile Ala Tyr Thr Met Ser Leu Gly Ala
        675                 680                 685
Glu Asn Ser Val Ala Tyr Ser Asn Asn Ser Ile Ala Ile Pro Thr Asn
    690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
            725                 730                 735
Ser Asn Leu Leu Leu Gln Tyr Gly Ser Phe Cys Thr Gln Leu Asn Arg
            740                 745                 750
Ala Leu Thr Gly Ile Ala Val Glu Gln Asp Lys Asn Thr Gln Glu Val
        755                 760                 765
Phe Ala Gln Val Lys Gln Ile Tyr Lys Thr Pro Pro Ile Lys Asp Phe
    770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
            805                 810                 815
Asp Ala Gly Phe Ile Lys Gln Tyr Gly Asp Cys Leu Gly Asp Ile Ala
            820                 825                 830
Ala Arg Asp Leu Ile Cys Ala Gln Lys Phe Asn Gly Leu Thr Val Leu
        835                 840                 845
Pro Pro Leu Leu Thr Asp Glu Met Ile Ala Gln Tyr Thr Ser Ala Leu
    850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
            885                 890                 895
Gly Val Thr Gln Asn Val Leu Tyr Glu Asn Gln Lys Leu Ile Ala Asn
            900                 905                 910
Gln Phe Asn Ser Ala Ile Gly Lys Ile Gln Asp Ser Leu Ser Ser Thr
```

915                 920                 925
Ala Ser Ala Leu Gly Lys Leu Gln Asp Val Val Asn Gln Asn Ala Gln
            930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Gly Gly Glu Ala
                    965                 970                 975
Glu Val Gln Ile Asp Arg Leu Ile Thr Gly Arg Leu Gln Ser Leu Gln
            980                 985                 990
Thr Tyr Val Thr Gln Gln Leu Ile Arg Ala Ala Glu Ile Arg Ala Ser
            995                 1000                1005
Ala Asn Leu Ala Ala Thr Lys Met Ser Glu Cys Val Leu Gly Gln
        1010                1015                1020
Ser Lys Arg Val Asp Phe Cys Gly Lys Gly Tyr His Leu Met Ser
        1025                1030                1035
Phe Pro Gln Ser Ala Pro His Gly Val Val Phe Leu His Val Thr
        1040                1045                1050
Tyr Val Pro Ala Gln Glu Lys Asn Phe Thr Thr Ala Pro Ala Ile
        1055                1060                1065
Cys His Asp Gly Lys Ala His Phe Pro Arg Glu Gly Val Phe Val
        1070                1075                1080
Ser Asn Gly Thr His Trp Phe Val Thr Gln Arg Asn Phe Tyr Glu
        1085                1090                1095
Pro Gln Ile Ile Thr Thr Asp Asn Thr Phe Val Ser Gly Asn Cys
        1100                1105                1110
Asp Val Val Ile Gly Ile Val Asn Asn Thr Val Tyr Asp Pro Leu
        1115                1120                1125
Gln Pro Glu Leu Asp Ser Phe Lys Ala Ser Gly Gly Gly Ser
        1130                1135                1140
Ala Ala Ala Lys Pro Ala Thr Thr Glu Gly Glu Phe Pro Glu Thr
        1145                1150                1155
Arg Glu Lys Met Ser Gly Ile Arg Arg Ala Ile Ala Lys Ala Met
        1160                1165                1170
Val His Ser Lys His Thr Ala Pro His Val Thr Leu Met Asp Glu
        1175                1180                1185
Ala Asp Val Thr Lys Leu Val Ala His Arg Lys Lys Phe Lys Ala
        1190                1195                1200
Ile Ala Ala Glu Lys Gly Ile Lys Leu Thr Phe Leu Pro Tyr Val
        1205                1210                1215
Val Lys Ala Leu Val Ser Ala Leu Arg Glu Tyr Pro Val Leu Asn
        1220                1225                1230
Thr Ala Ile Asp Asp Glu Thr Glu Glu Ile Ile Gln Lys His Tyr
        1235                1240                1245
Tyr Asn Ile Gly Ile Ala Ala Asp Thr Asp Arg Gly Leu Leu Val
        1250                1255                1260
Pro Val Ile Lys His Ala Asp Arg Lys Pro Ile Phe Ala Leu Ala
        1265                1270                1275
Gln Glu Ile Asn Glu Leu Ala Gly Lys Ala Arg Asp Gly Lys Leu
        1280                1285                1290
Thr Pro Gly Glu Met Lys Gly Ala Ser Cys Thr Ile Thr Asn Ile
        1295                1300                1305
Gly Ser Ala Gly Gly Gln Trp Phe Thr Pro Val Ile Asn His Pro
        1310                1315                1320

-continued

```
Glu Val Ala Ile Leu Gly Ile Gly Arg Ile Ala Glu Lys Pro Ile
    1325                1330                1335

Val Arg Asp Gly Glu Ile Val Ala Ala Pro Met Leu Ala Leu Ser
    1340                1345                1350

Leu Ser Phe Asp His Arg Met Ile Asp Gly Ala Thr Ala Gln Lys
    1355                1360                1365

Ala Leu Asn His Ile Lys Arg Leu Leu Ser Asp Pro Glu Leu Leu
    1370                1375                1380

Leu Met Gly Gly Gly Gly Ser Phe Ser Glu Glu Gln Lys Lys Ala
    1385                1390                1395

Leu Asp Leu Ala Phe Tyr Phe Asp Arg Arg Leu Thr Pro Glu Trp
    1400                1405                1410

Arg Arg Tyr Leu Ser Gln Arg Leu Gly Leu Asn Glu Glu Gln Ile
    1415                1420                1425

Glu Arg Trp Phe Arg Arg Lys Glu Gln Gln Ile Gly Trp Ser His
    1430                1435                1440

Pro Gln Phe Glu Lys Gly Ser Ala Lys Phe Val Ala Ala Trp Thr
    1445                1450                1455

Leu Lys Ala Ala Ala
    1460

<210> SEQ ID NO 40
<211> LENGTH: 1306
<212> TYPE: PRT
<213> ORGANISM: Artificial sequence
<220> FEATURE:
<223> OTHER INFORMATION: Synthetic sequence

<400> SEQUENCE: 40

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205
```

Ala Leu Glu Pro Leu Val Asp Leu Pro Ile Gly Ile Asn Ile Thr Arg
210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
            245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
610                 615                 620

-continued

```
Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
            645                 650                 655

Ile Cys Ala Ser Tyr Gln Thr Gln Thr Asn Ser Pro Gly Ser Ala Gly
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
            805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
            835                 840                 845

Pro Pro Leu Leu Thr Asp Glu Met Ile Ala Gln Tyr Thr Ser Ala Leu
850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
            930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Gly Gly Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile Arg Ala Ala Glu Ile Arg Ala Ser
            995                 1000                1005

Ala Asn Leu Ala Ala Thr Lys Met Ser Glu Cys Val Leu Gly Gln
        1010                1015                1020

Ser Lys Arg Val Asp Phe Cys Gly Lys Gly Tyr His Leu Met Ser
        1025                1030                1035
```

-continued

```
Phe Pro Gln Ser Ala Pro His Gly Val Val Phe Leu His Val Thr
    1040            1045            1050

Tyr Val Pro Ala Gln Glu Lys Asn Phe Thr Thr Ala Pro Ala Ile
1055            1060            1065

Cys His Asp Gly Lys Ala His Phe Pro Arg Glu Gly Val Phe Val
    1070            1075            1080

Ser Asn Gly Thr His Trp Phe Val Thr Gln Arg Asn Phe Tyr Glu
    1085            1090            1095

Pro Gln Ile Ile Thr Thr Asp Asn Thr Phe Val Ser Gly Asn Cys
    1100            1105            1110

Asp Val Val Ile Gly Ile Val Asn Asn Thr Val Tyr Asp Pro Leu
    1115            1120            1125

Gln Pro Glu Leu Asp Ser Phe Lys Ala Ser Gly Gly Gly Gly Ser
    1130            1135            1140

Asp Ile Ile Lys Leu Leu Asn Glu Gln Val Asn Lys Glu Met Gln
    1145            1150            1155

Ser Ser Asn Leu Tyr Met Ser Met Ser Ser Trp Cys Tyr Thr His
    1160            1165            1170

Ser Leu Asp Gly Ala Gly Leu Phe Leu Phe Asp His Ala Ala Glu
    1175            1180            1185

Glu Tyr Glu His Ala Lys Lys Leu Ile Ile Phe Leu Asn Glu Asn
    1190            1195            1200

Asn Val Pro Val Gln Leu Thr Ser Ile Ser Ala Pro Glu His Lys
    1205            1210            1215

Phe Glu Gly Leu Thr Gln Ile Phe Gln Lys Ala Tyr Glu His Glu
    1220            1225            1230

Gln His Ile Ser Glu Ser Ile Asn Asn Ile Val Asp His Ala Ile
    1235            1240            1245

Lys Ser Lys Asp His Ala Thr Phe Asn Phe Leu Gln Trp Tyr Val
    1250            1255            1260

Ala Glu Gln His Glu Glu Glu Val Leu Phe Lys Asp Ile Leu Asp
    1265            1270            1275

Lys Ile Glu Leu Ile Gly Asn Glu Asn His Gly Leu Tyr Leu Ala
    1280            1285            1290

Asp Gln Tyr Val Lys Gly Ile Ala Lys Ser Arg Lys Ser
    1295            1300            1305
```

STABILIZED CORONAVIRUS SPIKE (S) PROTEIN IMMUNOGENS AND RELATED VACCINES

CROSS-REFERENCE TO RELATED APPLICATIONS

The subject patent application is a continuation of U.S. patent application Ser. No. 17/019,825 (filed Sep. 14, 2020; now pending), which claims the benefit of priority to U.S. Provisional Patent Application No. 63/045,557 (filed Jun. 29, 2020). The full disclosures of the priority applications are incorporated herein by reference in their entirety and for all purposes.

STATEMENT OF GOVERNMENT SUPPORT

This invention was made with government support under grant numbers AI139092 and AI137472 awarded by the National Institutes of Health. The government has certain rights in the invention.

BACKGROUND OF THE INVENTION

Coronaviruses (CoV) are enveloped viruses with a positive-stranded RNA genome. In 2002, there was an outbreak of severe acute respiratory syndrome (SARS) in Asia. In 2003, a novel coronavirus was identified to be the causative agent of SARS and subsequently named SARS-CoV. During the 2002-2003 outbreak, SARS-CoV infected over 8000 people with ~10% fatality rate. In 2012, another coronavirus, Middle East respiratory syndrome coronavirus (MERS-CoV), was identified. Since 2012, MERS-CoV has infected over 2000 people in 27 countries with ~35% fatality rate. In December 2019, a novel coronavirus designated as 2019-nCoV (or SARS-CoV-2) appeared in Wuhan, China. The first reported infected individuals, some of whom showed symptoms as early as December 8, were discovered to be among stallholders from the Wuhan South China Seafood Market. On Jan. 10, 2020, gene sequencing determined that this novel coronavirus, a β-coronavirus, is related to the MERS-CoV and the SARS-CoV. On Jan. 30, 2020, the WHO declares SARS-CoV-2 a public health emergency of international concern (PHEIC), and on Mar. 11, 2020, characterized the situation as a pandemic. On May 24, 2020, the WHO Coronavirus Disease (COVID-19) Dashboard showed a total of 5,304,772 confirmed cases in 216 countries, areas or territories, including 342,029 deaths. SARS-CoV, MERS-CoV, and SARS-CoV-2 belong to the β-coronavirus genus and are highly pathogenic zoonotic viruses. In addition to these three highly pathogenic β-coronaviruses, four low-pathogenicity β-coronaviruses, HCoV-OC43, HCoVHKU1, HCoV-NL63 and HCoV-229E, are also endemic in humans.

To date, no therapeutics or vaccines have been approved for treating or preventing any human-infecting coronaviruses. There is a strong and urgent need in the art for effective vaccines against coronaviruses. The present invention is directed to this and other pressing needs in the art.

SUMMARY OF THE INVENTION

In one aspect, the invention provides engineered immunogen polypeptides that are derived or modified from the spike (S) glycoprotein of coronaviruses including SARS-CoV, MERS-CoV and SARS-CoV-2. Relative to a wildtype soluble S protein sequence of the coronavirus, the immunogen polypeptides of the invention contain an altered soluble S sequence with modifications that stabilize the prefusion S structure. In various embodiments, the modifications include (a) a mutation that inactivates the S1/S2 cleavage site, and (b) a mutation in the turn region between the heptad repeat 1 (HR1) region and the central helix (CH) region (see FIG. 1) that prevents HR1 and CH to form a straight helix during membrane fusion process. In some embodiments, the immunogen polypeptides of the invention also contain truncation of the heptad repeat 2 region (HR2) in addition to the stabilizing mutations noted above.

Some soluble S immunogen polypeptides of the invention are derived from SARS-CoV-2. In some of these embodiments, the mutation inactivating S1/S2 cleavage site can contain substitution of $^{682}$RRAR$^{685}$ (SEQ ID NO:19) with GSAG (SEQ ID NO:20), and the mutation in the turn region can contain double mutation K986G/V987G, K986P/V987P, K986G/V987P or K986P/V987G, using amino acid numbering based on cryo-EM model PDB ID 6VSB as reference. In some embodiments, the wildtype soluble S sequence contains the sequence shown in SEQ ID NO:14, or a substantially identical or conservatively modified variant thereof. In some embodiments, truncation of HR2 entails deletion of the residues shown in SEQ ID NO:9 at the C-terminus of the wildtype soluble S sequence. In some of these embodiments, the immunogen polypeptides can further include truncation of residues shown in SEQ ID NO:10 at the C-terminus. In some of these embodiments, the immunogen polypeptides contain substitution of residues shown in SEQ ID NO:10 at the C-terminus of the wildtype soluble S sequence with residues GNS.

In some embodiments, the SARS-CoV-2 derived immunogen polypeptides of the invention can contain a N-terminal leader sequence shown in SEQ ID NO:15. In some embodiments, the immunogen polypeptide can further include in the region of HR1 that interacts with HR2 (a) one or more proline or glycine substitutions, and/or (b) insertion of one or more amino acid residues. In some of these embodiments, the immunogen polypeptide can have one or more substitutions selected from A942P, S943P, A944P, A942G, S943G and A944G. In some of these embodiments, the insertion can be insertion of G or GS between any residues in A942-A944. In some exemplified embodiments, the SARS-CoV-2 derived immunogen polypeptides of the invention contain the sequence shown in any one of SEQ ID NOs:32-37, or a substantially identical or conservatively modified variant thereof.

Some soluble S immunogen polypeptides of the invention are derived from SARS-CoV. In some of these embodiments, the mutation inactivating S1/S2 cleavage site can be R667G substitution, and the mutation in the turn region comprises double mutation K968G/V969G, K968P/V969P, K968G/V969P or K968P/V969G, using amino acid numbering based on UniProt ID P59594 as reference. In some embodiments, the wildtype soluble S sequence contains the sequence shown in SEQ ID NO:7, or a substantially identical or conservatively modified variant thereof. In some embodiments, the SARS-CoV derived immunogen polypeptides of the invention contain truncation of HR2 (SEQ ID NO:9) at the C-terminus of the wildtype soluble S sequence. In some of these embodiments, immunogen polypeptides can additionally include truncation of residues shown in SEQ ID NO:10 at the C-terminus. In some of these embodiments, the immunogen polypeptides contain substitution of residues shown in SEQ ID NO:10 at the C-terminus of the wildtype soluble S sequence with residues GNS.

In some embodiments, the SARS-CoV derived immunogen polypeptides of the invention can contain a N-terminal leader sequence shown in SEQ ID NO:8. In some embodiments, the immunogen polypeptides can further include in the region of HR1 that interacts with HR2 (a) one or more proline or glycine substitutions, and/or (b) insertion of one or more amino acid residues. In some of these embodiments, the immunogen polypeptide can have one or more substitutions selected from S924P, T925P, A926P, S924G, T925G, and A926G. In some of these embodiments, the insertion can be insertion of G or GS after any residue in S924-A926.

Some other soluble S immunogen polypeptides of the invention are derived from MERS-CoV. In some of these embodiments, the mutation inactivating S1/S2 cleavage site can contain R748A/R751G double mutation, and the mutation in the turn region comprises double mutation V1060G/L1061G, V1060P/L1061P, V1060G/L1061P or V1060P/L1061G, using amino acid numbering based on UniProt ID R9UQ53 as reference. In some embodiments, the wildtype soluble S sequence contains the sequence shown in SEQ ID NO:11 or a substantially identical or conservatively modified variant thereof. In some embodiments, MERS-CoV derived immunogen polypeptides of the invention contain truncation of HR2 (SEQ ID NO:13) at the C-terminus of the wildtype soluble S sequence.

In some embodiments, the MERS-CoV derived immunogen polypeptides of the invention can contain a N-terminal leader sequence shown in SEQ ID NO:12. In some embodiments, the immunogen polypeptides can further include in the region of HR1 that interacts with HR2 (a) one or more proline or glycine substitutions in the region of HR1 that interacts with HR2 in the region of HR1 that interacts with HR2 in the region of HR1 that interacts with HR2, and/or (b) insertion of one or more amino acid residues. In some of these embodiments, the immunogen polypeptide can have one or more substitutions selected from T1013P, T1014P, T1015P, T1013G, T1014G and T1015G. In some of these embodiments, the insertion can be insertion of residue G or GS after any residue in T1013-T1015.

In some embodiments, the coronavirus S protein derived immunogen polypeptides of the invention can additionally include a trimerization motif at the C-terminus. In some of these embodiments, the trimerization motif is foldon or viral capsid protein SHP. In various embodiments, the employed trimerization motif can contain the foldon sequence shown in SEQ ID NO:26 or the SHP sequence shown in SEQ ID NO:27, or a substantially identical or conservatively modified variant thereof. In some embodiments, the coronavirus S protein derived immunogen polypeptides of the invention can additionally contain the subunit sequence of a self-assembling nanoparticle that is fused to the altered soluble S sequence. In some of these embodiments, C-terminus of the altered soluble S sequence is fused to N-terminus of the nanoparticle subunit sequence.

In another aspect, the invention provides polynucleotide sequences that encode the coronavirus S protein derived immunogen polypeptides described herein. Some of the polynucleotide sequences encode a fusion polypeptide containing the immunogen polypeptide that is fused at its C-terminus to the N-terminus of the subunit sequence of a self-assembling nanoparticle.

In another aspect, the invention provides coronavirus vaccine compositions that contain an immunogen polypeptide described herein that is displayed on the surface of a self-assembling nanoparticle. In some of these embodiments, the self-assembling nanoparticle contains a trimeric sequence, and C-terminus of the immunogen polypeptide is fused to N-terminus of the subunit sequence of the nanoparticle. In some embodiments, the employed self-assembling nanoparticle is composed of ferritin, E2p or I3-01. Some nanoparticle vaccines of the invention display an engineered SARS-CoV-2 spike protein described herein.

In some embodiments, the nanoparticle vaccine contains (1) a polypeptide sequence containing from N terminus to C terminus (a) an engineered SARS-CoV-2 spike polypeptide, a GS linker sequence, and nanoparticle sequence I3-01v9, (b) an engineered SARS-CoV-2 spike polypeptide, a GS linker sequence, and nanoparticle sequence E2p, or (c) an engineered SARS-CoV-2 spike polypeptide, a GS linker sequence, and nanoparticle sequence ferritin; or (2) a conservatively modified variant of the polypeptide sequence. In some of these embodiments, the displayed SARS-CoV-2 spike immunogen polypeptide contains, relative to the wildtype spike sequence, (a) substitution of the S1/S2 cleavage site $^{682}$RRAR$^{685}$ (SEQ ID NO:19) with GSAG (SEQ ID NO:20), (b) double mutations K986G/V987G in the turn region, and (c) truncation of HR2 (SEQ ID NO:9) at the C-terminus.

In some nanoparticle scaffolded SARS-CoV-2 vaccines of the invention, the displayed SARS-CoV-2 spike immunogen polypeptide contains the sequence shown in SEQ ID NO:33 or 34, or a conservatively modified variant thereof. In some of these embodiments, the scaffolded vaccine is composed of (1) a subunit sequence containing from N terminus to C terminus (a) the engineered SARS-CoV-2 spike polypeptide shown in SEQ ID NO:33, linker sequence $(G_4S)_2$ (SEQ ID NO:22), nanoparticle sequence shown in SEQ ID NO:23 (I3-01v9), locking domain shown in SEQ ID NO:29 (LD7), and T cell epitope shown in SEQ ID NO:30 (PADRE), (b) the engineered SARS-CoV-2 spike polypeptide shown in SEQ ID NO:33, linker sequence $G_4S$ (SEQ ID NO:21), nanoparticle subunit sequence shown in SEQ ID NO:24 (E2p), locking domain shown in SEQ ID NO:28 (LD4), and T cell epitope shown in SEQ ID NO:30 (PADRE), or (c) the engineered SARS-CoV-2 spike polypeptide shown in SEQ ID NO:33, linker sequence $G_4S$ (SEQ ID NO:21), nanoparticle sequence shown in SEQ ID NO:25 (ferritin); or (2) a conservatively modified variant of the subunit sequence. In some embodiments, the subunit of the nanoparticle scaffolded vaccines contains the sequence shown in any one of SEQ ID NOs:38-40, or a substantially identical or conservatively modified variant thereof.

In still another aspect, the invention provides pharmaceutical compositions that contain the vaccine composition described herein, and a pharmaceutically acceptable carrier. In another aspect, the invention provides methods for preventing or treating a coronavirus infection in a subject. These methods involve administering to the subject a pharmaceutically effective amount of a vaccine composition or a pharmaceutical composition described herein.

A further understanding of the nature and advantages of the present invention may be realized by reference to the remaining portions of the specification and claims.

DESCRIPTION OF THE DRAWINGS

FIG. 3 shows results from SARS-CoV-2 vaccine-induced antibody responses in mice. SARS-CoV-2 spike/spike-NP vaccine-induced binding antibody response. Listed in the figure are a summary of $ED_{50}$ titers measured for five SARS-CoV-2 spike-based vaccine groups (S2P-5GS-1TD0, S2GΔHR2-5GS-1TD0, S2GΔHR2-5GS-FR, S2GΔHR2-5GS-E2p-L4P, and S2GΔHR2-10GS-I3-01v9-L7P) against three coating antigens in ELISA. $ED_{50}$ values were calculated in GraphPad Prism 8.4.3. Of note, the $ED_{50}$ values at w2 were derived by setting the lower/upper constraints of $OD_{450}$ at 0.0/3.2 to achieve greater accuracy.

FIG. 4 shows additional results from SARS-CoV-2 vaccine-induced antibody responses in mice. Listed in the figure are a summary of $ID_{50}$ titers measured for five SARS-CoV-2 spike-based vaccine groups (S2P-5GS-1TD0, S2GΔHR2-5GS-1TD0, S2GΔHR2-5GS-FR, S2GΔHR2-5GS-E2p-L4P, and S2GΔHR2-10GS-I3-01v9-L7P) against two pseudoviruses, SARS-CoV-1-pp and SARS-CoV-2-pp, in neutralization assays. $ID_{50}$ values were calculated in GraphPad Prism 8.4.3, with the lower/upper constraints of % neutralization set at 0.0/100.0.

DETAILED DESCRIPTION

I. Overview

Figure 1:
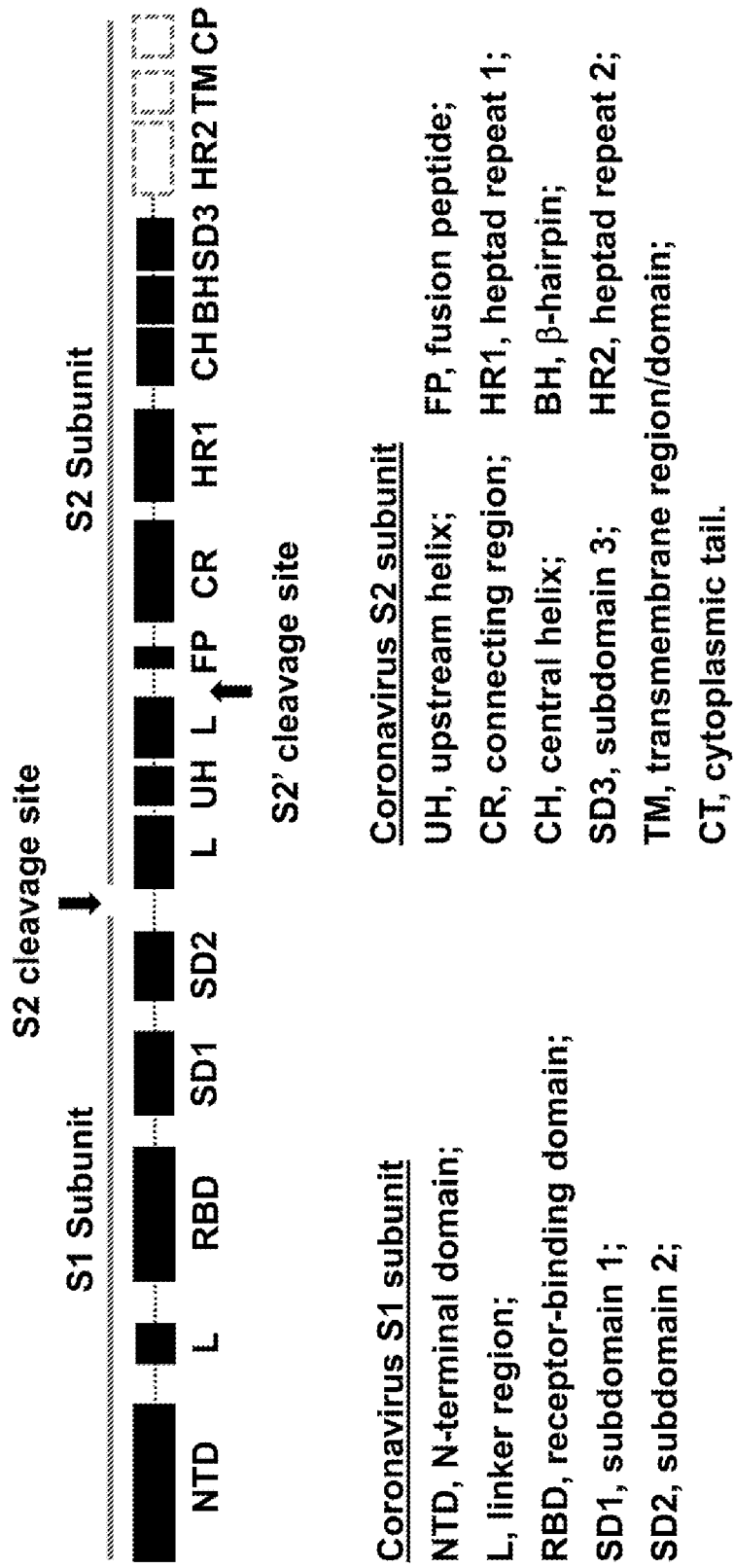
FIG. 1 illustrates the organization of different structural motifs of coronaviral spike (S) protein. The scheme shown in the figure reflects the structure of S protein of different coronaviruses encompassed by the invention, e.g., SARS-CoV, MERS-CoV and SARS-CoV-2. The structural domains and motifs of the S protein shown in the figure include RBD, HR1, CH1 and HR2 domains or regions, as well as the S2 cleavage site (aka S1/S2 cleavage site) and the S2' cleavage site. In addition to the various S structural components indicated in the figure, the amino acid residues between HR1 and CH are denoted "the turn region" herein.

For SARS-CoV (aka SARS-CoV-1), MERS-CoV, and SARS-CoV-2, the viral genome encodes spike (S), envelope (E), membrane (M), and nucleocapsid (N) structural proteins, among which the S glycoprotein is responsible for binding the host receptor via the receptor-binding domain (RBD) in its S1 subunit, as well as the subsequent membrane fusion and viral entry driven by its S2 subunit. A possible membrane fusion process has been proposed. The receptor binding may help to keep the RBD in a 'standing' state, which facilitates the dissociation of the S1 subunit from the S2 subunit. When the S1 subunit is dissociated from the S2 subunit, a second S2' cleavage can release the fusion peptide. The connecting region, HR1 region and central helix would form an extremely long helix (≥200 Å) to insert the fusion peptide into the host cell membrane. Finally, the HR1 and HR2 regions will form a coiled structure and assemble into a six-helix bundle to merge the viral and host membranes.

In all the prefusion S structures solved for SARS-CoV, MERS-CoV, and SARS-CoV-2, the viral membrane proximal HR2 region is invisible, indicating high mobility in HR2. The RBD contains a core subdomain and a receptor-binding motif (RBM). While the core subdomains are highly similar between the three coronaviruses, their RBMs are markedly different, leading to different receptor specificity: SARS-CoV and SARS-CoV-2 recognize the angiotensin-converting enzyme 2 (ACE2), whereas MERS-CoV binds the dipeptidyl peptidase 4 (DPP4). As the S glycoprotein is surface-exposed and mediates entry into host cells, it is the main target of neutralizing antibodies (NAbs) upon infection and the focus of vaccine design. S trimers are extensively decorated with N-linked glycans that are important for proper folding and for modulating accessibility to NAbs.

The present invention is predicated in part on the studies undertook by the inventors to design nanoparticle vaccines for three highly pathogenic β-coronaviruses, SARS-CoV, MERS-CoV, and SARS-CoV-2 based on two rational strategies. In the first strategy, the inventors aimed to stabilize the S trimer in a prefusion conformation by eliminating the causes of metastability in various regions of S, particularly HR1 and in HR2, prior to displaying it on nanoparticles. In the second vaccine strategy, the inventors utilized the SpyTag/SpyCatcher protein superglue system to create RBD-presenting nanoparticles. A number of S protein derived immunogen polypeptides and nanoparticle vaccine constructs were generated based on the design and examined for activities.

As exemplified herein with SARS-CoV-2 (and SARS-CoV-1) spike protein, the engineered spike immunogen polypeptides of the invention are more stable and represent more optimal vaccine design relative to the control polypeptides devoid of the engineering. Their advantageous biochemical and structural properties as described herein indicate that they are amenable for rapid and large-scale vaccine production in the industrial setting. When examined in vivo, it was found that the engineered SARS-CoV-2 spike immunogens (e.g., S2GΔHR2) are more effective than the non-engineered control protein to elicit potent anti-SARS-CoV-2 NAb responses, alone or presented on self-assembling nanoparticle platforms (SApNPs). As detailed in the Examples herein, the exemplified nanoparticle vaccines of the invention, e.g., S2GΔHR2-presenting I3-01v9 SApNP, can also elicit a strong Th1 response as well as other types of T-cell response needed for protective cellular immunity. Results obtained from the exemplified studies herein on the SARS-CoV-2 spike protein indicate that the engineered spike immunogen polypeptides of the invention provide more effective next-generation vaccine candidates for evaluation in human trials.

The invention provides coronavirus immunogens and vaccine compositions in accordance with the studies and exemplified designs described herein. Related polynucleotide sequences, expression vectors and pharmaceutical compositions are also provided in the invention. In various embodiments, stabilized S trimers and RBD proteins, in the forms of protein or nucleic acid (DNA/mRNA) carried by a viral vector can be used as coronavirus vaccines. In addition, nanoparticles presenting stabilized S trimers and RBDs can be used as VLP-type coronavirus vaccines.

The coronavirus S-protein based immunogens and vaccines of the invention have several advantageous properties. The S trimer designs described herein, which present conserved neutralizing epitopes in their native-like conformation, enable S trimers to be used as vaccine antigens or displayed multivalently on nanoparticles. Nanoparticle vaccines of the invention allows S trimers derived from the three different coronaviruses to be displayed on well-known nanoparticle platforms, such as ferritin, E2p, and I3-01 with a size ranging from 12.2 to 25.0 nm. In addition, the use of high-stability hollow nanocages (E2p and 1VLW/I3-01 variants allows engineering of locking domains (LD), T-cell epitopes (e.g. PADRE), and peptide adjuvants within the nanocage, thus providing an all-in-one vaccine solution. All S trimer-presenting nanoparticles can be produced in ExpiCHO cells with high yield. Since CHO is one of the principal mammalian cell lines used for industrial manufacture of protein therapeutics and vaccines and ExpiCHO is a transient version of this CHO cell line, nanoparticles obtained from the ExpiCHO production are expected to have the same properties as those from industrial CHO production. Moreover, the high yield of S-presenting nanoparticles produced in ExpiCHO cells with antibody and SEC purification a will enable the development of a simple, robust, and cost-effective manufacturing process for industrial production.

Unless otherwise specified herein, the vaccine immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y. ($3^{rd}$ ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

Unless otherwise noted, the expression "at least" or "at least one of" as used herein includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

Unless otherwise noted, the order of steps or order for performing certain actions is immaterial so long as the present invention remain operable. Moreover, two or more steps or actions may be conducted simultaneously.

Unless otherwise noted, the use of any and all examples, or exemplary language herein, for example, "such as" or "including," is intended merely to illustrate better the present invention and does not pose a limitation on the scope of the invention. No language in the specification should be construed as indicating any non-claimed element as essential to the practice of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this invention are provided herein.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein. Unless otherwise noted, the term "vaccine immunogen" is used interchangeably with "protein antigen" or "immunogen polypeptide".

The term "conservatively modified variant" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as pneumonia. For instance, this can be the amount necessary to inhibit viral replication or to measurably alter outward symptoms of the viral infection. In general, this amount will be sufficient to measurably inhibit virus (for example, SARS-CoV-2) replication or infectivity. When administered to a subject, a dosage will generally be used that will achieve target tissue concentrations that has been shown to achieve in vitro inhibition of viral replication. In some embodiments, an "effective amount" is one that treats (including prophylaxis) one or more symptoms and/or underlying causes of any of a disorder or disease, for example to treat a coronavirus infection. In some embodiments, an effective amount is a therapeutically effective amount. In some embodiments, an effective amount is an amount that prevents one or more signs or symptoms of a particular disease or condition from developing, such as one or more signs or symptoms associated with coronaviral infections.

Unless otherwise noted, a fusion protein is a recombinant protein containing amino acid sequence from at least two unrelated proteins that have been joined together, via a peptide bond, to make a single protein. Thus, it does not encompass the naturally existing coronaviruses surface antigen that is termed fusion (F) protein as described herein. The unrelated amino acid sequences can be joined directly to each other or they can be joined using a linker sequence. As used herein, proteins are unrelated, if their amino acid sequences are not normally found joined together via a peptide bond in their natural environment (e.g., inside a cell). For example, the amino acid sequences of bacterial enzymes such as *B. stearothermophilus* dihydrolipoyl acyltransferase (E2p) and the amino acid sequences of a soluble coronavirus S glycoprotein are not normally found joined together via a peptide bond.

Immunogen is a protein or a portion thereof that is capable of inducing an immune response in a mammal, such as a mammal infected or at risk of infection with a pathogen. Administration of an immunogen can lead to protective immunity and/or proactive immunity against a pathogen of interest.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

SpyCatcher-SpyTag refers to a protein ligation system that is based on based on the internal isopeptide bond of the CnaB2 domain of FbaB, a fibronectin-binding MSCRAMM and virulence factor of *Streptococcus pyogenes*. See, e.g., Terao et al., J. Biol. Chem. 2002; 277:47428-47435; and Zakeri et al., Proc. Natl. Acad. Sci. USA. 2012; 109:E690-E697. It utilizes a modified domain from a *Streptococcus pyogenes* surface protein (SpyCatcher), which recognizes a cognate 13-amino-acid peptide (SpyTag). Upon recognition, the two form a covalent isopeptide bond between the side chains of a lysine in SpyCatcher and an aspartate in SpyTag. This technology has been used, among other applications, to create covalently stabilized multi-protein complexes, for modular vaccine production, and to label proteins (e.g., for microscopy). The SpyTag system is versatile as the tag is a short, unfolded peptide that can be genetically fused to exposed positions in target proteins; similarly, SpyCatcher can be fused to reporter proteins such as GFP, and to epitope or purification tags.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., A CORONAVIRUS infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In some embodiments of the invention, vaccines or vaccine immunogens or vaccine compositions are expressed from fusion constructs and self-assemble into nanoparticles displaying an immunogen polypeptide or protein on the surface.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

A self-assembling nanoparticle refers to a ball-shape protein shell with a diameter of tens of nanometers and well-defined surface geometry that is formed by identical copies of a non-viral protein capable of automatically assembling into a nanoparticle with a similar appearance to VLPs. Known examples include ferritin (FR), which is conserved across species and forms a 24-mer, as well as *B. stearothermophilus* dihydrolipoyl acyltransferase (E2p), *Aquifex aeolicus* lumazine synthase (LS), and *Thermotoga maritima* encapsulin, which all form 60-mers. Self-assembling nanoparticles can form spontaneously upon recombinant expression of the protein in an appropriate expression system. Methods for nanoparticle production, detection, and characterization can be conducted using the same techniques developed for VLPs.

III. Redesigned Coronavirus Soluble S Immunogens

The invention provides redesigned or modified soluble S sequences of coronaviruses that can be employed for generating vaccine compositions. The redesigned soluble S trimer immunogens or proteins are stabilized by introducing modifications into the wildtype soluble S sequences of coronaviruses. Some specific wildtype soluble S sequences of specific SARS-CoV, MERS-CoV and SARS-CoV-2 strains or isolates are exemplified herein, e.g., SE ID NOs: 1-3. Due to functional similarity and sequence homology among different isolates or strains of a given coronavirus, redesigned soluble S immunogens derived from other known coronavirus S protein ortholog sequences can also be generated in accordance with the redesign strategy described herein. There are many known coronavirus S protein sequences that have been described in the literature. See, e.g., James et al., J. Mol. Biol. 432:3309-25, 2020; Andersen et al., Nat. Med. 26:450-452, 2020; Walls et al., Cell 180:281-292, 2020; Zhang et al., J. Proteome Res. 19:1351-1360, 2020; Du et al., Expert Opin. Ther. Targets 21:131-143; 2017; Yang et al., Viral Immunol. 27:543-550, 2014; Wang et al., Antiviral Res. 133:165-177, 2016; Bosch et al., J. Virol. 77:8801-8811, 2003; Lio et al., TRENDS Microbiol. 12:106-111, 2004; Chakraborti et al., Virol. J. 2:73, 2005; and Li, Ann. Rev. Virol. 3:237-261, 2016.

As detailed herein, some redesigned soluble S immunogen polypeptides of the invention contain mutations that can enhance stability of the prefusion S structure. These include mutations that inactivate the S1/S2 cleavage site, and mutations in HR1 that remove any strain in the turn region between HR1 and CH, i.e., to prevent the formation of a straight helix during fusion. In some embodiments, the resigned soluble S immunogen polypeptides can additionally contain a truncation of the HR2 motif. Truncation of the HR2 domain leads to disruption of the HR1/HR2 fusion core and stabilizes the prefusion S structure.

Some engineered soluble S immunogen polypeptides are derived from a SARS-CoV-2 virus which caused COVID-19. Some of these polypeptides contain a modified S1/S2 cleavage site. As exemplification, the wildtype soluble S sequence to be used for engineering the SARS-CoV-2 immunogen polypeptides of the invention is shown in SEQ ID NO:3 or N-terminal leader truncated soluble S sequence (SEQ ID NO:14). In other embodiments, the wildtype S sequence to be used can be a variant of SEQ ID NO:3 or 14, e.g., a substantially identical or conservatively modified variant thereof. Using amino acid numbering based on cryo-EM model PDB ID 6VSB or GenBank accession number MN908947.3 as reference, the modified cleavage site contains $^{682}$GSAGSV$^{687}$ (SEQ ID NO:18). Inactivation of this cleavage site can be achieved by a number of sequence alterations (e.g., deletions or substitutions) within or around the site. One mutation that inactivates the cleavage site without otherwise impacting the structure of the protein is substitution of residues $^{682}$RRAR$^{685}$ (SEQ ID NO:19) of the cleavage site with GSAG (SEQ ID NO:20), as exemplified herein. In addition to inactivation of the cleavage site, the soluble SARS-CoV-2 immunogen polypeptides can additionally contain a double mutation in the HR1 region that remove strain in the turn region (between HR1 and CH motifs) during fusion by preventing the formation of a straight helix. In various embodiments, this double mutation can be K986G/V987G, K986P/V987P, K986G/V987P or K986P/V987G.

Additional or alternative to the above-noted mutations that stabilize prefusion S structure, some SARS-CoV-2 immunogen polypeptides of the invention can contain a deletion of a substantial portion of or the entire HR2 domain. Using the exemplified soluble SARS-CoV-2 S sequence SEQ ID NO:3 to illustrate, this deletion can encompass amino acid residues 1150-1208 (SEQ ID NO:9). In various other embodiments, the deletion can be a truncation of the first 35, 40, 45, 50, 55 or more C-terminal residues of SEQ ID NO:3. In still some other embodiments, the C-terminal truncation of the wildtype soluble S sequence can extend beyond the HR2 domain. In some of these embodiments, one or more residues in the region consisting residues 1139-1149 (SEQ ID NO:10) of SEQ ID NO:3 can also be deleted. In some of these embodiments, the C-terminally truncated soluble S sequence can contain an inserted tripeptide motif, GNS, e.g., by substitution of residues 1139-1149 of SEQ ID NO:3 with this motif. As described herein, this tripeptide motif functions to increase protein yield when the immunogen polypeptide is displayed on nanoparticles. In some other embodiments, the soluble S sequence can include the N-terminal leader sequence shown in SEQ ID NO:15.

In some SARS-CoV-2 immunogen polypeptides of the invention, additional mutations of the wildtype soluble S sequence can be introduced to destabilize the postfusion S structure. In some embodiments, one or more proline and/or glycine substitution can be engineered in the region of HR1 that interacts with HR2 to form the fusion core. These mutations function to disrupt the six-helix-bundle fusion core. In various embodiments, the mutations can include A942P, S943P, A944P, A942G, S943G and A944G. In some embodiments, one or more extra amino acid residues can be inserted into the region of HR1 that interacts with HR2 to form the fusion core. Similarly, these insertions also function to disrupt helical pattern of the fusion core. In various embodiments, the insertions can include insertion of G or GS between any residues in A942-A944.

As detailed in the Examples herein, several specific engineered SARS-CoV-2 spike immunogen polypeptides have demonstrated enhanced immunogenic properties relative to the wildtype SARS-CoV-2 spike ectodomain polypeptide or a well-known SARS-CoV-2 spike polypeptide containing a double-proline mutation ("S2P"). One of these exemplified SARS-CoV-2 spike polypeptides is S2GΔHR2 shown in SEQ ID NO:32. Relative to the wildtype SARS-CoV-2 spike ectodomain sequence (SEQ ID NO:3), S2GΔHR2 contains substitution of the S1/S2 cleavage site sequence $^{682}$RRARSV$^{687}$ (SEQ ID NO:31) replaced with GSAGSV (SEQ ID NO:18). It also contains a K986G/V987G double mutation in HR1. Additionally, it has the HR2 region (E1150-Q1208) removed. As described herein, this engineered SARS-CoV-2 spike immunogen polypeptide produced high-purity trimers, indicating a substantial reduction of spike metastability. It also displayed higher affinity for representative mAbs specific for the spike in both ELISA and bio-layer interferometry (BLI) assays. When displayed on self-assembling nanoparticle scaffolds, this engineered protein showed satisfactory yield, purity, stability in production, and structural integrity whereas the wild-type spike and the widely used spike with a double proline mutation failed to express on any NP scaffold. The NP displayed S2GΔHR2 also showed improved antigenicity when tested against a panel of mAbs/Nabs. When examined in vivo, NP vaccines displaying this engineered spike also elicited neutralizing antibody responses that are up-to-10-folds stronger than the control NPs.

Sequence of engineered SARS-CoV-2 spike protein "S2GΔHR2" (SEQ ID NO:32) is shown below. In the sequence, the N-terminal leader is italicized, the mutated S1/S2 cleavage site is underlined, and the substituted $^{986}$GG$^{987}$ residues are underlined and italicized.

*MFVFLVLLPLVSS*

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

-continued

SSANNCTFEYVSQPPFLMDLEGKQGNFKNLREFVFKNIDGYFKIYSKHTP

INLVRDLPQGFSALEPLVDLPIGINITRFQTLLALHRSYLTPGDSSSGW

TAGAAAYYVGYLQPRTFLLKYNENGTITDAVDCALDPLSETKCTLKSFT

VEKGIYQTSNFRVQPTESIVRFPNITNLCPFGEVFNATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGV

GYQPYRVVVLSFELLHAPATVCGPKKSTNLVKNKCVNFNFNGLTGTGVL

TESNKKFLPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPG<u>SAGS</u>VASQSIIAYTMSL

GAENSVAYSNNSIAIPTNFTISVTTEILPVSMTKTSVDCTMYICGDSTE

CSNLLLQYGSFCTQLNRALTGIAVEQDKNTQEVFAQVKQIYKTPPIKDF

GGFNFSQILPDPSKPSKRSFIEDLLFNKVTLADAGFIKQYGDCLGDIAA

RDLICAQKFNGLTVLPPLLTDEMIAQYTSALLAGTITSGWTFGAGAALQ

IPFAMQMAYRFNGIGVTQNVLYENQKLIANQFNSAIGKIQDSLSSTASA

LGKLQDVVNQNAQALNTLVKQLSSNFGAISSVLNDILSRLD<u>GG</u>EAEVQI

DRLITGRLQSLQTYVTQQLIRAAEIRASANLAATKMSECVLGQSKRVDF

CGKGYHLMSFPQSAPHGVVFLHVTYVPAQEKNFTTAPAICHDGKAHFPR

EGVFVSNGTHWFVTQRNFYEPQIITTDNTFVSGNCDVVIGIVNNTVYDP

LQPELDSFK

Some engineered soluble S immunogen polypeptides are derived from a SARS-CoV virus. Some of these polypeptides contain a modified S1/S2 cleavage site. As exemplification, the wildtype soluble S sequence to be used for engineering the SARS-CoV immunogen polypeptides of the invention is shown in SEQ ID NO:1 or N-terminal leader truncated soluble S sequence (SEQ ID NO:7). In other embodiments, the wildtype S sequence to be used can be a variant of SEQ ID NO:1 or 7, e.g., a substantially identical or conservatively modified variant thereof. Using amino acid numbering based on UniProt ID P59594 or GenBank accession number NP_828851 as reference, the modified sequence can contain a R667G substitution, which leads to inactivation of the S1/S2 cleavage site. In addition to inactivation of the cleavage site, the soluble SARS-CoV immunogen polypeptides can additionally a double mutation in the HR1 region that remove strain in the turn region by preventing the formation of a straight helix during fusion. In various embodiments, this double mutation can be K968G/V969G, K968P/V969P, K968G/V969P or K968P/V969G.

Additional or alternative to the above-noted mutations that stabilize prefusion S structure, some SARS-CoV immunogen polypeptides of the invention can contain a deletion of a substantial portion of or the entire HR2 domain. Using the exemplified soluble SARS-CoV S sequence SEQ ID NO:1 to illustrate, this deletion can encompass amino acid residues 1132-1190 (SEQ ID NO:9). In various other embodiments, the deletion can be a truncation of the first 35, 40, 45, 50, 55 or more C-terminal residues of SEQ ID NO:1. In still some other embodiments, the C-terminal truncation of the wildtype soluble S sequence can extend beyond the HR2 domain. In some of these embodiments, one or more residues in the region consisting residues 1121-1131 (SEQ ID NO:10) of SEQ ID NO:1 can also be deleted. In some of these embodiments, the C-terminally truncated soluble S sequence can contain an inserted tripeptide motif, GNS, e.g., by substitution of residues 1121-1131 of SEQ ID NO:1 with this motif. As described herein, this tripeptide motif functions to increase protein yield when the immunogen polypeptide is displayed on nanoparticles. In some other embodiments, the soluble S sequence can have the N-terminal leader sequence truncated.

In some SARS-CoV immunogen polypeptides of the invention, additional mutations of the wildtype soluble S sequence can be introduced to destabilize the postfusion S structure. In some embodiments, one or more proline and/or glycine substitution can be engineered in the region of HR1 that interacts with HR2 to form the fusion core. These mutations function to disrupt the six-helix-bundle fusion core. In various embodiments, the mutations can include S924P, T925P, A926P, S924G, T925G, and A926G. In some embodiments, one or more extra amino acid residues can be inserted into the region of HR1 that interacts with HR2 to form the fusion core. Similarly, these insertions also function to disrupt helical pattern of the fusion core. In various embodiments, the insertions can include insertion of G or GS between any residues in A924-A926.

Some engineered soluble S immunogen polypeptides are derived from a MERS-CoV virus. Some of these polypeptides contain a modified S1/S2 cleavage site. As exemplification, the wildtype soluble S sequence to be used for engineering the MERS-CoV immunogen polypeptides of the invention is shown in SEQ ID NO:2 or N-terminal leader truncated soluble S sequence (SEQ ID NO:11). In other embodiments, the wildtype S sequence to be used can be a variant of SEQ ID NO:2 or 11, e.g., a substantially identical or conservatively modified variant thereof. Using amino acid numbering based on UniProt ID R9UQ53 or GenBank accession number JX869059.2 as reference, the modified sequence can contain a R748A/R751G double mutation, which leads to inactivation of the S1/S2 cleavage site. In addition to inactivation of the cleavage site, the soluble MERS-CoV immunogen polypeptides can additionally a double mutation in the HR1 region that remove strain in the turn region by preventing the formation of a straight helix during fusion. In various embodiments, this double mutation can be V1060G/L1061G, V1060P/L1061P, V1060G/L1061P or V1060P/L1061G.

Additional or alternative to the above-noted mutations that stabilize prefusion S structure, some MERS-CoV immunogen polypeptides of the invention can contain a deletion of a substantial portion of or the entire HR2 domain. Using the exemplified soluble MERS-CoV S sequence SEQ ID NO:2 to illustrate, this deletion can encompass amino acid residues 1229-1291 (SEQ ID NO:13). In various other embodiments, the deletion can be a truncation of the first 35, 40, 45, 50, 55, 60 or more C-terminal residues of SEQ ID NO:2. In some other embodiments, the soluble S sequence can have the N-terminal leader sequence truncated.

In some MERS-CoV immunogen polypeptides of the invention, additional mutations of the wildtype soluble S sequence can be introduced to destabilize the postfusion S structure. In some embodiments, one or more proline and/or glycine substitution can be engineered in the region of HR1 that interacts with HR2 to form the fusion core. These mutations function to disrupt the six-helix-bundle fusion core. In various embodiments, the mutations can include T1013P, T1014P, T1015P, T1013G, T1014G and T1015G. In some embodiments, one or more extra amino acid residues can be inserted into the region of HR1 that interacts with HR2 to form the fusion core. Similarly, these insertions also function to disrupt helical pattern of the fusion core. In various embodiments, the insertions can include insertion of G or GS between any residues in T1013-T1015.

In addition to the various substitutions and deletions noted above, the engineered coronavirus soluble S immunogen polypeptides of the invention can further contain a trimerization motif at the C-terminus. Suitable trimerization motifs for the invention include, e.g., T4 fibritin foldon (PDB ID: 4NCV) and viral capsid protein SHP (PDB: 1TD0). T4 fibritin (foldon) is well known in the art, and constitutes the C-terminal 30 amino acid residues of the trimeric protein fibritin from bacteriophage T4, and functions in promoting folding and trimerization of fibritin. See, e.g., Papanikolopoulou et al., J. Biol. Chem. 279: 8991-8998, 2004; and Guthe et al., J. Mol. Biol. 337: 905-915, 2004. Similarly, the SHP protein and its used as a functional trimerization motis are also well known in the art. See, e.g., Dreier et al., Proc Natl Acad Sci USA 110: E869-E877, 2013; and Hanzelmann et al., Structure 24: 140-147, 2016. The specific foldon and SHP sequences exemplified herein are GYIPEAPRDGQAYVRKDGEWVLLSTFL (foldon; SEQ ID NO:26), and EVRIFAGNDPAHTATGSSGISSPT-PALTPLMLDEATGKLVVWDGQKAGSAVGIL VLPLE-GTETALTYYKSGTFATEAIHWPESVDEHKKANAF-AGSALSHAA (1TD0; SEQ ID NO:27). In some embodiments, the trimerization motif is linked to the redesigned soluble S immunogen polypeptide via a short GS linker. The inclusion of the linker is intended to stabilize the formed trimer molecule. In various embodiments, the linker can contain 1-6 tandem repeats of GS. In some embodiments, an His6-tag can be added to the C-terminus of the trimerization motif to facilitate protein purification, e.g., by using a Nickel column.

In addition to S2GΔHR2 described above, other exemplary engineered SARS-CoV-2 spike proteins of the invention are shown in SEQ ID NOs:33-37. SEQ ID NO:33 is the sequence of S2GΔHR2 minus its N-terminal leader. Fusions of this sequence to trimerization motif foldon (SEQ ID NO:26) and 1TD0 (SEQ ID NO:27) are shown in SEQ ID NOs:35 and 36, respectively. In each of these two fusion sequences, a restriction site AS is introduced at the C-terminus of the engineered spike protein, which is then connected to the N-terminus of the trimerization motif via a $G_4S$ linker. SEQ ID NO:34 is a variant of SEQ ID NO:33 containing a HR1 swap. Specifically, the HR1 region L922-5943 is replaced by the equivalent region from SARS-CoV-1 spike protein. As exemplified herein, fusions containing this HR1 swapped SARS-CoV-2 spike protein to a trimerization motif (e.g., 1TD0) also displayed satisfactory immunogenic properties only when the HR2 stalk was removed. One such fusion is shown in SEQ ID NO:37. Any of these exemplified sequences, substantially identical sequences or conservatively modified variants thereof can be used in the invention for developing SARS-CoV-2 vaccines, e.g., nanoparticle scaffolded vaccines.

Sequence of engineered SARS-CoV-2 spike: S2GΔHR2 (minus N-terminal leader) (SEQ ID NO:33):

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTP
INLVRDLPQGFSALEPLVDLPIGINITRFQTLLALHRSYLTPGDSSSGW
TAGAAAYYVGYLQPRTFLLKYNENGTITDAVDCALDPLSETKCTLKSFT
VEKGIYQTSNFRVQPTESIVRFPNITNLCPFGEVFNATRFASVYAWNRK
RISNCVADYSVLYNSASFSTFKCYGVSPTKLNDLCFTNVYADSFVIRGD
EVRQIAPGQTGKIADYNYKLPDDFTGCVIAWNSNNLDSKVGGNYNYLYR
LFRKSNLKPFERDISTEIYQAGSTPCNGVEGFNCYFPLQSYGFQPTNGV
GYQPYRVVVLSFELLHAPATVCGPKKSTNLVKNKCVNFNFNGLTGTGVL
TESNKKFLPFQQFGRDIADTTDAVRDPQTLEILDITPCSFGGVSVITPG
TNTSNQVAVLYQDVNCTEVPVAIHADQLTPTWRVYSTGSNVFQTRAGCL
IGAEHVNNSYECDIPIGAGICASYQTQTNSPGSAGSVASQSIIAYTMSL
GAENSVAYSNNSIAIPTNFTISVTTEILPVSMTKTSVDCTMYICGDSTE
CSNLLLQYGSFCTQLNRALTGIAVEQDKNTQEVFAQVKQIYKTPPIKDF
GGFNFSQILPDPSKPSKRSFIEDLLFNKVTLADAGFIKQYGDCLGDIAA
RDLICAQKFNGLTVLPPLLTDEMIAQYTSALLAGTITSGWTFGAGAALQ
IPFAMQMAYRFNGIGVTQNVLYENQKLIANQFNSAIGKIQDSLSSTASA
LGKLQDVVNQNAQALNTLVKQLSSNFGAISSVLNDILSRLDGGEAEVQI
DRLITGRLQSLQTYVTQQLIRAAEIRASANLAATKMSECVLGQSKRVDF
CGKGYHLMSFPQSAPHGVVFLHVTYVPAQEKNFTTAPAICHDGKAHFPR
EGVFVSNGTHWFVTQRNFYEPQIITTDNTFVSGNCDVVIGIVNNTVYDP
LQPELDSFK

Sequence of S2GΔHR2-foldon fusion (SEQ ID NO:35). In the sequence, the introduced restriction site AS is italicized and underlined, the G$_4$S linker is italicized, and the foldon sequence is underlined.

QCVNLTTRTQLPPAYTNSFTRGVYYPDKVFRSSVLHSTQDLFLPFFSNV
TWFHAIHVSGTNGTKRFDNPVLPFNDGVYFASTEKSNIIRGWIFGTTLD
SKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTP
INLVRDLPQGFSALEPLVDLPIGINITRFQTLLALHRSYLTPGDSSSGW
TAGAAAYYVGYLQPRTFLLKYNENGTITDAVDCALDPLSETKCTLKSFT
VEKGIYQTSNFRVQPTESIVRFPNITNLCPFGEVFNATRFASVYAWNRK
RISNCVADYSVLYNSASFSTFKCYGVSPTKLNDLCFTNVYADSFVIRGD
EVRQIAPGQTGKIADYNYKLPDDFTGCVIAWNSNNLDSKVGGNYNYLYR
LFRKSNLKPFERDISTEIYQAGSTPCNGVEGFNCYFPLQSYGFQPTNGV
GYQPYRVVVLSFELLHAPATVCGPKKSTNLVKNKCVNFNFNGLTGTGVL
TESNKKFLPFQQFGRDIADTTDAVRDPQTLEILDITPCSFGGVSVITPG
TNTSNQVAVLYQDVNCTEVPVAIHADQLTPTWRVYSTGSNVFQTRAGCL
IGAEHVNNSYECDIPIGAGICASYQTQTNSPGSAGSVASQSIIAYTMSL
GAENSVAYSNNSIAIPTNFTISVTTEILPVSMTKTSVDCTMYICGDSTE
CSNLLLQYGSFCTQLNRALTGIAVEQDKNTQEVFAQVKQIYKTPPIKDF
GGFNFSQILPDPSKPSKRSFIEDLLFNKVTLADAGFIKQYGDCLGDIAA
RDLICAQKFNGLTVLPPLLTDEMIAQYTSALLAGTITSGWTFGAGAALQ
IPFAMQMAYRFNGIGVTQNVLYENQKLIANQFNSAIGKIQDSLSSTASA
LGKLQDVVNQNAQALNTLVKQLSSNFGAISSVLNDILSRLDGGEAEVQI
DRLITGRLQSLQTYVTQQLIRAAEIRASANLAATKMSECVLGQSKRVDF
CGKGYHLMSFPQSAPHGVVFLHVTYVPAQEKNFTTAPAICHDGKAHFPR
EGVFVSNGTHWFVTQRNFYEPQIITTDNTFVSGNCDVVIGIVNNTVYDP
LQPELDSFK*ASGGGGS*<u>GYIPEAPRDGQAYVRKDGEWVLLSTFL</u>

Sequence of S2GΔHR2-1TD0 fusion (SEQ ID NO:36). In the sequence, the introduced restriction site AS is italicized and underlined, the G$_4$S linker is italicized, and the 1TD0 sequence is underlined.

QCVNLTTRTQLPPAYTNSFTRGVYYPDKVFRSSVLHSTQDLFLPFFSNV
TWFHAIHVSGTNGTKRFDNPVLPFNDGVYFASTEKSNIIRGWIFGTTLD
SKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTP
INLVRDLPQGFSALEPLVDLPIGINITRFQTLLALHRSYLTPGDSSSGW
TAGAAAYYVGYLQPRTFLLKYNENGTITDAVDCALDPLSETKCTLKSFT
VEKGIYQTSNFRVQPTESIVRFPNITNLCPFGEVFNATRFASVYAWNRK
RISNCVADYSVLYNSASFSTFKCYGVSPTKLNDLCFTNVYADSFVIRGD
EVRQIAPGQTGKIADYNYKLPDDFTGCVIAWNSNNLDSKVGGNYNYLYR
LFRKSNLKPFERDISTEIYQAGSTPCNGVEGFNCYFPLQSYGFQPTNGV
GYQPYRVVVLSFELLHAPATVCGPKKSTNLVKNKCVNFNFNGLTGTGVL
TESNKKFLPFQQFGRDIADTTDAVRDPQTLEILDITPCSFGGVSVITPG
TNTSNQVAVLYQDVNCTEVPVAIHADQLTPTWRVYSTGSNVFQTRAGCL
IGAEHVNNSYECDIPIGAGICASYQTQTNSPGSAGSVASQSIIAYTMSL
GAENSVAYSNNSIAIPTNFTISVTTEILPVSMTKTSVDCTMYICGDSTE
CSNLLLQYGSFCTQLNRALTGIAVEQDKNTQEVFAQVKQIYKTPPIKDF
GGFNFSQILPDPSKPSKRSFIEDLLFNKVTLADAGFIKQYGDCLGDIAA
RDLICAQKFNGLTVLPPLLTDEMIAQYTSALLAGTITSGWTFGAGAALQ
IPFAMQMAYRFNGIGVTQNVLYENQKLIANQFNSAIGKIQDSLSSTASA
LGKLQDVVNQNAQALNTLVKQLSSNFGAISSVLNDILSRLDGGEAEVQI
DRLITGRLQSLQTYVTQQLIRAAEIRASANLAATKMSECVLGQSKRVDF
CGKGYHLMSFPQSAPHGVVFLHVTYVPAQEKNFTTAPAICHDGKAHFPR
EGVFVSNGTHWFVTQRNFYEPQIITTDNTFVSGNCDVVIGIVNNTVYDP
LQPELDSFK*ASGGGGS*<u>EVRIFAGNDPAHTATGSSGISSPTPALTPMLD
EATGKLVVWDGQKAGSAVGILVLPLEGTETALTYYKSGTFATEAIHWPE
SVDEHKKANAFAGSALSHAA</u>

Sequence of HR1 swapped S2GΔHR2 (SEQ ID NO:34): substituting HR1 region from SARs-CoV-1 is underlined.

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTP

INLVRDLPQGFSALEPLVDLPIGINITRFQTLLALHRSYLTPGDSSSGW

TAGAAAYYVGYLQPRTFLLKYNENGTITDAVDCALDPLSETKCTLKSFT

VEKGIYQTSNFRVQPTESIVRFPNITNLCPFGEVFNATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGV

GYQPYRVVVLSFELLHAPATVCGPKKSTNLVKNKCVNFNFNGLTGTGVL

TESNKKFLPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPGSAGSVASQSIIAYTMSL

GAENSVAYSNNSIAIPTNFTISVTTEILPVSMTKTSVDCTMYICGDSTE

CSNLLLQYGSFCTQLNRALTGIAVEQDKNTQEVFAQVKQIYKTPPIKDF

GGFNFSQILPDPSKPSKRSFIEDLLFNKVTLADAGFIKQYGDCLGDIAA

RDLICAQKFNGLTVLPPLLTDEMIAQYTSALLAGTITSGWTFGAGAALQ

IPPFAMQMAYRFNGIGVTQNVLYENQK<u>QIANQFNKAISQIQESLTTTSTA</u>

<u>LGKLQDVVNQNAQALNTLVKQLSSNFGAISSVLNDILSRLDGGEAEVQI</u>

<u>DRLITGRLQSLQTYVTQQLIRAAEIRASANLAATKMSECVLGQSKRVDF</u>

<u>CGKGYHLMSFPQSAPHGVVFLHVTYVPAQEKNFTTAPAICHDGKAHFPR</u>

<u>EGVFVSNGTHWFVTQRNFYEPQIITTDNTFVSGNCDVVIGIVNNTVYDP</u>

<u>LQPELDSFK</u>

Sequence of fusion of HR1 swapped S2GΔHR2 to 1TD0 (SEQ ID NO:37). In the sequence, the introduced restriction site AS is italicized and underlined, the G₄S linker is italicized, and the 1TD0 sequence is underlined.

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTP

INLVRDLPQGFSALEPLVDLPIGINITRFQTLLALHRSYLTPGDSSSGW

TAGAAAYYVGYLQPRTFLLKYNENGTITDAVDCALDPLSETKCTLKSFT

VEKGIYQTSNFRVQPTESIVRFPNITNLCPFGEVFNATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGV

GYQPYRVVVLSFELLHAPATVCGPKKSTNLVKNKCVNFNFNGLTGTGVL

TESNKKFLPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPGSAGSVASQSIIAYTMSL

GAENSVAYSNNSIAIPTNFTISVTTEILPVSMTKTSVDCTMYICGDSTE

CSNLLLQYGSFCTQLNRALTGIAVEQDKNTQEVFAQVKQIYKTPPIKDF

GGFNFSQILPDPSKPSKRSFIEDLLFNKVTLADAGFIKQYGDCLGDIAA

RDLICAQKFNGLTVLPPLLTDEMIAQYTSALLAGTITSGWTFGAGAALQ

IPPFAMQMAYRFNGIGVTQNVLYENQKQIANQFNKAISQIQESLTTTSTA

LGKLQDVVNQNAQALNTLVKQLSSNFGAISSVLNDILSRLDGGEAEVQI

DRLITGRLQSLQTYVTQQLIRAAEIRASANLAATKMSECVLGQSKRVDF

CGKGYHLMSFPQSAPHGVVFLHVTYVPAQEKNFTTAPAICHDGKAHFPR

EGVFVSNGTHWFVTQRNFYEPQIITTDNTFVSGNCDVVIGIVNNTVYDP

LQPELDSFKA*SGGGGS*<u>EVRIFAGNDPAHTATGSSGISSPTPALTPMLD</u>

<u>EATGKLVVWDGQKAGSAVGILVLPLEGTETALTYYKSGTFATEAIHWPE</u>

<u>SVDEHKKANAFAGSALSHAA</u>

IV. Nanoparticle Displayed Coronavirus Vaccine Compositions

The invention provides vaccine compositions that contain a heterologous scaffold that display at least one immunogen polypeptide or trimer protein derived from coronavirus S proteins. In some embodiments, the employed coronavirus S immunogen is a stabilized soluble S polypeptide containing various stabilizing mutations described above. In some other embodiments, the employed coronavirus immunogen contains or is derived from the RBD domain of coronavirus S proteins. In the latter embodiments, a SpyTag/SpyCatcher ligation system is used. As detailed in the Examples herein, the RBD sequence can be fused to a SpyTag motif, and the nanoparticle subunit sequence can be fused to a SpyCatcher motif. Alternatively, the RBD sequence can be fused to a SpyCatcher motif, and the nanoparticle subunit sequence can be fused to a SpyTag motif. In exemplified embodiments, the employed RBD sequence can contain the sequence shown in any one of SEQ ID NOs:4-6, or a substantially identical or conservatively modified variant there. Upon introducing the two constructs expressing the SpyTag fusion and the SpyCatcher fusion into host or producer cells, nanoparticle vaccines displaying an array of RBD proteins on the surface will be generated as a result of SpyTag/SpyCatcher mediated ligation of RBD proteins to the self-assembled nanoparticles.

Any heterologous scaffold can be used to present the immunogen protein or polypeptide in the construction of the vaccines of the invention. This includes a virus-like particle (VLP) such as bacteriophage Q$_\beta$ VLP and nanoparticles. Various nanoparticle platforms can be employed in generating the vaccine compositions of the invention. In general, the nanoparticles employed in the invention need to be formed by multiple copies of a single subunit. The nanoparticles are typically ball-like shaped, and/or have rotational symmetry (e.g., with 3-fold and 5-fold axis), e.g., with an icosahedral structure exemplified herein. Additionally or alternatively, the amino-terminus of the particle subunit has to be exposed and in close proximity to the 3-fold axis, and the spacing of three amino-termini has to closely match the spacing of the carboxyol-termini of the displayed trimeric stabilized soluble S protein.

In various embodiments, the employed self-assembling nanoparticles have a diameter of about 25 nm or less (usually assembled from 12, 24, or 60 subunits) and 3-fold axes on the particle surface. Such nanoparticles provide suitable particle platforms to produce multivalent vaccines. In some preferred embodiments, the coronavirus immunogen protein or polypeptide can be presented on self-assembling nanoparticles such as self-assembling nanoparticles derived from ferritin (FR) or E2p as exemplified herein. Other examples of nanoparticles suitable for the invention include nanoparticles derived from I3-01. Well known and routinely used in the art, ferritin is a globular protein found in all animals, bacteria, and plants. As is well known in the art, it acts primarily to control the rate and location of polynuclear Fe(III)$_2$O$_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. E2p is a redesigned variant of dihydrolipoyl acyltransferase from *Bacillus stearothermophilus* that has been shown to self-assemble into thermostable 60-meric nanoparticle. See, e.g., He et al., Nat. Commun. 7:12041, 2016. Similarly, I3-01 is an engineered protein that can self-assemble into hyperstable nanoparticles. See, e.g., Hsia et al., Nature 535, 136-139, 2016. Sequences of the subunits of these proteins are known in the art. See, e.g., WO2017/192434. More detailed information on the structural and functional properties of the various nanoparticle scaffolds, as well as their use in presenting trimeric protein immunogens, is provided in the art. See, e.g., WO2017/192434, WO2019/089817 and WO2019/241483. In various embodiments, the coronavirus vaccine compositions of the invention can employ any of these known nanoparticles, as well as their conservatively modified variants or variants with substantially identical (e.g., at least 90%, 95% or 99% identical) sequences.

In addition to the nanoparticle sequences noted above, many other nanoparticles or VLPs known in the art may also be used in the practice of the invention. These include, e.g., *Aquifex aeolicus* lumazine synthase, *Thermotoga maritima* encapsulin, *Myxococcus xanthus* encapsulin, bacteriophage Qbeta virus particle, Flock House Virus (FHV) particle, ORSAY virus particle, and infectious bursal disease virus (IBDV) particle.

In some exemplary embodiments, the nanoparticle vaccines of the invention contain a nanoparticle subunit sequence as shown in SEQ ID NO:23 (I3-01v9), SEQ ID NO:24 (E2p), or SEQ ID NO:25 (ferritin), a conservatively modified variant or a substantially identical sequence thereof. Typically, C-terminus of the engineered coronavirus immunogen polypeptide is fused to the N-terminus of subunit of the self-assembling nanoparticle (NP). In some embodiments, C-terminus of the engineered coronavirus polypeptide is fused to the nanoparticle subunit sequence of the self-assembling nanoparticle via a GS linker sequence, e.g., G$_4$S (GGGGS, SEQ ID NO:21) or (G$_4$S)$_2$ (GGGGSGGGGS; SEQ ID NO:22).

I3-01v9 subunit sequence (SEQ ID NO:23)

MKMEELFKKHKIVAVLRANSVEEAKMKALAVFVGGVHLIEITFTVP

DADTVIKELSFLKELGAIIGAGTVTSVEQCRKAVESGAEFIVSPHL

DEEISQFCKEKGVFYMPGVMTPTELVKAMKLGHTILKLFPGEVVGP

QFVKAMKGPFPNVKFVPTGGVNLDNVCEWFKAGVLAVGVGSALVKG

TIAEVAAKAAAFVEKIRGCTE

E2p subunit sequence (SEQ ID NO:24)

AAAKPATTEGEFPETREKMSGIRRAIAKAMVHSKHTAPHVTLMDEA

DVTKLVAHRKKFKAIAAEKGIKLTFLPYVVKALVSALREYPVLNTA

IDDETEEIIQKHYYNIGIAADTDRGLLVPVIKHADRKPIFALAQEI

NELAEKARDGKLTPGEMKGASCTITNIGSAGGQWFTPVINHPEVAI

LGIGRIAEKPIVRDGEIVAAPMLALSLSFDHRMIDGATAQKALNHI

KRLLSDPELLLM

Ferritin sequence (SEQ ID NO:25)

DIIKLLNEQVNKEMNSSNLYMSMSSWCYTHSLDGAGLFLFDHAAEEYEH

AKKLIIFLNENNVPVQLTSISAPEHKFEGLTQIFQKAYEHEQHISESIN

NIVDHAIKSKDHATFNFLQWYVAEQHEEEVLFKDILDKIELIGNENHGL

YLADQYVKGIAKSRK

Other than the displayed soluble S immunogen, the nanoparticle vaccine compositions of the invention can include additional motifs for better biological or pharmaceutical properties. These additional structural components can function to facilitate the immunogen display on the surface of the nanoparticles, to enhance the stability of the displayed immunogens, and/or to improve yield and purity of the self-assembled protein vaccines. In these embodiments, one or more linkers (linker sequences, motifs or moieties) can be used to connect the various structural components in the constructs.

In some embodiments, the nanoparticle vaccines of the invention can contain the coding sequence of a protein domain that serves to stabilize the immunogen polypeptide, such as the trimerization motif of T4 fibritin ("foldon") as noted above, or to elevate the immunogen polypeptide from the nanoparticle surface, such as a three-helix bundle ("neck domain"), or to facilitate immunoaffinity purification, such as a protein domain with known binding antibodies. These sequences can be added between the immunogen polypeptide sequence and the nanoparticle subunit sequence.

In some of these embodiments, a trimerization motif such as foldon and viral capsid protein SHP (PDB: 1TD0) can be added to the C-terminus of the stabilized soluble S protein as exemplified herein. As described above, the trimerization motif can be inserted with a short GS linker to further stabilize the trimer and also to increase the trimer ratio within the total protein yield. In some embodiments, the coding sequence of a polypeptide fragment or motif that serves as an active site for chemical conjugation can be inserted into the construct at an appropriate position. In some embodiments, additional structural components such as a CD4$^+$ T-helper epitope or a CD8$^+$ T-cell epitope can also be inserted into the nanoparticle construct at an appropriate position. These include, e.g., the PADRE T-helper epitope (AKFVAAWTLKAAA; SEQ ID NO:30) as exemplified herein. In some exemplary embodiments, the T-helper epitope can be inserted to the C-terminus of a locking domain, which is in turn fused to the C-terminus of the NP subunit sequence described below.

In some embodiments, the nanoparticle vaccines of the invention can contain a locking domain that stabilizes the nanoparticle. The locking domain coding sequence can be fused directly or indirectly to the C-terminus of the nanoparticle subunit coding sequence. The locking domain stabilizes the nanoparticles from the inside so that the nanoparticles presenting the coronavirus immunogen polypeptide can remain intact during manufacture, vaccine formulation, and immunization. The nanoparticle vaccine immunogens thus constructed have significantly enhanced stability. In general, the locking domain suitable for the invention is a protein subunit that can naturally form a dimer with another protein subunit in solution through non-covalent interactions at the interface. In some preferred embodiments, the two protein subunits can be identical in sequence and form a homodimer. In some other embodiments, the two protein subunits can be different proteins, or two different domains of a single protein derived through engineering, that can form a heterodimer in solution through non-covalent interactions at the interface. Typically, the locking domain is covalently fused to the nanoparticle subunit to which the immunogen polypeptide is linked. Examples of specific locking domains and guidance on the use of a locking domain in the construction of nanoparticle displayed trimeric immunogens can be found in the art, e.g., WO2019/241483. In some exemplary embodiments, the employed LD contains the sequence shown in SEQ ID NO:28 (LD4) or 29 (LD7), a conservatively modified variant or a substantially identical sequence thereof.

Locking domain LD4 (SEQ ID NO:28):

FSEEQKKALDLAFYFDRRLTPEWRRYLSQRLGLNEEQIERWFRRKEQQI

GWSHPQFEK

Locking domain LD7 (SEQ ID NO:29):

SPAVDIGDRLDELEKALEALSAEDGHDDVGQRLESLLRRWNSRRAD

Nanoparticles displaying any of the stabilized coronavirus soluble S protein immunogens described herein (e.g., stabilized SARS-CoV-2 soluble S trimer immunogens) can be constructed by fusing the immunogen polypeptide or subunit of multimeric immunogen protein (e.g., a trimer immunogen) to the subunit of the nanoparticle (e.g., E2p or I3-01 subunit), as well as the other optional or alternative components described herein (e.g., a locking domain or a trimerization motif). To construct the nanoparticle displayed fusion vaccine immunogens of the invention, one or more linker motifs or moieties may be employed to facilitate connection and maintain structural integrity of the different components. Typically, the linker motifs contain short peptide sequences, e.g., GS-rich peptides. In various embodiments, the linkers or linker motifs can be any flexible peptides that connect two protein domains or motifs without interfering with their functions. For example, the employed linker can be a 5-aa $G_4S$ linker (SEQ ID NO:21) or a 10-aa $(G_4S)_2$ linker (SEQ ID NO:22) as exemplified herein to connect (1) a spike protein and a nanoparticle scaffold sequence, (2) a spike protein and a trimerization motif, and/or (3) a nanoparticle scaffold sequence and a locking domain sequence. In some embodiments, a dipeptide GS linker can be used to connect a locking domain to a T epitope as exemplified herein. Detailed procedures for recombinant production of the vaccine compositions of the invention can be based on the protocols described herein and/or other methods that have been described in the art, e.g., He et al., Nat. Comm. 7, 12041, 2016; Kong et al., Nat. Comm. 7, 12040, 2016; He et al., Sci Adv. 4(11):eaau6769, 2018; He et al., bioRxiv, 2020.2008.2022.262634, 2020; WO2017/192434; WO2019/089817 and WO2019/241483.

Sequences of several specific nanoparticle displayed SARS-CoV-2 spike proteins of the invention are exemplified in SEQ ID NOs:38-40. SEQ ID NO:38 is the fusion sequence containing the leader-less S2GΔHR2 (SEQ ID NO:33) that is connected to nanoparticle sequence I3-01v9 (SEQ ID NO:23) via a $(G_4S)_2$ linker. This nanoparticle displayed spike further contains at its C-terminus the locking domain LD7 (SEQ ID NO:29) and the PADRE T-epitope (SEQ ID NO:30). SEQ ID NO:39 is the fusion sequence containing the leader-less S2GΔHR2 (SEQ ID NO:33) that is connected to nanoparticle sequence E2p (SEQ ID NO:24) via a $G_4S$ linker. This nanoparticle displayed spike further contains at its C-terminus the locking domain LD4 (SEQ ID NO:28) and the PADRE T-epitope (SEQ ID NO:30). SEQ ID NO:40 is the fusion sequence containing the leader-less S2GΔHR2 (SEQ ID NO:33) that is connected to nanoparticle sequence ferritin (SEQ ID NO:25) via a $G_4S$ linker. In addition to these specifically exemplified fusion constructs, the invention also encompasses SARS-CoV-2 nanoparticle vaccines that contain a subunit sequence that is a substantially identical to or conservatively modified variant of any of these exemplified nanoparticle vaccine sequences.

Sequence of 3 exemplary SARS-CoV-2 nanoparticle vaccines are shown in SEQ ID NOs:38-40 below. In these sequences, GS linkers (1) between the spike protein and the nanoparticle subunit sequence, (2) between the nanoparticle subunit sequence and the locking domain and (3) between the locking domain and the T-epitope are bolded, the nanoparticle subunit sequence is underlined, introduced restriction site AS is italicized and underlined, the locking domain sequence is italicized, and the T-epitope sequence is underlined and bolded.

Sequence of S2GΔHR2-10GS-I3-01v9-LD7-PADRE (SEQ ID NO:38).

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTP

INLVRDLPQGFSALEPLVDLPIGINITRFQTLLALHRSYLTPGDSSSGW

TAGAAAYYVGYLQPRTFLLKYNENGTITDAVDCALDPLSETKCTLKSFT

VEKGIYQTSNFRVQPTESIVRFPNITNLCPFGEVFNATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGV

GYQPYRVVVLSFELLHAPATVCGPKKSTNLVKNKCVNFNFNGLTGTGVL

TESNKKFLPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPGSAGSVASQSHAYTMSLG

AENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFG

-continued
GFNFSQILPDPSKPSKRSFIEDLLFNKVTLADAGFIKQYGDCLGDIAAR

DLICAQKFNGLTVLPPLLTDEMIAQYTSALLAGTITSGWTFGAGAALQI

PFAMQMAYRFNGIGVTQNVLYENQKLIANQFNSAIGKIQDSLSSTASAL

GKLQDVVNQNAQALNTLVKQLSSNFGAISSVLNDILSRLDGGEAEVQID

RLITGRLQSLQTYVTQQLIRAAEIRASANLAATKMSECVLGQSKRVDFC

GKGYHLMSFPQSAPHGVVFLHVTYVPAQEKNFTTAPAICHDGKAHFPRE

GVFVSNGTHWFVTQRNFYEPQIITTDNTFVSGNCDVVIGIVNNTVYDPL

QPELDSFKASGGGGSGGGGSMKMEELFKKHKIVAVLRANSVEEAKMKAL

AVFVGGVHLIEITFTVPDADTVIKELSFLKELGAIIGAGTVTSVEQCRK

AVESGAEFIVSPHLDEEISQFCKEKGVFYMPGVMTPTELVKAMKLGHTI

LKLFPGEVVGPQFVKAMKGPFPNVKFVPTGGVNLDNVCEWFKAGVLAVG

VGSALVKGTIAEVAAKAAAFVEKIRGCTEGGGGS*SPAVDIGDRLDELEK*

*ALEALSAEDGHDDVGQRLESLLRRWNSRRAD*GSAKFVAAWTLKAAA

Sequence of nanoparticle vaccine S2GΔHR2-5GS-E2p-LD4-PADRE (SEQ ID NO:39):

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTP

INLVRDLPQGFSALEPLVDLPIGINITRFQTLLALHRSYLTPGDSSSGW

TAGAAAYYVGYLQPRTFLLKYNENGTITDAVDCALDPLSETKCTLKSFT

VEKGIYQTSNFRVQPTESIVRFPNITNLCPFGEVFNATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGV

GYQPYRVVVLSFELLHAPATVCGPKKSTNLVKNKCVNFNFNGLTGTVL

TESNKKFLPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPGSAGSVASQSHAYTMSLG

AENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFG

GFNFSQILPDPSKPSKRSFIEDLLFNKVTLADAGFIKQYGDCLGDIAAR

DLICAQKFNGLTVLPPLLTDEMIAQYTSALLAGTITSGWTFGAGAALQI

PFAMQMAYRFNGIGVTQNVLYENQKLIANQFNSAIGKIQDSLSSTASAL

GKLQDVVNQNAQALNTLVKQLSSNFGAISSVLNDILSRLDGGEAEVQID

RLITGRLQSLQTYVTQQLIRAAEIRASANLAATKMSECVLGQSKRVDFC

GKGYHLMSFPQSAPHGVVFLHVTYVPAQEKNFTTAPAICHDGKAHFPRE

GVFVSNGTHWFVTQRNFYEPQIITTDNTFVSGNCDVVIGIVNNTVYDPL

QPELDSFKASGGGGSAAAKPATTEGEFPETREKMSGIRRAIAKAMVHSK

HTAPHVTLMDEADVTKLVAHRKKFKAIAAEKGIKLTFLPYVVKALVSAL

-continued
REYPVLNTAIDDETEEIIQKHYYNIGIAADTDRGLLVPVIKHADRKPIF

ALAQEINELAEKARDGKLTPGEMKGASCTITNIGSAGGQWFTPVINHPE

VAILGIGRIAEKPIVRDGEIVAAPMLALSLSFDHRMIDGATAQKALNHI

KRLLSDPELLLMGGGGS*FSEEQKKALDLAFYFDRRLTPEWRRYLSQRLG*

*LNEEQIERWFRRKEQQIGWSHPQFEK*GSAKFVAAWTLKAAA

Sequence of nanoparticle vaccine S2GΔHR2-5GS-ferritin (SEQ ID NO:40):

QCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLD

SKTQSLLIVNNATNVVIKVCEFQFCNDPFLGVYYHKNNKSWMESEFRVY

SSANNCTFEYVSQPFLMDLEGKQGNFKNLREFVFKNIDGYFKIYSKHTP

INLVRDLPQGFSALEPLVDLPIGINITRFQTLLALHRSYLTPGDSSSGW

TAGAAAYYVGYLQPRTFLLKYNENGTITDAVDCALDPLSETKCTLKSFT

VEKGIYQTSNFRVQPTESIVRFPNITNLCPFGEVFNATRFASVYAWNRK

RISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGV

GYQPYRVVVLSFELLHAPATVCGPKKSTNLVKNKCVNFNFNGLTGTVL

TESNKKFLPFQQFGRDIADTTDAVRDPQTLEILDITPCSFGGVSVITPG

TNTSNQVAVLYQDVNCTEVPVAIHADQLTPTWRVYSTGSNVFQTRAGCL

IGAEHVNNSYECDIPIGAGICASYQTQTNSPGSAGSVASQSHAYTMSLG

AENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFG

GFNFSQILPDPSKPSKRSFIEDLLFNKVTLADAGFIKQYGDCLGDIAAR

DLICAQKFNGLTVLPPLLTDEMIAQYTSALLAGTITSGWTFGAGAALQI

PFAMQMAYRFNGIGVTQNVLYENQKLIANQFNSAIGKIQDSLSSTASAL

GKLQDVVNQNAQALNTLVKQLSSNFGAISSVLNDILSRLDGGEAEVQID

RLITGRLQSLQTYVTQQLIRAAEIRASANLAATKMSECVLGQSKRVDFC

GKGYHLMSFPQSAPHGVVFLHVTYVPAQEKNFTTAPAICHDGKAHFPRE

GVFVSNGTHWFVTQRNFYEPQIITTDNTFVSGNCDVVIGIVNNTVYDPL

QPELDSFKASGGGGSDIIKLLNEQVNKEMQSSNLYMSMSSWCYTHSLDG

AGLFLFDHAAEEYEHAKKLIIFLNENNVPVQLTSISAPEHKFEGLTQIF

QKAYEHEQHISESINNIVDHAIKSKDHATFNFLQWYVAEQHEEEVLFKD

ILDKIELIGNENHGLYLADQYVKGIAKSRKS

V. Polynucleotides and Expression Constructs

The stabilized coronavirus soluble S immunogen proteins and the related vaccine compositions of the invention are typically produced by first generating expression constructs (i.e., expression vectors) that contain operably linked coding sequences of the various structural components described herein. Accordingly, in some related aspects, the invention provides substantially purified polynucleotides (DNA or RNA) that encode the immunogens or nanoparticle displayed immunogens as described herein. Some polynucleotides of the invention encode one of the engineered spike immunogen polypeptides described herein, e.g., stabilized SARS-COV-2 soluble S immunogens shown in SEQ ID NOs:32-37. Some polynucleotides of the invention encode the subunit sequence of one of the nanoparticle scaffolded vaccines described herein, e.g., the fusion protein sequences shown in SEQ ID NOs:38-40. While the expressed spike immunogen polypeptides of the invention typically do not contain the N-terminal leader sequence, some of the polynucleotide sequences of the invention additionally encode the leader sequence of the native spike protein. Thus, for example, polynucleotides encoding engineered SARS-COV-2 spike immunogen polypeptides (e.g., SEQ ID NOs: 33-37) or the nanoparticle scaffolded polypeptide sequences (e.g., SEQ ID NO:38-40) can additionally encode the native leader sequence shown in SEQ ID NO:15, or a substantially identical or conservatively modified variant sequence.

Also provided in the invention are expression vectors that harbor such polynucleotides (e.g., CMV vectors exemplified herein) and host cells for producing the vaccine immunogens (e.g., HEK293F, ExpiCHO, and CHO-S cell lines exemplified herein). The fusion polypeptides encoded by the polynucleotides or expressed from the vectors are also included in the invention. As described herein, the nanoparticle subunit fused soluble S immunogen polypeptides will self-assemble into nanoparticle vaccines that display the immunogen polypeptides or proteins on its surface.

The polynucleotides and related vectors can be readily generated with standard molecular biology techniques or the protocols exemplified herein. For example, general protocols for cloning, transfecting, transient gene expression and obtaining stable transfected cell lines are described in the art, e.g., Sambrook et al., Molecular Cloning: A Laboratory Manual, Cold Spring Harbor Press, N.Y., ($3^{rd}$ ed., 2000); and Brent et al., Current Protocols in Molecular Biology, John Wiley & Sons, Inc. (ringbou ed., 2003). Introducing mutations to a polynucleotide sequence by PCR can be performed as described in, e.g., *PCR Technology: Principles and Applications for DNA Amplification*, H. A. Erlich (Ed.), Freeman Press, NY, NY, 1992; *PCR Protocols: A Guide to Methods and Applications*, Innis et al. (Ed.), Academic Press, San Diego, CA, 1990; Manila et al., Nucleic Acids Res. 19:967, 1991; and Eckert et al., PCR Methods and Applications 1:17, 1991.

The selection of a particular vector depends upon the intended use of the fusion polypeptides. For example, the selected vector must be capable of driving expression of the fusion polypeptide in the desired cell type, whether that cell type be prokaryotic or eukaryotic. Many vectors contain sequences allowing both prokaryotic vector replication and eukaryotic expression of operably linked gene sequences. Vectors useful for the invention may be autonomously replicating, that is, the vector exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Both viral-based and nonviral expression vectors can be used to produce the immunogens in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). Useful viral vectors include vectors based on lentiviruses or other retroviruses, adenoviruses, adenoassociated viruses, Cytomegalovirus, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Depending on the specific vector used for expressing the fusion polypeptide, various known cells or cell lines can be employed in the practice of the invention. The host cell can be any cell into which recombinant vectors carrying a fusion of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells or may be an established cell line. Thus, in addition to the cell lines exemplified herein (e.g., CHO cells), a number of other host cell lines capable well known in the art may also be used in the practice of the invention. These include, e.g., various Cos cell lines, HeLa cells, Sf9 cells, HEK293, AtT20, BV2, and N18 cells, myeloma cell lines, transformed B-cells and hybridomas.

The use of mammalian tissue cell culture to express polypeptides is discussed generally in, e.g., Winnacker, *From Genes to Clones*, VCH Publishers, N.Y., N.Y., 1987. The fusion polypeptide-expressing vectors may be introduced to the selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, Life Technologies, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre et al., Gene, 30: 147, 1984). Through appropriate selections, the

VI. Pharmaceutical Compositions and Therapeutic Applications

In another aspect, the invention provides pharmaceutical compositions and related therapeutic methods of using the redesigned coronavirus S immunogens and nanoparticle vaccine compositions as described herein. In various embodiments, the pharmaceutical compositions can contain the engineered viral spike proteins or RBD polypeptides, nanoparticle scaffolded viral spike immunogens, as well as polynucleotide sequences or vectors encoding the engineered viral spike immunogens or nanoparticle vaccines described herein. In some embodiments, the soluble S trimer immunogen for the different viruses (e.g., SARS-COV-2) can be used for preventing and treating the corresponding viral infections. In various other embodiments, the nanoparticle vaccines containing different viral or non-viral immunogens described herein can be employed to prevent or treat the corresponding diseases, e.g., infections caused by the various coronaviruses. Some embodiments of the invention relate to use of the SARS-COV-2 immunogens or vaccines for preventing or treating SARS-COV-2 infections in human subjects. Some embodiments of the invention relate to use of the SARS-CoV immunogens or vaccines for preventing or treating SARS-CoV infections. Some embodiments of the invention relate to use of the MERS-CoV immunogens or vaccines for preventing or treating MERS-CoV infections.

In the practice of the various therapeutic methods of the invention, the subjects in need of prevention or treatment of a disease or condition (e.g., SARS-COV-2 infection) is administered with the corresponding nanoparticle vaccine, the immunogen protein or polypeptide, or an encoding polynucleotide described herein. Typically, the nanoparticle vaccine, the immunogen protein or the encoding polynucleotide disclosed herein is included in a pharmaceutical composition. The pharmaceutical composition can be either a therapeutic formulation or a prophylactic formulation. Typically, the composition can additionally include one or more pharmaceutically acceptable vehicles and, optionally, other therapeutic ingredients (for example, antiviral drugs). Various pharmaceutically acceptable additives can also be used in the compositions.

Thus, some of the pharmaceutical compositions of the invention are vaccine compositions. For vaccine compositions, appropriate adjuvants can be additionally included. Examples of suitable adjuvants include, e.g., aluminum hydroxide, lecithin, Freund's adjuvant, MPL™ and IL-12. In some embodiments, the vaccine compositions or nanoparticle immunogens disclosed herein (e.g., SARS-COV-2 vaccine composition) can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art. See, e.g., Remington's Pharmaceutical Sciences, 19$^{th}$ Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728,721; and 4,675,189.

The pharmaceutical compositions of the invention can be readily employed in a variety of therapeutic or prophylactic applications, e.g., for treating SARS-COV-2 infection or eliciting an immune response to SARS-COV-2 in a subject. In various embodiments, the vaccine compositions can be used for treating or preventing infections caused by a pathogen from which the displayed immunogen polypeptide in the nanoparticle vaccine is derived. Thus, the vaccine compositions of the invention can be used in diverse clinical settings for treating or preventing infections caused by various viruses. As exemplification, a SARS-COV-2 nanoparticle vaccine composition can be administered to a subject to induce an immune response to SARS-COV-2, e.g., to induce production of broadly neutralizing antibodies to the virus. For subjects at risk of developing an SARS-COV-2 infection, a vaccine composition of the invention can be administered to provide prophylactic protection against viral infection. Therapeutic and prophylactic applications of vaccines derived from the other immunogens described herein can be similarly performed. Depending on the specific subject and conditions, pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes.

In general, the pharmaceutical composition is administered to a subject in need of such treatment for a time and under conditions sufficient to prevent, inhibit, and/or ameliorate a selected disease or condition or one or more symptom(s) thereof. In various embodiments, the therapeutic methods of the invention relate to methods of blocking the entry of a coronavirus (e.g., SARS-CoV, SARS-CoV-2, or MERS-CoV) into a host cell, e.g., a human host cell, methods of preventing the S protein of a coronavirus from binding the host receptor, and methods of treating acute respiratory distress that is often associated with coronavirus infections. In some embodiments, the therapeutic methods and compositions described herein can be employed in combination with other known therapeutic agents and/or modalities useful for treating or preventing coronavirus infections. The known therapeutic agents and/or modalities include, e.g., a nuclease analog or a protease inhibitor (e.g., remdesivir), monoclonal antibodies directed against one or more coronaviruses, an immunosuppressant or anti-inflammatory drug (e.g., sarilumab or tocilizumab), ACE inhibitors, vasodilators, or any combination thereof.

For therapeutic applications, the compositions should contain a therapeutically effective amount of the nanoparticle immunogen described herein. For prophylactic applications, the compositions should contain a prophylactically effective amount of the nanoparticle immunogen described herein. The appropriate amount of the immunogen can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an infection (e.g., SARS-COV-2 infection), for example because of exposure or the possibility of exposure to the virus (e.g., SARS-COV-2). Following administration of a therapeutically effective amount of the disclosed therapeutic compositions, the subject can be monitored for an infection (e.g., SARS-COV-2 infection), symptoms associated with an infection (e.g., SARS-COV-2 infection), or both.

For therapeutic applications, the immunogenic composition is provided at or after the onset of a symptom of disease or infection, for example after development of a symptom of infection (e.g., SARS-COV-2 infection), or after diagnosis of the infection. The immunogenic composition can thus be provided prior to the anticipated exposure to the virus so as to attenuate the anticipated severity, duration or extent of an infection and/or associated disease symptoms, after exposure or suspected exposure to the virus, or after the actual initiation of an infection. The pharmaceutical composition of the invention can be combined with other agents known in the art for treating or preventing infections by a relevant pathogen (e.g., SARS-COV-2 infection).

The nanoparticle vaccine compositions containing novel structural components as described in the invention (e.g., SARS-COV-2 vaccine) or pharmaceutical compositions of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1 S Antigen Stabilization, Production, and Purification

This Example describes redesigned stable and soluble coronavirus S trimers:

I. SARS-CoV

The sequence of SARS-CoV S protein was obtained from GenBank with the ID NP_828851. The numbering is based on the UniProt definition with UniPro ID P59594. The soluble S construct is defined as M1-Q1190. Q1190 is immediately upstream of the predicted transmembrane region that starts with the $^{1191}$YIK$^{1193}$ motif A truncated soluble S construct is defined as M1-K1131, which is devoid of HR2. The HR2 deletion will disrupt the HR1/HR2 fusion core and stabilize the prefusion S structure. The S construct can be further truncated at Y1120 with a 3-residue "GNS" motif (from MERS-CoV S) added to Y1120. This modification will increase protein yield significantly when displayed on nanoparticles.

Uncleaved, prefusion-optimized (UFO) S constructs can be obtained by (a) adding a R667G mutation and a K968P/V969P (or K968G/V969G) double mutation between the HR1 and the central helix (CH). While the R667G mutation aims to remove the S1/cleavage site, the K968P/V969P double mutation has been shown to stabilize the prefusion S structure. Instead of rigidifying the HR1-turn-CH, the K968G/V969G double mutation aims to remove any strain in the turn region and as a result to stabilize the prefusion S structure.

The UFO S constructs described above can be further stabilized by introducing a proline mutation (S924P, T925P, or A926P), a glycine mutation (S924G, T925G, or A926G), or their combinations to the HR1 region that interacts with HR2 to form a fusion core. These mutations function to disrupt the six-helix-bundle fusion core and destabilize the postfusion S. Other mutations such as inserting one or two residues (e.g. G or GS) in the region S924-A926 to disrupt the helical pattern can also destabilize the postfusion S and prevent conformational change.

Trimerization motifs such as T4 fibritin foldon (PDB ID: 4NCV) and viral capsid protein SHP (PDB: 1TD0) can be further added to the C-terminus of a redesigned S construct described above with a short GS linker in between to stabilize the trimer. In addition, an His6-tag can be added to the C-terminus of the trimerization motif to facilitate protein purification using a Nickel column.

The C-terminus of the redesigned SARS-CoV UFO S constructs can be fused to the N-terminus of a nanoparticle-forming subunit (ferritin 24-mer and two 60-mers, E2p and I3-01) so that the fusion construct, when expressed in appropriate cell lines, can self-assemble into nanoparticles with prefusion S trimers displayed on the nanoparticle surface.

SARS-CoV soluble S sequence (SEQ ID NO:1):

```
MFIFLLFLTLTSGSDLDRCTTFDDVQAPNYTQHTSSMRGVYYPDEIFRS
DTLYLTQDLFLPFYSNVTGFHTINHTFGNPVIPFKDGIYFAATEKSNVV
RGWVFGSTMNNKSQSVIIINNSTNVVIRACNFELCDNPFFAVSKPMGTQ
THTMIFDNAFNCTFEYISDAFSLDVSEKSGNFKHLREFVFKNKDGFLYV
YKGYQPIDVVRDLPSGFNTLKPIFKLPLGINITNFRAILTAFSPAQDIW
GTSAAAYFVGYLKPTTFMLKYDENGTITDAVDCSQNPLAELKCSVKSFE
IDKGIYQTSNFRVVPSGDVVRFPNITNLCPFGEVFNATKFPSVYAWERK
KISNCVADYSVLYNSTFFSTFKCYGVSATKLNDLCFSNVYADSFVVKGD
DVRQIAPGQTGVIADYNYKLPDDFMGCVLAWNTRNIDATSTGNYNYKYR
YLRHGKLRPFERDISNVPFSPDGKPCTPPALNCYWPLNDYGFYTTTGIG
YQPYRVVVLSFELLNAPATVCGPKLSTDLIKNQCVNFNFNGLTGTGVLT
PSSKRFQPFQQFGRDVSDFTDSVRDPKTSEILDISPCAFGGVSVITPGT
NASSEVAVLYQDVNCTDVSTAIHADQLTPAWRIYSTGNNVFQTQAGCLI
GAEHVDTSYECDIPIGAGICASYHTVSLLRSTSQKSIVAYTMSLGADSS
IAYSNNTIAIPTNFSISITTEVMPVSMAKTSVDCNMYICGDSTECANLL
LQYGSFCTQLNRALSGIAAEQDRNTREVFAQVKQMYKTPTLKYFGGFNF
SQILPDPLKPTKRSFIEDLLFNKVTLADAGFMKQYGECLGDINARDLIC
AQKFNGLTVLPPLLTDDMIAAYTAALVSGTATAGWTFGAGAALQIPFAM
QMAYRFNGIGVTQNVLYENQKQIANQFNKAISQIQESLTTTSTALGKLQ
DVVNQNAQALNTLVKQLSSNFGAISSVLNDILSRLDKVEAEVQIDRLIT
GRLQSLQTYVTQQLIRAAEIRASANLAATKMSECVLGQSKRVDFCGKGY
HLMSFPQAAPHGVVFLHVTYVPSQERNFTTAPAICHEGKAYFPREGVFV
FNGTSWFITQRNFFSPQIITTDNTFVSGNCDVVIGIINNTVYDPLQPEL
DSFKEELDKYFKNHTSPDVDLGDISGINASVVNIQKEIDRLNEVAKNLN
ESLIDLQELGKYEQ
```

SARS-CoV soluble S sequence minus N-terminal leader (SEQ ID NO:7): residues 14-1190 of SEQ ID NO:1.

Leader sequence (SEQ ID NO:8): MFIFLLFLTLTSG (residues 1-13 of SEQ ID NO:1).

HR2 sequence (SEQ ID NO:9): residues 1132-1190 of SEQ ID NO:1 EELDKYFKNHTSPDVDLGDISGI-NASVVNIQKEIDRLNEVAKNLNESLIDLQELG KYEQ Further truncated C-terminal sequence (SEQ ID NO:10): DPLQPELDSFK (residues 1121-1131 of SEQ ID NO:1).

II. MERS-CoV

The sequence of MERS-CoV S protein was obtained from GenBank with the ID JX869059.2. The amino acid numbering is based on the UniProt definition with UniPro ID R9UQ53.

The soluble S construct is defined as M1-Y1291. Y1291 is immediately upstream of the predicted transmembrane region that starts with the $^{1292}$YNK$^{1294}$ motif. A truncated soluble S construct is defined as M1-S1226, which is devoid of HR2. The HR2 deletion will disrupt the HR1/HR2 fusion core and stabilize the prefusion S structure.

Uncleaved, prefusion-optimized (UFO) S constructs can be obtained by adding a R748A/R751G double mutation and a V1060P/L1061P (or V1060G/L1061G) double mutation. While the R748A/R751G double mutation aims to remove the S1/S2 cleavage site, the V1060P/L1061P double mutation has been shown to stabilize the prefusion S structure. Instead of rigidifying the HR1-turn-CH, the V1060G/L1061G double mutation aims to remove any strain in the turn region and as a result to stabilize the prefusion S structure.

The UFO S constructs can be further stabilized by introducing a proline mutation (T1013P, T1014P, or T1015P), a glycine mutation (T1013G, T1014G, or T1015G), or their combinations to the HR1 region that interacts with HR2 to form a fusion core. These mutations will disrupt the six-helix-bundle fusion core and destabilize the postfusion S. Other mutations such as inserting one or two residues (e.g. G or GS) in the region T1013-T1015 to disrupt the helical pattern will also destabilize the postfusion S and prevent conformational change.

Trimerization motifs such as T4 fibritin foldon (PDB ID: 4NCV) and viral capsid protein SHP (PDB: 1TD0) can be added to the C-terminus of the redesigned UFO S constructs described above with a short GS linker in between to stabilize the trimer. An His6-tag can be added to the C-terminus of the trimerization motif to facilitate protein purification by a Nickel column.

The C-terminus of the redesigned MERS-CoV UFO S constructs can be fused to the N-terminus of a nanoparticle-forming subunit so that the fusion construct, when expressed in appropriate cell lines, can self-assemble into nanoparticles with prefusion S trimers displayed on the nanoparticle surface.

MERS-CoV soluble S (SEQ ID NO:2):

MIHSVFLLMFLLTPTESYVDVGPDSVKSACIEVDIQQTFFDKTWPRPID

VSKADGITYPQGRTYSNITITYQGLFPYQGDHGDMYVYSAGHATGTTPQ

KLFVANYSQDVKQFANGFVVRIGAAANSTGTVIISPSTSATIRKIYPAF

MLGSSVGNFSDGKMGRFFNHTLVLLPDGCGTLLRAFYCILEPRSGNHCP

AGNSYTSFATYHTPATDCSDGNYNRNASLNSFKEYFNLRNCTFMYTYNI

TEDEILEWFGITQTAQGVHLFSSRYVDLYGGNMFQFATLPVYDTIKYYS

IIPHSIRSIQSDRKAWAAFYVYKLQPLTFLLDFSVDGYIRRAIDCGFND

LSQLHCSYESFDVESGVYSVSSFEAKPSGSVVEQAEGVECDFSPLLSGT

PPQVYNFKRLVFTNCNYNLTKLLSLFSVNDFTCSQISPAAIASNCYSSL

ILDYFSYPLSMKSDLSVSSAGPISQFNYKQSFSNPTCLILATVPHNLTT

ITKPLKYSYINKCSRLLSDDRTEVPQLVNANQYSPCVSIVPSTVWEDGD

YYRKQLSPLEGGGWLVASGSTVAMTEQLQMGFGITVQYGTDTNSVCPKL

EFANDTKIASQLGNCVEYSLYGVSGRGVFQNCTAVGVRQQRFVYDAYQN

LVGYYSDDGNYYCLRACVSVPVSVIYDKETKTHATLFGSVACEHISSTM

SQYSRSTRSMLKRRDSTYGPLQTPVGCVLGLVNSSLFVEDCKLPLGQSL

CALPDTPSTLTPRSVRSVPGEMRLASIAFNHPIQVDQLNSSYFKLSIPT

NFSFGVTQEYIQTTIQKVTVDCKQYVCNGFQKCEQLLREYGQFCSKINQ

ALHGANLRQDDSVRNLFASVKSSQSSPIIPGFGGDFNLTLLEPVSISTG

SRSARSAIEDLLFDKVTIADPGYMQGYDDCMQQGPASARDLICAQYVAG

YKVLPPLMDVNMEAAYTSSLLGSIAGVGWTAGLSSFAAIPFAQSIFYRL

NGVGITQQVLSENQKLIANKFNQALGAMQTGFTTTNEAFQKVQDAVNNN

AQALSKLASELSNTFGAISASIGDIIQRLDVLEQDAQIDRLINGRLTTL

NAFVAQQLVRSESAALSAQLAKDKVNECVKAQSKRSGFCGQGTHIVSFV

VNAPNGLYFMHVGYYPSNHIEVVSAYGLCDAANPTNCIAPVNGYFIKTN

NTRIVDEWSYTGSSFYAPEPITSLNTKYVAPQVTYQNISTNLPPPLLGN

STGIDFQDELDEFFKNVSTSIPNFGSLTQINTTLLDLTYEMLSLQQVVK

ALNESYIDLKELGNYTY

MERS-CoV soluble S sequence minus N-terminal leader (SEQ ID NO:11): residues 18-1291 of SEQ ID NO:2.

Leader sequence (SEQ ID NO:12): MIHSVFLL-MFLLTPTES (residues 1-17 of SEQ ID NO:2).

HR2 sequence (SEQ ID NO:13): residues 1227-1291 of SEQ ID NO:2 TGIDFQDELDEFFKNVST-SIPNFGSLTQINTTLLDLTYEMLSLQQVVKALNESYI DLKELGNYTY

III. SARS-CoV-2

The sequence of SARS-CoV-2 S protein was obtained from GenBank with the ID MN908947.3. The amino acid numbering is based on the cryo-EM model with PDB ID 6VSB.

The soluble S construct is defined as M1-Q1208. Q1208 is immediately upstream of the predicted transmembrane region that starts with the $^{1209}$YIK$^{1211}$ motif. A truncated soluble S construct is defined as M1-K1149, which is devoid of HR2. The HR2 deletion will disrupt the HR1/HR2 fusion core and stabilize the prefusion S structure. The S construct can be further truncated at Y1138 with a 3-residue "GNS" motif (from MERS-CoV S) added to Y1138. This modification will increase protein yield significantly when displayed on nanoparticles.

The uncleaved, prefusion-optimized (UFO) soluble S construct is defined as M1-Q1208 with the modified S1/S2 cleavage site $^{682}$GSAGSV$^{687}$ (SEQ ID NO:18) and a K986P/V987P (or K986G/V987G) double mutation. SARS-CoV-2 has a 4-aa insertion prior to the S1/S2 cleavage site, $^{681}$PRRA$^{684}$, which will enhance the cleavage efficiency.

The modification ⁶⁸²GSAGSV⁶⁸⁷ (SEQ ID NO:18) aims to remove the S1/S2 cleavage site, and the K986P/V987P double mutation has been shown to stabilize the prefusion S structure. Instead of rigidifying the HR1-turn-CH, the K986G/V987G double mutation aims to remove any strain in the turn region and as a result to stabilize the prefusion S structure.

The SARS-CoV-2 UFO S constructs in (b) can be further stabilized by introducing a proline mutation (A942P, S943P, and A944P), a glycine mutation (A942G, S943G, and A944G), or their combinations to the HR1 region that interacts with HR2 to form a fusion core. These mutations will disrupt the six-helix-bundle fusion core and destabilize the postfusion S. Other mutations such as inserting one or two residues (e.g. G or GS) in the region A942-A944 to disrupt the helical pattern will also destabilize the postfusion S and prevent conformational change.

Trimerization motifs such as T4 fibritin foldon (PDB ID: 4NCV) and viral capsid protein SHP (PDB: 1TD0) can be added to the C-terminus of a redesigned S construct in (b) and (c) with a short GS linker in between to stabilize the trimer. An His6-tag can be added to the C-terminus of the trimerization motif to facilitate protein purification by a Nickel column.

The C-terminus of the redesigned SARS-CoV-2 UFO S construct described above can be fused to the N-terminus of a nanoparticle-forming subunit so that the fusion construct, when expressed in appropriate cell lines, can self-assemble into nanoparticles with prefusion S trimers displayed on the nanoparticle surface.

SARS-CoV-2 soluble S (SEQ ID NO:3):

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRARS

VASQSHAYTMSLGAENSVAYSNNSIAIPTNFTISVTTEILPVSMTKTSV

DCTMYICGDSTECSNLLLQYGSFCTQLNRALTGIAVEQDKNTQEVFAQV

KQIYKTPPIKDFGGFNFSQILPDPSKPSKRSFIEDLLFNKVTLADAGFI

KQYGDCLGDIAARDLICAQKFNGLTVLPPLLTDEMIAQYTSALLAGTIT

SGWTFGAGAALQIPFAMQMAYRFNGIGVTQNVLYENQKLIANQFNSAIG

KIQDSLSSTASALGKLQDVVNQNAQALNTLVKQLSSNFGAISSVLNDIL

SRLDKVEAEVQIDRLITGRLQSLQTYVTQQLIRAAEIRASANLAATKMS

ECVLGQSKRVDFCGKGYHLMSFPQSAPHGVVFLHVTYVPAQEKNFTTAP

AICHDGKAHFPREGVFVSNGTHWFVTQRNFYEPQIITTDNTFVSGNCDV

VIGIVNNTVYDPLQPELDSFKEELDKYFKNHTSPDVDLGDISGINASVV

NIQKEIDRLNEVAKNLNESLIDLQELGKYEQ

SARS-CoV-2 soluble S sequence minus N-terminal leader (SEQ ID NO:14): residues 14-1208 of SEQ ID NO:3.

Leader sequence (SEQ ID NO:15): MFVFLVLLPLVSS (residues 1-13 of SEQ ID NO:3).

HR2 sequence (SEQ ID NO:9): residues 1150-1208 of SEQ ID NO:3 EELDKYFKNHTSPDVDLGDISGI-NASVVNIQKEIDRLNEVAKNLNESLIDLQELG KYEQ Further truncated C-terminal sequence (SEQ ID NO:10): DPLQPELDSFK (residues 1121-1131 of SEQ ID NO:3)

Example 2 Designed RBD Domains of Coronaviruses

I. SARS-CoV RBD Based Vaccines

The sequence of SARS-CoV S protein and amino acid numbering are noted above. The SARS-CoV RBD used in RBD-based vaccine design is defined as P317-D518 (see SEQ ID NO:4). Specifically, a trimerization motif, the viral capsid protein SHP (PDB: 1TD0), can be added to the C-terminus of SARS-CoV RBD with a short 5GS linker in between to stabilize RBD in a trimeric conformation. A His6-tag can be added to the C-terminus of the trimerization motif with a 1GS linker to facilitate purification.

SpyTag and SpyCatcher can be attached to SARS-CoV RBD and a nanoparticle subunit in different combinations to facilitate the multivalent display of RBD on nanoparticle. For example, if the C-terminus of RBD is fused to the N-terminus of SpyTag with a 5GS linker, the C-terminus of SpyCatcher can be fused to the N-terminus of a nanoparticle subunit with a 5GS linker to create a pair. SpyTag and SpyCatcher can be switched in these two constructs to create a different pair. SpyTag or SpyCatcher can also be fused to the N-terminus of RBD with a 5GS linker. When the two constructs are introduced into and expressed in the host cells, a recombinant vaccine protein will be formed through the binding between the SpyTag and SpyCatcher motifs.

SARS-CoV RBD (SEQ ID NO:4)

PNITNLCPFGEVFNATKFPSVYAWERKKISNCVADYSVLYNSTFFSTFK

CYGVSATKLNDLCFSNVYADSFVVKGDDVRQIAPGQTGVIADYNYKLPD

DFMGCVLAWNTRNIDATSTGNYNYKYRYLRHGKLRPFERDISNVPFSPD

GKPCTPPALNCYWPLNDYGFYTTTGIGYQPYRVVVLSFELLNAPATVCG

PKLSTD

SpyTag: VPTIVMVDAYKRYK (SEQ ID NO:16).
SpyCatcher: SEQ ID NO:17

AMVTTLSGLSGEQGPSGDMTTEEDSATHIKFSKRDEDGRELAGATMELR

DSSGKTISTWISDGHVKDFYLYPGKYTFVETAAPDGYEVATAITFTVNE

QGQVTVNGEATKGDAHTAS

II. MERS-CoV RBD Based Vaccines

The sequence of MERS-CoV S protein and amino acid numbering are noted above. The MERS-CoV RBD used in RBD-based vaccine design is defined as E382-K587 (see SEQ ID NO:5). A trimerization motif, the viral capsid protein SHP (PDB: 1TD0), can be added to the C-terminus of MERS-CoV RBD with a short 5GS linker in between to stabilize RBD in a trimeric conformation. A His6-tag can be added to the C-terminus of the trimerization motif with a 1GS linker to facilitate purification.

SpyTag and SpyCatcher can be attached to MERS-CoV RBD and a nanoparticle subunit in different combinations to facilitate the multivalent display of RBD on nanoparticle. For example, if the C-terminus of RBD is fused to the N-terminus of SpyTag with a 5GS linker, the C-terminus of SpyCatcher can be fused to the N-terminus of a nanoparticle subunit with a 5GS linker to create a pair. SpyTag and SpyCatcher can be switched in these two constructs to create a different pair. SpyTag or SpyCatcher can also be fused to the N-terminus of RBD with a 5GS linker. When the two constructs are introduced into and expressed in the host cells, a recombinant vaccine protein will be formed through the binding between the SpyTag and SpyCatcher motifs.

MERS-CoV RBD (SEQ ID NO:5)

ECDFSPLLSGTPPQVYNFKRLVFTNCNYNLTKLLSLFSVNDFTCSQISP

AAIASNCYSSLILDYFSYPLSMKSDLSVSSAGPISQFNYKQSFSNPTCL

ILATVPHNLTTITKPLKYSYINKCSRLLSDDRTEVPQLVNANQYSPCVS

IVPSTVWEDGDYYRKQLSPLEGGGWLVASGSTVAMTEQLQMGFGITVQY

GTDTNSVCPK

SpyTag: VPTIVMVDAYKRYK (SEQ ID NO:16).
SpyCatcher: SEQ ID NO:17:

AMVTTLSGLSGEQGPSGDMTTEEDSATHIKFSKRDEDGRELAGATMELR

DSSGKTISTWISDGHVKDFYLYPGKYTFVETAAPDGYEVATAITFTVNE

QGQVTVNGEATKGDAHTAS

III. SARS-CoV-2 RBD Based Vaccines

The sequence of SARS-CoV-2 S protein and amino acid numbering are noted above. The SARS-CoV-2 RBD used in RBD-based vaccine design is defined as P330-N532 (see SEQ ID NO:6). A trimerization motif, the viral capsid protein SHP (PDB: 1TD0), can be added to the C-terminus of SARS-CoV-2 RBD with a short 5GS linker in between to stabilize RBD in a trimeric conformation. A His6-tag can be added to the C-terminus of the trimerization motif with a 1GS linker to facilitate purification.

SpyTag and SpyCatcher can be attached to SARS-CoV-2 RBD and a nanoparticle subunit in different combinations to facilitate the multivalent display of RBD on nanoparticle. For example, if the C-terminus of RBD is fused to the N-terminus of SpyTag with a 5GS linker, the C-terminus of SpyCatcher can be fused to the N-terminus of a nanoparticle subunit with a 5GS linker to create a pair. SpyTag and SpyCatcher can be switched in these two constructs to create a different pair. SpyTag or SpyCatcher can also be fused to the N-terminus of RBD with a 5GS linker. When the two constructs are introduced into and expressed in the host cells, a recombinant vaccine protein will be formed through the binding between the SpyTag and SpyCatcher motifs.

SARS-CoV-2 RBD (SEQ ID NO:6):

PNITNLCPFGEVFNATRFASVYAWNRKRISNCVADYSVLYNSASFSTFK

CYGVSPTKLNDLCFTNVYADSFVIRGDEVRQIAPGQTGKIADYNYKLPD

DFTGCVIAWNSNNLDSKVGGNYNYLYRLFRKSNLKPFERDISTEIYQAG

STPCNGVEGFNCYFPLQSYGFQPTNGVGYQPYRVVVLSFELLHAPATVC

GPKKSTN

SpyTag: VPTIVMVDAYKRYK (SEQ ID NO:16).
SpyCatcher: SEQ ID NO:17:

AMVTTLSGLSGEQGPSGDMTTEEDSATHIKFSKRDEDGRELAGATMELR

DSSGKTISTWISDGHVKDFYLYPGKYTFVETAAPDGYEVATAITFTVNE

QGQVTVNGEATKGDAHTAS

Example 3 Production and Purification of S Trimers and RBD Domains

Cell line: All constructs were expressed in HEK293 F cells and ExpiCHO cells, with ExpiCHO showing significantly higher yield.

Purification: After transient expression, S antigens were purified from the supernatant using three methods including the His6-tag/nickel column and antigen-specific antibody column. The S230 and CR3022 antibody columns can be used to purify SARS-CoV S and RBD antigens and nanoparticles. The MCA1 antibody column can be used to purify MERS-CoV S and RBD antigens and nanoparticles; The CR3022 antibody column can be used to purify SARS-CoV-2 S and RBD antigens and nanoparticles.

Example 4 Rational Design of Scaffolded RBD Trimer and RBD-Presenting SApNPs We hypothesized that RBD attached to a trimeric scaffold can mimic the "RBD-up" spike conformation and elicit NAbs to block ACE2 binding. To test this possibility, we designed a fusion construct containing SARS-CoV-1/2 RBD, a short 5-aa $G_4S$ linker (with a 2-aa restriction site), and a trimeric viral capsid protein, SHP (PDB: 1TD0). Structural modeling showed that the three tethered RBDs form a triangle of 92 Å (measured for L492), which is 14 and 18 Å wider than the SARS-CoV-1 "two-RBD-up" spike (PDB: 6CRX, measured for L478) and the MERS-CoV "all-RBD-up" spike (PDB: 5X59, measured for L506), respectively, allowing NAb access to each RBD. We then developed an immunoaffinity chromatography (IAC) column to facilitate tag-free vaccine purification. Previously, NAb-derived IAC columns have been used to purify HIV-1 Env trimers/NPs, hepatitis C virus (HCV) E2 cores/NPs, and Ebola virus (EBOV) GP trimers/NPs. It was reported that a SARS-CoV-1 NAb, CR3022, can bind SARS-CoV-2 RBD (Tian et al., Emerg. Microbes Infect. 9, 382-385, 2020). The SARS-CoV-2 RBD/CR3022 structure revealed the epitope shared by two SARS-CoVs and alluded to a breathing motion of the spike that enables CR3022 binding to RBD. Here, we examined the utility of CR3022 in IAC columns. The SARS-CoV-1/2 RBD-5GS-1TD0 constructs were transiently expressed in 100-ml ExpiCHO cells and purified on a CR3022 antibody column prior to size-exclusion chromatography (SEC) using a Superdex 200 10/300 GL column. While the SARS-CoV-1 RBD construct showed both aggregate (8.6 ml) and trimer (12.7 ml) peaks in the SEC profile, the SARS-CoV-2 RBD construct produced a single trimer peak at 12.8 ml. In sodium dodecyl sulfate-polyacrylamide gel electrophoresis (SDS-PAGE), a monomer band of ~37 kD and a trimer band of ~100 kD were observed under reducing and non-reducing conditions, respectively. Antigenicity was assessed for the two scaffolded RBD trimers in enzyme-linked immunosorbent assay (ELISA) after CR3022/SEC purification. RBD-specific NAbs targeting SARS-CoV-1 (CR3022, m396, 80R, and 5230) and SARS-CoV-2 (B38, CB6, 5309 from a SARS survivor, and P2B-2F6), were tested in ELISA. Overall, similar half maximal effective concentration ($EC_{50}$) values were observed for the two RBD trimers binding to their respective NAbs. The SARS-CoV-1 RBD trimer showed greater binding affinity for CR3002 than its SARS-CoV-2 counterpart with a 1.3-fold difference in the $EC_{50}$ value. Of the SARS-CoV-2 NAbs, B38 yielded a similar $EC_{50}$ value to CR3022. The kinetics of antibody binding was measured using biolayer interferometry (BLI). Overall, all tested antibodies exhibited a fast on-rate but with visible differences in their off-rates. For example, B38 showed a faster off-rate than other SARS-CoV-2 NAbs, while CR3022, the antibody used to purify SARS-CoV-1/2 RBD proteins, exhibited comparable kinetic profiles.

We then hypothesized that the SpyTag/SpyCatcher (or simply SPY) system can be used to conjugate RBD to SApNPs to create multivalent RBD vaccines capable of eliciting a more potent NAb response. The 13-aa SpyTag spontaneously reacts with the SpyCatcher protein to form an irreversible isopeptide bond. The SPY system has been used to attach antigens to SApNPs and VLPs. Here, SpyTag was fused to the C terminus of RBD, while SpyCatcher was fused to the N terminus of an SApNP subunit, both with a 5-aa $G_4S$ linker. This design was first tested for FR. We compared two production strategies—co-expression of RBD-5GS-SpyTag and SpyCatcher-5GS-FR versus supernatant mix after separate expression—and performed purification on a CR3022 column. Protein obtained from transient transfection in 50-ml ExpiCHO cells was analyzed by SEC on a Superose 6 10/300 GL column. Both production strategies produced a peak (12 ml) corresponding to SApNPs. While the SARS-CoV-2 construct notably outperformed its SARS-CoV-1 counterpart in particle yield (0.6-1.0 mg versus 0.3-0.5 mg after CR3022/SEC), supernatant mix appeared to be superior to co-expression. Nonetheless, the results suggest that both strategies can be used to produce RBD-conjugated SApNPs in Good manufacturing practice (GMP)-compatible Chinese hamster ovary (CHO) cells. Antigenicity was assessed for SEC-purified RBD-5GS-SPY-5GS-FR SApNPs. In ELISA, RBD-presenting SApNPs showed slightly improved mAb binding, as indicated by lower $EC_{50}$ values. In BLI, a more pronounced effect of multivalent display on antigenicity was observed, showing notably increased binding signals and plateaued dissociation.

Structural integrity of various RBD SApNPs was analyzed by negative stain EM. For SARS-CoV-1, an RBD-10GS-FR construct was included for comparison that produced very few SApNPs. In contrast, the RBD-5GS-SPY-5GS-FR construct produced SApNPs with visible surface decorations. For SARS-CoV-2, the purified RBD-5GS-SPY-5GS-FR SApNPs, irrespective of the production strategy, showed morphologies corresponding to well-formed nanoparticles. Following a similar strategy, SARS-CoV-1/2 RBDs were also attached to a multilayered I3-01v9 SApNP (He et al., bioRxiv, 2020.2008.2022.262634, 2020). Despite the modest yield, large SApNPs were observed in EM.

In summary, we demonstrate the utility of the SPY system for rapid development of RBD-based SApNP vaccines. Compared to the two-component RBD SApNPs, the SPY-linked RBD SApNPs presented here may be more advantageous in terms of stability and manufacturability.

Example 5 Rational Design of Prefusion Spike Through Minimizing Metastability

It is imperative to understand the SARS-CoV-2 spike metastability, and based on which, to design the optimal spike as a vaccine antigen. We first created the His-tagged, uncleaved spike ectodomain ($S_{ECTO}$) constructs for SARS-CoV-1/2, both containing the 2P mutation and a trimerization motif (1TD0) fused to the C terminus with a $G_4S$ linker. The two constructs were transiently expressed in 50-ml ExpiCHO cells followed by purification on a Nickel column or a CR3022 column. The $S2P_{ECTO}$-5GS-1TD0-$His_6$ protein was characterized by SEC on a Superose 6 10/300 GL column. After Nickel column, both $S2P_{ECTO}$ constructs showed a trimer peak (~12 ml) with shoulders to the left and right indicative of aggregate and dimer/monomer species, respectively. CR3022 purification resulted in a consistent trimer peak and less dimer/monomer species. We then tested a pair of $S_{ECTO}$ constructs containing a double glycine mutation (V1060G/L1061G, termed 2G). The 2G mutation had little effect on the SARS-CoV-1 spike but produced an abnormal SEC profile and showed no yield for the SARS-CoV-2 spike after purification by Nickel and CR3022 columns, respectively. Lastly, we tested a pair of S2G variants without the HR2 stalk (E1150-Q1208), termed S2GΔHR2. Deletion of the HR2 stalk restored the SARS-CoV-2 trimer peak and reduced aggregates for both SARS-CoVs, as shown by the SEC profiles upon CR3022 purification.

We hypothesized that HR2 may be a key determinant of SARS-CoV spike metastability. It is possible that the interactions between HR1 and HR2 of two neighboring spikes may facilitate the pre-to-post-fusion transition in addition to ACE2 binding and S1 dissociation. Given the extensive mutations in HR1 (9 in total) compared to SARS-CoV-1, we sought to examine the role of HR1 in SARS-CoV-2 spike metastability with two HR1-swapped spike constructs. Interestingly, while HR1 swapping proved ineffective, deletion of the HR2 stalk once again restore the trimer peak. Therefore, S2GΔHR2 provides a general spike design for SARS-CoV-1/2 and perhaps other CoVs. Four separate production runs of SARS-CoV-2 S2GΔHR2-5GS-1TD0 in 300-ml ExpiCHO cells resulted in nearly identical SEC profiles with a trimer yield of 0.8-1.0 mg. Blue native polyacrylamide gel electrophoresis (BN-PAGE) confirmed the purity of the S2GΔHR2 spike across SEC fractions. Antigenicity was assessed for freshly produced SARS-CoV-2 $S2P_{ECTO}$ and S2GΔHR2 spikes. In ELISA, the S2GΔHR2 spike showed consistently higher affinity for the five representative mAbs than the $S2P_{ECTO}$ spike. When tested against three newly identified NAbs, C105 and CC12.1/CC12.3, the two spikes yielded similar $EC_{50}$ values. In BLI, the S2GΔHR2 spike showed higher binding signals than the $S2P_{ECTO}$ spike at the highest concentration, while exhibiting similar binding kinetics. The use of NAb P2B-2F6 for spike purification resulted in much higher trimer yield with similar purity to the CR3022 column across SEC fractions.

Together, we demonstrate that deletion of the HR2 stalk may improve spike properties and S2GΔHR2 may provide a better spike antigen that improves on the 2P mutation.

Example 6 Rational Design of Single-Component and Multilayered SApNPs

Although it was proven possible to conjugate trimeric SARS-CoV-2 spikes to an SApNP using the SPY system, the random and irreversible chemical linking will result in irregular display with unoccupied but spatially occluded anchoring sites on the surface. The SPY system is perhaps more suitable for individual antigens such as RBD. We therefore set out to obtain rational design of single-component, multilayered, self-assembling spike nanoparticles, using the gene fusion approach.

Native SARS-CoV-2 virions present both pre- and postfusion spikes on the surface. Our vaccine strategy aims to develop single-component, multilayered SApNPs that each present 8 or 20 stable S2GΔHR2 spikes to the immune system. To explore this possibility, we modeled the S2GΔHR2 spike on FR with a 5-aa $G_4S$ linker, on E2p with a 5-aa $G_4S$ linker, and on I3-01v9 with a 10-aa $(G_4S)_2$ linker, resulting in large SApNPs with diameters of 47.9 nm, 55.9 nm, and 59.3 nm, respectively. The three S2GΔHR2 SApNP constructs were transiently expressed in 400-ml ExpiCHO cells followed by CR3022 purification and SEC on a Superose 6 10/300 GL column. Three separate production runs generated highly consistent SEC profiles for all three constructs, despite the variation of low-m.w. impurities observed for FR and E2p SApNPs. Following CR3022/SEC purification, we obtained on average 0.3-0.4 mg, 0.15-0.25 mg, and 0.3-0.35 mg SApNP for S2GΔHR2-5GS-FR, S2GΔHR2-5GS-E2p-LD4-PADRE (or E2p-L4P), and S2GΔHR2-10GS-I3-01v9-LD7-PADRE (or I3-01v9-L7P). Overall, S2GΔHR2-10GS-I3-01v9-L7P appeared to be the best performer in terms of yield, purity, and stability in production.

The structural integrity of CR3022/SEC-purified SApNPs was characterized by negative stain EM, which showed well-formed particles in the range of 40-60 nm, consistent with the modeling. Spikes could be readily recognized on the SApNP surface. Antigenicity of S2GΔHR2-presenting SApNPs was assessed using the same panel of mAbs/NAbs. In ELISA, three SApNPs showed slightly improved binding to some, but not all, of the antibodies compared to the individual spike. In BLI, we observed a clear correlation between peak binding signal and antigen valency, with a ranking of E2p/I3-01v9>FR>spike. Display on the two 60-mers significantly improved antibody binding compared to the 24-mer, FR.

In summary, these large VLP-size SApNPs with 8 or 20 spikes on the surface provide promising vaccine candidates for in vivo evaluation.

Example 7 SARS-CoV-1/2 Vaccine-Induced Binding Antibody Response

Figure 2:
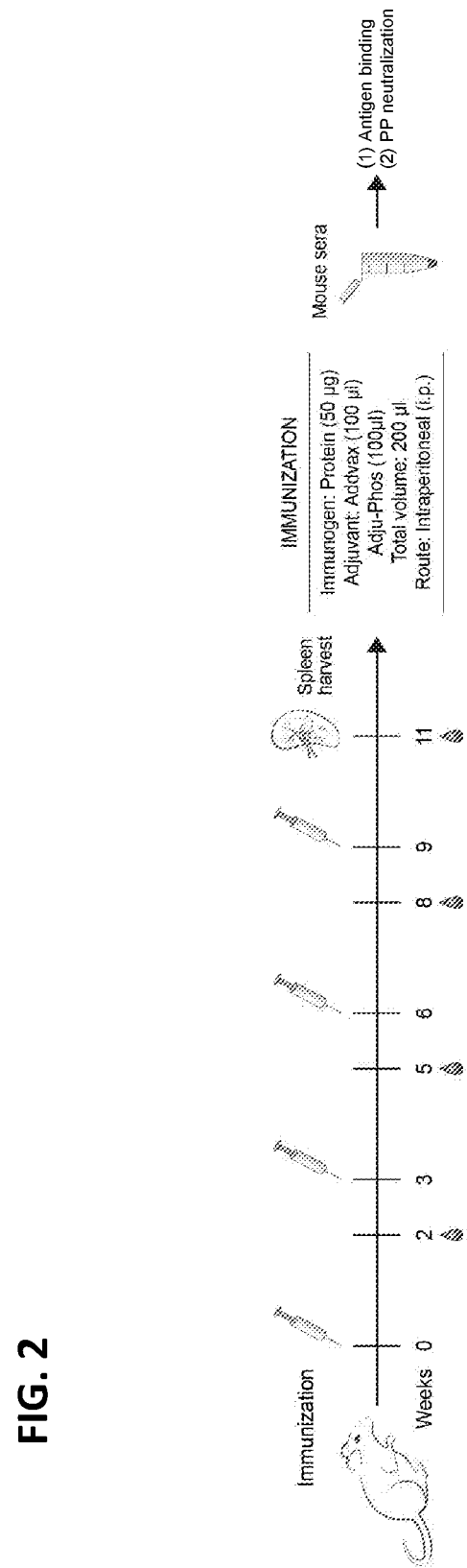
FIG. 2 is a schematic representation of the mouse immunization protocol. Groups of five mice were immunized four times with three-week intervals. All vaccine antigens (50 ug/injection) were formulated with AddaVax, an oil-in-water emulsion adjuvant, except for I3-01v9, which was formulated with aluminum phosphate (AP). The injections were done through the intraperitoneal (IP) route. Blood samples were collected two weeks after each injection.

Selected SARS-CoV-1/2 RBD- and spike-based immunogens were evaluated in BALB/c mice to evaluate vaccine-induced antibody response (FIG. 2). Groups of five mice were immunized four times with three-week intervals. All vaccine antigens were formulated with AddaVax, an oil-in-water emulsion adjuvant, except for the I3-01v9 SApNP, which was formulated with aluminum phosphate (AP). We first performed a longitudinal analysis of binding antibody response as measured by half maximal effective dilution ($ED_{50}$) in the two SARS-CoV-2 RBD vaccine groups. Results from the study are shown in FIG. 3. The RBD SApNP (RBD-5GS-SPY-5GS-FR) elicited significantly higher $ED_{50}$ titers than the scaffolded RBD trimer (RBD-5GS-1TD0) at w2 and w5, irrespective of the coating antigen, and showed a P value of 0.0009 at w8 when RBD was coated. Compared to the stabilized spike (S2GΔHR2-5GS-1TD0), the RBD SApNP elicited significantly higher $ED_{50}$ titers against RBD at w2, w5, and w8, demonstrating a strong "epitope-focusing" effect. Mouse sera bound the SARS-CoV-1 spike with lower $ED_{50}$ titers than the SARS-CoV-2 spike but with similar patterns). We then performed a longitudinal analysis of binding antibody response induced by two SARS-CoV-2 spikes, $S2P_{ECTO}$-5GS-1TD0 and S2GΔHR2-5GS-1TD0, and three SApNPs each displaying 8 or 20 S2GΔHR2 spikes. The S2GΔHR2 spike elicited 2~3-fold higher average $ED_{50}$ titers than the $S2P_{ECTO}$ spike irrespective of the coating antigen, showing greater immunogenicity (of note, to facilitate a fair comparison, mouse sera from the two spike groups were tested against their respective spikes).

Three SApNPs exhibited different temporal patterns depending on the coating antigen. When spike was used as the coating antigen, the I3-01v9 group showed a steady increase in average $ED_{50}$ titer over time. This SApNP yielded the highest average $ED_{50}$ titer at two time points, w2 and w8, and significantly outperformed the $S2P_{ECTO}$ spike at all time points. The smaller FR exhibited a similar temporal pattern with lower average $ED_{50}$ titers, which are still significantly higher than that of the $S2P_{ECTO}$ group. Among the three SApNPs, E2p registered the lowest average $ED_{50}$ titer at w2 and reached the highest at w5, which decreased slightly at w8. In terms of RBD-specific response, the five groups showed a clear ranking based on their average $ED_{50}$ titers, which remained consistent across time points. At w2, I3-01v9 elicited an average $ED_{50}$ titer of 175, whereas all other spike-based vaccine groups showed little RBD-specific response. At w5 and w8, S2GΔHR2 elicited higher $ED_{50}$ titers (on average by 2-fold) than $S2P_{ECTO}$, while all three SApNPs outperformed the individual S2GΔHR2 spike with a ranking of $ED_{50}$ titers correlated with their size (FR<E2p<I3-01v9). Sera reacted with the SARS-CoV-1 spike similarly, albeit at a lower level.

Lastly, we compared binding antibody responses induced by three SARS-CoV-1 vaccines—the $S2P_{ECTO}$ spike ($S2P_{ECTO}$-5GS-1TD0), the scaffolded RBD trimer (RBD-5GS-1TD0), and the RBD SApNP (RBD-5GS-SPY-5GS-FR). Based on the $ED_{50}$ titers, the SARS-CoV-1 $S2P_{ECTO}$ spike appeared to be more immunogenic than the SARS-CoV-2 S2GΔHR2 spike, whereas the SARS-COV-1 RBD SApNP was less advantageous than its SARS-COV-2 counterpart. Serum reactivity with the SARS-CoV-2 $S2P_{ECTO}$ spike was observed for all three SARS-CoV-1 vaccine groups.

Our results thus indicate that RBD SApNPs can elicit RBD-specific antibody titers at a similar or higher level compared to the spike. Furthermore, the S2GΔHR2 spike is more immunogenic than the widely used $S2P_{ECTO}$ spike, in addition to its superior in-vitro properties. The large multilayered E2p and I3-01v9 SApNPs are the best performers among all the spike-based vaccines, consistent with the findings in our previous HIV-1, HCV, and Ebola vaccine studies.

Example 8 SARS-CoV-1/2 Vaccine-Induced NAb Response

One major goal in COVID-19 vaccine development is to generate a potent NAb response that can protect against SARS-CoV-2 infection. Pseudoparticle (SARS-CoV-1/2-pp) neutralization assays were used to evaluate serum NAb responses elicited by different vaccine candidates. As indicated by the results shown in FIG. 4, we first performed a longitudinal analysis of NAb response as measured by half maximal inhibitory dilution ($ID_{50}$) in the two SARS-CoV-2 RBD vaccine groups. The RBD SApNP elicited low titers of NAb response against autologous SARS-CoV-2 at as early as w2 and retained its advantage at the two later time points, suggesting that such RBD SApNP vaccines can elicit a rapid NAb response upon vaccination. The scaffolded RBD trimer group showed the lowest average $ID_{50}$ titer at w5 but a NAb response comparable to that induced by the stabilized S2GΔHR2 spike at w8. A somewhat different pattern was observed in the SARS-CoV-1-pp assay. At the first time point, w2, no vaccine groups showed any detectable heterologous NAb response. At w5 and w8, the S2GΔHR2 spike elicited a more potent SARS-CoV-1 NAb response than both RBD-based vaccines, suggesting that non-RBD epitopes may contribute to the cross-neutralization.

We then performed a longitudinal analysis of NAb responses induced by five spike-based vaccines. In terms of autologous neutralization, no spike-based vaccine elicited any SARS-CoV-2-pp NAb response at w2 after the first injection. But a consistent pattern was observed for serum neutralization at w5 and w8: the $S2P_{ECTO}$ spike used in almost all vaccine candidates currently in human trials showed the lowest average $ID_{50}$ titers, 879 and 2481 at w5 and w8, respectively; the newly designed S2GΔHR2 spike induced a stronger NAb response than the $S2P_{ECTO}$ spike with 2.8-6.7-fold higher average $ID_{50}$ titers, confirming the beneficial effect of the 2P-to-2G substitution and deletion of the HR2 stalk; among the three SApNPs, E2p was the best performer at w5, showing an average $ID_{50}$ titer of 8493 that is 9.7-fold higher than $S2P_{ECTO}$ and 1.4-fold higher than S2GΔHR2, while I3-01v9 showed the most potent NAb response at w8 with an average $ID_{50}$ titer of 17351 that is 7-fold and 2.5-fold higher than $S2P_{ECTO}$ and S2GΔHR2, respectively. A similar temporal pattern of NAb response was observed in the heterologous SARS-CoV-1-pp assay. It is worth noting that the I3-01v9 SApNP elicited a SARS-CoV-1 NAb response with an average $ID_{50}$ titer of 351 at w2, whereas all other groups showed no detectable neutralization. Nonetheless, our results suggest that the SARS-CoV-2 S2GΔHR2-based vaccines, particularly SApNPs, may provide protection against both SARS-CoV-1/2. Lastly, we performed a longitudinal analysis of NAb responses induced by three SARS-CoV-1 vaccines. In the autologous SARS-CoV-1-pp assay, the $S2P_{ECTO}$ spike and the RBD SApNP induced significantly more potent NAb responses than the scaffolded RBD trimer at w2 and w5 and all three vaccine groups showed similar $ID_{50}$ titers at w8. However, heterologous SARS-CoV-2 neutralization was below or at the baseline level for three SARS-CoV-1 vaccines at w2, w5, and w8.

Our results thus demonstrate the advantage of the S2GΔHR2 spike and S2GΔHR2-presenting SApNPs with respect to the $S2P_{ECTO}$ spike in NAb elicitation. While the SARS-CoV-2 RBD- and S2GΔHR2-presenting SApNPs are comparable in eliciting SARS-CoV-2-specific NAb response, the latter may provide a broader protection against SARS-associated CoVs.

Example 9 T-Cell Response and Vaccine Safety

While the humoral immunity is required to block host-virus interaction and prevent viral infection, the cellular immunity is essential for eliminating infected host cells to control viral infection. Emerging evidence indicates that an early T-cell response, as well as T-cell memory, is critical for protection against SARS-CoV-2. However, COVID-19 vaccines must induce a CD4$^+$ T helper 1 (Th1), but not Th2-type, T-cell response, as the latter has been linked to vaccine-associated enhancement of respiratory disease (VAERD). In addition, T follicular helper cells (Tfh) play an important role in the maturation and production of NAbs. Therefore, understanding T-cell response is crucial for the development of an effective and safe COVID-19 vaccine.

Figure 5:
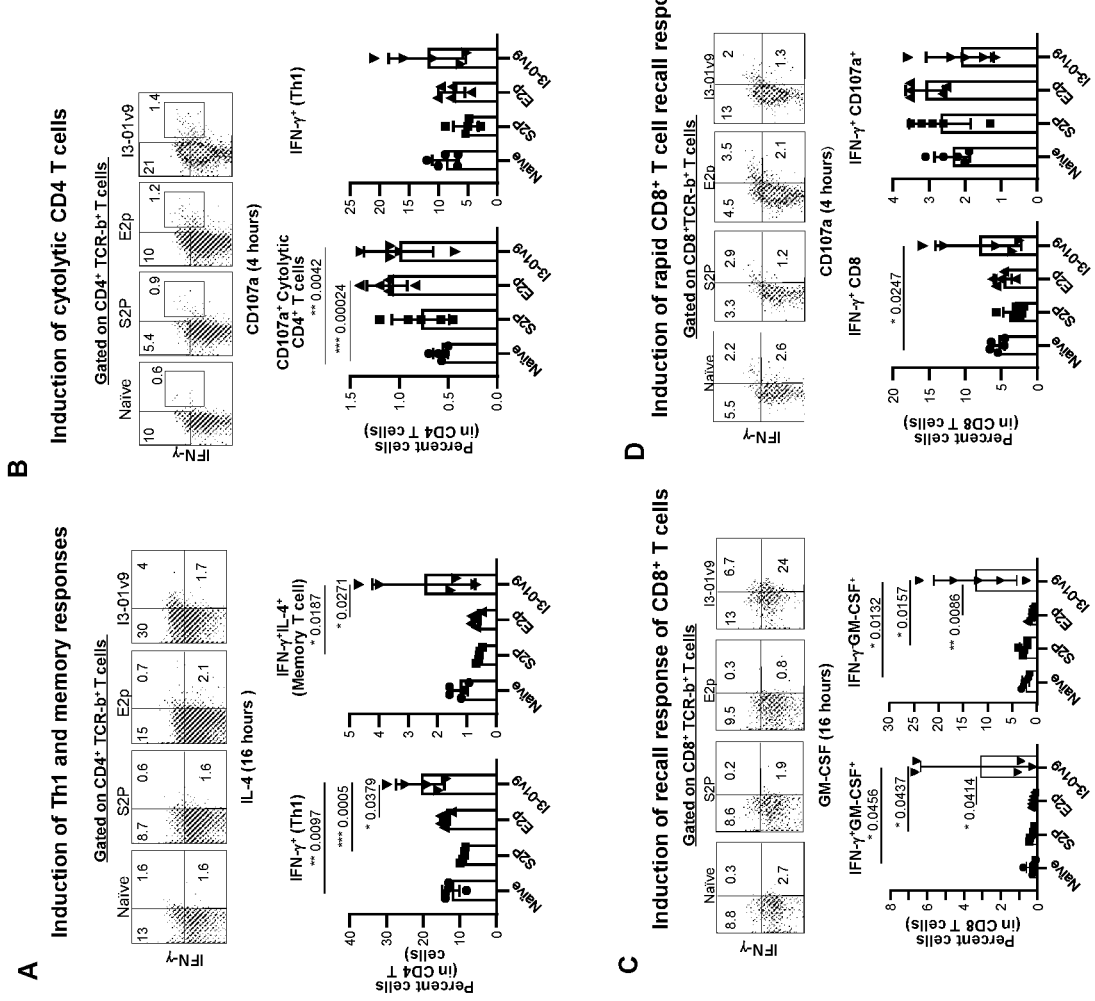
FIG. 5 shows results of SARS-CoV-2 vaccine-induced T-cell responses in mice. (A)-(B): Vaccine-induced CD4+ T cell immunity. Splenocytes derived from mice at w11 were cultured in the presence of DC-pulsed with the S2PECTO spike (1×10-7 mM), E2p SApNP (1×10-7 mM) and I3-01v9 SApNP (1×10-7 mM) for 16 hours (A) and 4 hours (B), respectively. (C)&(D): Vaccine-induced CD8+ T cell immunity. Splenocytes derived from mice at w11 were cultured in the presence of DC-pulsed with the S2PECTO spike (1×10-7 mM), E2p SApNP (1×10-7 mM) and I3-01v9 SApNP (1×10-7 mM) for 16 hours (C) and 4 hours (D), respectively. Splenocytes from five naïve mice were used as the control samples and cultured with PBS. Plots show the frequencies of cell fraction. The P values were determined by one-way ANOVA analysis. *, $P<0.05$; , $P<0.01$; *, $P<0.001$.

Interferon (IFN)-γ-producing Th1 cells are important for generating an optimal antibody response and for the induction of cellular immunity to clear viruses. We first examined the impact of various SARS-CoV-2 vaccine formulations on the induction of CD4$^+$ Th1 responses specific to the spike protein at w11—two weeks after the fourth immunization, when memory T cells had already developed in spleen. Mouse splenocytes from the S2P group and two SApNP groups (E2p and I3-01v9) were analyzed by flow cytometry (FC) using naïve samples as a negative control. Results from the studies are shown in FIG. 5. I3-01v9 induced approximately 1.5- and 2.3-fold higher frequency of IFN-γ-producing CD4$^+$ Th1 cells than S2P and E2p, respectively. Notably, following re-stimulation with the respective antigens for as few as 4 hours, both E2p and I3-01v9 groups produced ~2-fold higher frequency of CD107a-producing cytolytic CD4$^+$ T cells than the S2P and naïve control groups. IFN-γ/IL-4 (interleukin-4) double-positive cells are memory CD4$^+$ T cells that have acquired the ability to produce IL-4 while still retaining the ability to produce IFN-γ under Th1 conditions. It appeared that I3-01v9 induced 3- and 5-fold more IFN-γ/IL-4 double-positive memory CD4$^+$ T cells than S2P and E2p. These results suggest that I3-01v9 can induce both potent CD4$^+$ Th1 cells and IFN-γ/IL-4 double-positive memory CD4$^+$ T cells.

In addition, I3-01v9 induced more IFN-γ/GM-CSF (granulocyte-macrophage colony-stimulating factor) double-positive CD8$^+$ effector T cells than S2P and E2p, as shown in FIG. 5. These data suggest that protective CD8$^+$ T cell responses were also generated in mice immunized with the I3-01v9 SApNP. Of note, CD8$^+$ T cells derived from mice immunized with I3-01v9, rather than those with S2P and E2p, acquired the ability to rapidly produce IFN-γ upon antigen re-stimulation, suggesting the generation of I3-01v9-responsive effector/memory T cells. Together, our findings indicate that the S2GΔHR2 I3-01v9 SApNP can induce potent T-cell responses in mice consisting of CD4$^+$ Th1 cells, IFN-γ/IL-4 double-positive memory CD4$^+$ T cells, and CD8$^+$ T cells, thus providing protective cellular immunity required for an effective vaccine against SARS-CoV-2.

Example 10 Some Exemplified Methods

Design, expression and purification of SARS-CoV-2 RBD and spike antigens: The spike (S) genes of the SARS-CoV-1 isolate Tor2 (GenBank accession #: NC_004718) and the SARS-CoV-2 isolate Wuhan-Hu-1 (GenBank accession #: MN908947) were used to design all the RBD and spike constructs following codon-optimization for expression in mammalian cells. The RBD sequence is defined as P317-D518 and P330-N532 for SARS-CoV-1 and 2, respectively. The $S_{ECTO}$ sequence is defined as M1-Q1190 and M1-Q1208 for SARS-CoV-1 and 2, respectively. To remove the S1/S2 cleavage site, an R667G mutation and a $^{682}$GSAGSV$^{687}$ (SEQ ID NO:18) modification were introduced in the SARS-CoV-1 and 2 spikes, respectively. The 2P (or 2G) mutation was made to K968/V969 and K986/V987 in the SARS-CoV-1 and 2 spikes, respectively. The SARS-CoV-2 C-terminal region (E1150-Q1208) containing the HR2 stalk was removed from S2G$_{ECTO}$, resulting in an HR2-deleted spike construct termed S2GΔHR2. The viral capsid protein SHP (PDB: 1TD0) was used as a trimerization motif in spike constructs for immunization, whereas the foldon domain from the bacteriophage T4 fibritin (PDB: 1RFO) was used in coating spike antigens for ELISA to mask the 1TD0-derived antibody response. All constructs were transiently expressed in ExpiCHO cells (Thermo Fisher). Briefly, ExpiCHO cells were thawed and incubated with ExpiCHO™ Expression Medium (Thermo Fisher) in a shaker incubator at 37° C., 135 rpm and 8% $CO_2$. When the cells reached a density of $10\times10^6$ $ml^{-1}$, ExpiCHO™ Expression Medium was added to reduce cell density to $6\times10^6$ $ml^{-1}$ for transfection. The ExpiFectamine™ CHO/plasmid DNA complexes were prepared for 100-ml transfection in ExpiCHO cells following the manufacturer's instructions. For a given construct, 100 μg of plasmid and 320 μl of ExpiFectamine™ CHO reagent were mixed in 7.7 ml of cold OptiPRO™ medium (Thermo Fisher). After the first feed on day one, ExpiCHO cells were cultured in a shaker incubator at 33° C., 115 rpm and 8% $CO_2$ following the Max Titer protocol with an additional feed on day five (Thermo Fisher). Culture supernatants were harvested 13 to 14 days after transfection, clarified by centrifugation at 4000 rpm for 25 min, and filtered using a 0.45 μm filter (Thermo Fisher). The CR3022 antibody column was used to extract SARS-CoV-1/2 antigens from the supernatants, which was followed by SEC on a Superdex 200 10/300 GL column (for scaffolded RBD trimer) or a Superose 6 10/300 GL column (for RBD-SPY-NPs, spikes, and spike-presenting NPs). For comparison, His-tagged $S_{ECTO}$-5GS-1TD0 spike protein was extracted from the supernatants using an immobilized Ni Sepharose™ Excel column (GE Healthcare) and eluted with 500 mM Imidazole prior to SEC. Protein concentration was determined using $UV_{280}$ absorbance with theoretical extinction coefficients.

Blue native polyacrylamide gel electrophoresis: SARS-CoV-2 spikes and spike-presenting NPs were analyzed by blue native polyacrylamide gel electrophoresis (BN-PAGE) and stained with Coomassie blue. The proteins were mixed with sample buffer and G250 loading dye and added to a 4-12% Bis-Tris NativePAGE™ gel (Life Technologies). BN-PAGE gels were run for 2 to 2.5 hours at 150 V using the NativePAGE™ running buffer (Life Technologies) according to the manufacturer's instructions.

Enzyme-linked immunosorbent assay: Each well of a Costar™ 96-well assay plate (Corning) was first coated with 50 μl PBS containing 0.2 μg of the appropriate antigens. The plates were incubated overnight at 4° C., and then washed five times with wash buffer containing PBS and 0.05% (v/v) Tween 20. Each well was then coated with 150 μl of a blocking buffer consisting of PBS, 40 mg $ml^{-1}$ blotting-grade blocker (Bio-Rad), and 5% (v/v) FBS. The plates were incubated with the blocking buffer for 1 hour at room temperature, and then washed five times with wash buffer. For antigen binding, antibodies were diluted in the blocking buffer to a maximum concentration of 5 μg $ml^{-1}$ followed by a 10-fold dilution series. For each antibody dilution, a total of 50 μl volume was added to the appropriate wells. For mouse sample analysis, serum or plasma was diluted by 20-fold in the blocking buffer and subjected to a 10-fold dilution series. For each sample dilution, a total of 50 μl volume was added to the wells. Each plate was incubated for 1 hour at room temperature, and then washed 5 times with PBS containing 0.05% Tween 20. For antibody binding, a 1:5000 dilution of goat anti-human IgG antibody (Jackson ImmunoResearch Laboratories, Inc), or for mouse sample analysis, a 1:3000 dilution of horseradish peroxidase (HRP)-labeled goat anti-mouse IgG antibody (Jackson ImmunoResearch Laboratories), was then made in the wash buffer (PBS containing 0.05% Tween 20), with 50 μl of this diluted secondary antibody added to each well. The plates were incubated with the secondary antibody for 1 hour at room temperature, and then washed 5 times with PBS containing 0.05% Tween 20. Finally, the wells were developed with 50 μl of TMB (Life Sciences) for 3-5 min before stopping the reaction with 50 μl of 2 N sulfuric acid. The resulting plate readouts were measured at a wavelength of 450 nm. Of note, the w2 serum binding did not reach the plateau (or saturation) to allow for accurate determination of $ED_{50}$ titers. Nonetheless, the $ED_{50}$ values at w2 were derived by setting the lower/upper constraints of $OD_{450}$ at 0.0/3.2 to facilitate the comparison of different vaccine groups at the first time point.

Bio-layer interferometry: The kinetics of SARS-CoV-1/2 vaccine antigens, RBD versus RBD-presenting NPs as well as spike versus spike-presenting NPs, binding to a panel of known antibodies was measured using an Octet RED96 instrument (FortéBio, Pall Life Sciences). All assays were performed with agitation set to 1000 rpm in FortéBio 1× kinetic buffer. The final volume for all the solutions was 200 μl per well. Assays were performed at 30° C. in solid black 96-well plates (Geiger Bio-One). For all antigens with the exception of S2GΔHR2-NPs, 5 μg $ml^{-1}$ of antibody in 1× kinetic buffer was loaded onto the surface of anti-human Fc Capture Biosensors (AHC) for 300 s. For S2GΔHR2-NPs, anti-human Fc Quantitation Biosensors (AHQ) were used. A 60 s biosensor baseline step was applied prior to the analysis of the association of the antibody on the biosensor to the antigen in solution for 200 s. A two-fold concentration gradient of antigen, starting at 950 nM for scaffolded RBD trimers, 37 nM for RBD-5GS-SPY-5GS-FR NP, 150 nM for spike trimers, and 9/3.5/3.5 nM for S2GΔHR2 presented on FR/E2p/I3-01v9 NPs, was used in a titration series of six. The dissociation of the interaction was followed for 300 s. Correction of baseline drift was performed by subtracting the mean value of shifts recorded for a sensor loaded with antibody but not incubated with antigen and for a sensor without antibody but incubated with antigen. Octet data were processed by FortéBio's data acquisition software v.8.1. Experimental data were fitted with the binding equations describing a 2:1 interaction to achieve optimal fitting. Of note, S2GΔHR2 trimer binding was also measured using AHQ to facilitate the comparison of antibody binding with S2GΔHR2-presenting NPs.

Electron microscopy (EM) assessment of nanoparticle constructs: The initial EM analysis of RBD and S2GΔHR2-presenting NPs was conducted at the Core Microscopy Facility at The Scripps Research Institute. Briefly, NP samples were prepared at the concentration of 0.01 mg/ml. Carbon-coated copper grids (400 mesh) were glow-discharged and 8 μL of each sample was adsorbed for 2 min. Excess sample was wicked away and grids were negatively stained with 2% uranyl formate for 2 min. Excess stain was wicked away and the grids were allowed to dry. Samples were analyzed at 80 kV with a Talos L120C transmission electron microscope (Thermo Fisher) and images were acquired with a CETA 16M CMOS camera.

Animal immunization and sample collection: Similar immunization protocols have been reported in our previous NP vaccine studies. Briefly, the Institutional Animal Care and Use Committee (IACUC) guidelines were followed with animal subjects tested in the immunization study. Eight-week-old BALB/c mice were purchased from The Jackson Laboratory and housed in ventilated cages in environmentally controlled rooms at The Scripps Research Institute, in compliance with an approved IACUC protocol and AAALAC (Association for Assessment and Accreditation of Laboratory Animal Care) International guidelines. Mice were immunized at weeks 0, 3, 6, and 9 with 200 μl of antigen/adjuvant mix containing 50 μg of vaccine antigen and 100 μl of adjuvant, AddaVax or Adju-Phos (InvivoGen), via the intraperitoneal (i.p.) route. Blood was collected two weeks after each immunization. All bleeds were performed through the retro-orbital sinus using heparinized capillary tubes into EDTA-coated tubes. Samples were diluted with an equal volume of PBS and then overlaid on 4.5 ml of Ficoll in a 15 ml SepMate™ tube (STEMCELL Technologies) and spun at 1200 RPM for 10 min at 20° C. to separate plasma and cells. The plasma was heat inactivated at 56° C. for 30 min, spun at 1200 RPM for 10 min, and sterile filtered. The cells were washed once in PBS and then resuspended in 1 ml of ACK Red Blood Cell lysis buffer (Lonza). After washing with PBS, peripheral blood mononuclear cells (PBMCs) were resuspended in 2 ml of Bambanker Freezing Media (Lymphotec). Spleens were also harvested and ground against a 70-μm cell strainer (BD Falcon) to release the splenocytes into a cell suspension. Splenocytes were centrifuged, washed in PBS, treated with 5 ml of ACK lysing buffer (Lonza), and frozen with 3 ml of Bambanker freezing media. Sera were heat inactivated for ELISA binding and pseudovirus neutralization assays.

SARS-CoV-1/2 pseudovirus neutralization assay: Pseudoparticle (SARS-CoV-1/2-pp) neutralization assays were utilized to assess the neutralizing activity of previously reported antibodies and vaccine-induced murine antibody response. SARS-CoV-1/2-pps were generated by co-transfection of HEK293T cells with the HIV-1 pNL4-3.lucR-E- plasmid (the NIH AIDS reagent program) and the expression plasmid encoding the S gene of SARS-CoV-1 isolate Tor2 (GenBank accession #: NC_004718) and the SARS-CoV-2 isolate Wuhan-Hu-1 (GenBank accession #: MN908947) at a 4:1 ratio by lipofectamine 3000 (Thermo Fisher Scientific) . After 48 to 72 hours, SARS-CoV-1/2-pps were collected from the supernatant by centrifugation at 4000 rpm for 10 min, aliquoted, and stored at −80° C. before use. The mAbs at a starting concentration of 0.1-10 μg/ml, or mouse serum at a starting dilution of 100-fold, were mixed with the supernatant containing SARS-CoV-1/2-pps and incubated for 1 hour at 37° C. in white solid-bottom 96-well plate (Corning). A 3-fold dilution series was used in the assay. The HEK293T-hACE2 cell line (catalogue #: NR-52511) and the vector pcDNA3.1(−) containing the SARS-CoV-2 spike gene (catalogue #: NR52420) were obtained from BEI RESOURCES and used in pseudovirus neutralization assays. Briefly, HEK293T-hACE2 cells at $1\times10^4$ were added to each well and the plate was incubated at 37° C. for 48 hours. After incubation, overlying media was removed, and cells were lysed. The firefly luciferase signal from infected cells was determined using the Bright-Glo Luciferase Assay System (Promega) according to the manufacturer's instructions. Data were retrieved from a BioTek microplate reader with Gen 5 software, the average background luminescence from a series of uninfected wells was subtracted from each well, and neutralization curves were generated using GraphPad Prism 8.4.3, in which values from wells were compared against a well containing SARS-CoV-1/2-pp only. The same HIV-1 vectors pseudotyped with the murine leukemia virus (MLV) Env gene, termed MLV-pps, were produced in HEK293T cells and included in the neutralization assays as a negative control.

Dendritic cell (DC) production: Mouse bone marrow (BM) was cultured in RPMI 1640 medium containing 10% fetal bovine serum and recombinant mouse Flt3L (50 ng/mL) and SCF (10 ng/ml) for 9 days. To induce DC activation, immature DCs were incubated with lipopolysaccharide (LPS, 100 ng/mL), R848 (Resiquimod, 100 ng/mL) or CpG (ODN 1585, 1 μM) overnight, which activated Toll-like receptor (TLR)4, TLR7/8 or TLR9 signaling, respectively. Cells were harvested for experiments. pDCs were sorted to isolate CD11c+B220+ cells using FACS cell sorter and magnetic beads (Miltenyi-Biotech, CA).

Antibodies (Abs) and flow cytometry analysis: All antibodies used for immunofluorescence staining were purchased from eBioscience (San Diego, CA), BioLegend (San Diego, CA) or BD Biosciences (San Jose, CA). Magnetic microbead-conjugated Abs and streptavidin were purchased from Miltenyi-Biotech (Auburn, CA). Recombinant human IL-2 protein was purchased from R&D Systems (Minneapolis, MN). Recombinant mouse Flt3 ligand (Flt3L) and mouse SCF were purchased from Shenandoah Biotech (Warwick, PA). Cells were stained with appropriate concentrations of mAbs. Dead cells were excluded using Fixable Viability Dye from eBioscience (San Diego, CA). Flow cytometry analyses were performed using LSRII (BD Bioscience, CA) and Canto cytometers (Becton Dickinson, NJ). Cell were sorted on BD FACSAria II (BD Bioscience, CA).

T cell culture and activation: Splenic mononuclear cells from immunized mice were cultured in the presence of DCs pulsed with or without S2P, E2P and I3-01 in complete IMDM medium containing IL-2 (5.0 ng/ml). Cells were collected 16 hours later for intracellular cytokine staining and flow cytometric analysis.

Statistics: In antibody titer analysis, comparison of different vaccine groups was performed in GraphPad Prism 8.4.3 using the two-tailed unpaired Student's t test. In the T cell analysis, comparison of means was done using the two-tailed unpaired Student's t test, ANOVA and then post-hoc t test. P values of 0.05 or less were considered significant.

The invention thus has been disclosed broadly and illustrated in reference to representative embodiments described above. It is understood that various modifications can be made to the present invention without departing from the spirit and scope thereof.

It is further noted that all publications, sequence accession numbers, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. An engineered immunogen polypeptide derived from the spike (S) protein of a coronavirus, comprising an altered soluble S sequence that has modifications relative to wild-type soluble S sequence of the coronavirus that stabilize the prefusion S structure, wherein the modifications comprise (a) a mutation that inactivates the S1/S2 cleavage site, (b) a mutation in the turn region between the heptad repeat 1 (HR1) region and the central helix (CH) region that prevents HR1 and CH to form a straight helix during fusion, and (c) a truncation of the heptad repeat 2 region (HR2).

2. The immunogen polypeptide of claim 1, wherein the coronavirus is SARS-CoV-2, wherein the mutation inactivating S1/S2 cleavage site comprises substitution of $^{682}$RRAR$^{685}$ (SEQ ID NO:19) with GSAG (SEQ ID NO:20), and the mutation in the turn region comprises double mutation K986G/V987G, K986P/V987P, K986G/V987P or K986P/V987G, wherein the amino acid numbering is based on SARS-CoV-2 Wuhan-Hu-1 isolate.

3. The immunogen polypeptide of claim 2, wherein the wildtype soluble S sequence comprises SEQ ID NO:14, or a variant with at least 99% sequence identity.

4. The immunogen polypeptide of claim 3, wherein the truncated HR2 comprises SEQ ID NO:9.

5. The immunogen polypeptide of claim 4, further comprising a N-terminal leader sequence shown in SEQ ID NO:15.

6. The immunogen polypeptide of claim 4, further comprising a trimerization motif at the C-terminus.

7. The immunogen polypeptide of claim 6, wherein the trimerization motif comprises foldon set forth in SEQ ID NO:26 or viral capsid protein SHP set forth in SEQ ID NO:27.

8. The immunogen polypeptide of claim 4, comprising the sequence shown in any one of SEQ ID NOs:32-37, or a variant thereof with at least 99% sequence identity.

9. The immunogen polypeptide of claim 1, further comprising the subunit sequence of a self-assembling nanoparticle that is fused to the C-terminus of the altered soluble S sequence.

10. A polynucleotide sequence that encodes the immunogen polypeptide of claim 2.

11. The polynucleotide sequence of claim 10, wherein the immunogen polypeptide further comprises a N-terminal leader.

12. The polynucleotide sequence of claim 10, encoding a fusion polypeptide comprising the immunogen polypeptide that is fused at its C-terminus to the N-terminus of the subunit sequence of a self-assembling nanoparticle.

13. A coronavirus immunogenic composition, comprising the immunogen polypeptide of claim 1 that is displayed on the surface of a self-assembling nanoparticle.

14. The immunogenic composition of claim 13, wherein the self-assembling nanoparticle comprises a trimeric sequence, and wherein C-terminus of the immunogen polypeptide is fused to N-terminus of the subunit sequence of the nanoparticle.

15. The immunogenic composition of claim 13, wherein the self-assembling nanoparticle comprises I3-01, E2p or ferritin.

16. The immunogenic composition of claim 13, further comprising a locking domain and/or a T-cell epitope that is fused to the C-terminus of the nanoparticle subunit sequence.

17. The immunogenic composition of claim 13, comprising: (1) a polypeptide sequence containing from N terminus to C terminus (a) an engineered SARS-CoV-2 spike polypeptide, a GS linker sequence, and nanoparticle sequence I3-01v9, (b) an engineered SARS-CoV-2 spike polypeptide, a GS linker sequence, and nanoparticle sequence E2p, or (c) an engineered SARS-CoV-2 spike polypeptide, a GS linker sequence, and nanoparticle sequence ferritin; or (2) a variant of the polypeptide sequence with at least 99% sequence identity.

18. The immunogenic composition of claim 17, wherein the engineered SARS-CoV-2 spike immunogen polypeptide comprises (a) substitution of the S1/S2 cleavage site $^{682}$RRAR$^{685}$ with GSAG, (b) double mutations K986G/V987G in the turn region, and (c) truncation of HR2 set forth in SEQ ID NO:9 at the C-terminus of the wildtype soluble S sequence; wherein the amino acid numbering is based on SARS-CoV-2 Wuhan-Hu-1 isolate.

19. The immunogenic composition of claim 17, wherein the engineered SARS-CoV-2 spike immunogen polypeptide comprises SEQ ID NO:33 or 34, or a variant thereof with at least 99% sequence identity.

20. The immunogenic composition of claim 19, comprising (1) a polypeptide sequence containing from N terminus to C terminus (a) the engineered SARS-CoV-2 spike polypeptide shown in SEQ ID NO:33, linker sequence shown in SEQ ID NO:22, nanoparticle sequence shown in SEQ ID NO:23, locking domain shown in SEQ ID NO:29, and T cell epitope shown in SEQ ID NO:30, (b) the engineered SARS-CoV-2 spike polypeptide shown in SEQ ID NO:33, linker sequence shown in SEQ ID NO:21, nanoparticle subunit sequence shown in SEQ ID NO:24, locking domain shown in SEQ ID NO:28, and T cell epitope shown in SEQ ID NO:30, or (c) the engineered SARS-CoV-2 spike polypeptide shown in SEQ ID NO:33, linker sequence shown in SEQ ID NO:21, nanoparticle sequence shown in SEQ ID NO:25; or (2) a variant of the polypeptide sequence with at least 99% sequence identity.

21. The immunogenic composition of claim 19, comprising the sequence shown in any one of SEQ ID NOs:38-40, or a variant thereof with at least 99% sequence identity.

22. A polynucleotide sequence that encodes a polypeptide sequence, wherein the polypeptide sequence comprises the immunogen polypeptide fused to the subunit sequence of the nanoparticle as set forth in claim 14.

23. A pharmaceutical composition, comprising the immunogenic composition of claim 13, and a pharmaceutically acceptable carrier.

24. A method for inhibiting a SARS-CoV-2 infection in a subject, comprising administering to the subject a pharmaceutically effective amount of the immunogenic composition of claim 13.

* * * * *